United States Patent
Hallahan et al.

(10) Patent No.: US 11,352,436 B2
(45) Date of Patent: Jun. 7, 2022

(54) ANTIBODIES TO TIP1 AND METHODS OF USE THEREOF

(71) Applicants: Dennis Hallahan, St. Louis, MO (US); Vaishali Kapoor, St. Louis, MO (US); Heping Yan, St. Louis, MO (US)

(72) Inventors: Dennis Hallahan, St. Louis, MO (US); Vaishali Kapoor, St. Louis, MO (US); Heping Yan, St. Louis, MO (US)

(73) Assignee: Washington University, St. Louis, MO (US)

( * ) Notice: Subject to any disclaimer, the term of this patent is extended or adjusted under 35 U.S.C. 154(b) by 154 days.

(21) Appl. No.: 16/485,100

(22) PCT Filed: Feb. 9, 2018

(86) PCT No.: PCT/US2018/017696
§ 371 (c)(1),
(2) Date: Aug. 9, 2019

(87) PCT Pub. No.: WO2018/148595
PCT Pub. Date: Aug. 16, 2018

(65) Prior Publication Data
US 2020/0239590 A1    Jul. 30, 2020

Related U.S. Application Data

(60) Provisional application No. 62/457,624, filed on Feb. 10, 2017.

(51) Int. Cl.
*C07K 16/30* (2006.01)
*A61P 35/00* (2006.01)
*A61K 39/00* (2006.01)

(52) U.S. Cl.
CPC .............. *C07K 16/30* (2013.01); *A61P 35/00* (2018.01); *A61K 2039/505* (2013.01); *C07K 2317/622* (2013.01); *C07K 2317/73* (2013.01); *C07K 2317/76* (2013.01); *C07K 2317/77* (2013.01)

(58) Field of Classification Search
CPC ...... A61N 5/10; A61N 5/00; A61K 39/39558; A61K 2039/545; A61K 2039/505; A61K 49/0032; A61K 49/0058; A61P 35/00; C07K 16/30; C07K 2317/622; C07K 2317/73; C07K 2317/76; C07K 2317/77; C07K 2317/34; C07K 2317/92; C07K 16/18; C12N 15/113; C12N 2310/20
See application file for complete search history.

(56) References Cited

U.S. PATENT DOCUMENTS

| | | |
|---|---|---|
| 4,241,046 A | 12/1980 | Papahadjopoulos et al. |
| 4,281,061 A | 7/1981 | Zuk |
| 4,394,448 A | 7/1983 | Szoka, Jr. et al. |
| 4,515,165 A | 5/1985 | Carroll |
| 4,529,561 A | 7/1985 | Hunt et al. |
| 4,670,386 A | 6/1987 | Sugaar |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,223,409 A | 6/1993 | Ladner et al. |
| 5,264,618 A | 11/1993 | Feigner et al. |
| 5,277,892 A | 1/1994 | Rhodes |
| 5,328,840 A | 7/1994 | Coller |
| 5,334,369 A | 8/1994 | Halushka et al. |
| 5,382,680 A | 1/1995 | Abraham et al. |
| 5,516,881 A | 5/1996 | Lee et al. |
| 5,614,535 A | 3/1997 | Juraszyk |
| 5,645,815 A | 7/1997 | Dean |
| 5,759,542 A | 6/1998 | Gurewich |
| 5,776,427 A | 7/1998 | Thorpe |
| 5,830,856 A | 11/1998 | Dean |
| 5,855,866 A | 1/1999 | Thorpe |
| 5,863,538 A | 1/1999 | Thorpe |
| 5,889,169 A | 3/1999 | Beach |
| 5,922,545 A | 7/1999 | Mattheakis et al. |
| 5,962,424 A | 10/1999 | Hallahan et al. |
| 5,965,132 A | 10/1999 | Thorpe |
| 5,977,313 A | 11/1999 | Heath |
| 6,004,554 A | 12/1999 | Thorpe |
| 6,033,847 A | 3/2000 | Shear |
| 6,051,230 A | 4/2000 | Thorpe |
| 6,068,829 A | 5/2000 | Ruoslahti |

(Continued)

FOREIGN PATENT DOCUMENTS

| | | | |
|---|---|---|---|
| CN | 104292330 A | * | 1/2015 |
| EP | 0723156 A2 | | 7/1996 |

(Continued)

OTHER PUBLICATIONS

Andria et al., Journal of Immunology, 1990, 144:2614-2619 (Year: 1990).*
Slobbe et al., Clinical and Experimental Immunology, 1994, 98:95-103 (Year: 1994).*
Beiboer et al., Journal of Molecular Biology, 2000, 296:833-849 (Year: 2000).*
Berglund et al., Protein Science, 2008, 17:606-613 (Year: 2008).*
Choi & Deane, Molecular BioSystems, 2011, 7:3327-3334 (Year: 2011).*
Malia et al., Proteins 2016; 84;427-434 (Year: 2016).*
Chiu et al., Antibodies, 2019, 8:55 (Year: 2019).*

(Continued)

*Primary Examiner* — Julie Wu
*Assistant Examiner* — John L Van Druff
(74) *Attorney, Agent, or Firm* — Polsinelli PC

(57) ABSTRACT

The disclosure provides antigen binding proteins useful in the recognition of tumor cells and tumor specific delivery of drugs and therapies.

14 Claims, 58 Drawing Sheets
(33 of 58 Drawing Sheet(s) Filed in Color)
Specification includes a Sequence Listing.

(56) References Cited

U.S. PATENT DOCUMENTS

| | | |
|---|---|---|
| 6,107,059 A | 8/2000 | Hart |
| 6,156,511 A | 12/2000 | Schatz |
| 6,156,736 A | 12/2000 | Weichselbaum |
| 6,174,687 B1 | 1/2001 | Rajotte |
| 6,232,287 B1 | 5/2001 | Ruoslahti et al. |
| 6,261,535 B1 | 7/2001 | Thorpe |
| 6,277,974 B1 | 8/2001 | Lo et al. |
| 6,316,208 B1 | 11/2001 | Roberts |
| 6,383,470 B1 | 5/2002 | Fritzsch |
| 6,403,383 B1 | 6/2002 | Casterlin |
| 6,576,239 B1 | 6/2003 | Ruoslahti |
| 6,605,712 B1 | 8/2003 | Weichselbaum |
| 6,630,570 B1 | 10/2003 | Licha et al. |
| 6,673,545 B2 | 1/2004 | Faris et al. |
| 7,018,618 B2 | 3/2006 | Lewis et al. |
| 7,056,506 B2 | 6/2006 | Varner |
| 7,122,361 B2 | 10/2006 | Liu et al. |
| 7,138,238 B2 | 11/2006 | Vodyanoy |
| 7,230,083 B2 | 6/2007 | Jonak et al. |
| 7,230,088 B2 | 6/2007 | Rajagopalan et al. |
| 10,259,884 B2 | 4/2019 | Hallahan et al. |
| 2002/0086288 A1 | 7/2002 | Bird et al. |
| 2002/0164663 A1 | 11/2002 | Fuqua et al. |
| 2003/0027159 A1 | 2/2003 | Ward et al. |
| 2003/0083261 A1 | 5/2003 | Yu et al. |
| 2003/0157025 A1 | 8/2003 | Unger et al. |
| 2003/0157482 A1 | 8/2003 | Keesee |
| 2006/0046271 A1 | 3/2006 | Hallahan |
| 2007/0081993 A1 | 4/2007 | Kufer et al. |
| 2008/0118978 A1 | 5/2008 | Sato et al. |
| 2008/0305111 A1 | 12/2008 | Evans et al. |
| 2010/0039023 A1 | 2/2010 | Rogojevic et al. |
| 2010/0041074 A1 | 2/2010 | Kimura |
| 2010/0111852 A1 | 5/2010 | Koshida |
| 2010/0111959 A1 | 5/2010 | Swanson et al. |
| 2010/0135905 A1 | 6/2010 | Hallahan et al. |
| 2014/0316186 A1 | 10/2014 | Hallahan et al. |
| 2014/0369929 A1 | 12/2014 | Hallahan et al. |
| 2017/0298142 A1 | 10/2017 | Hallahan et al. |

FOREIGN PATENT DOCUMENTS

| | | | |
|---|---|---|---|
| EP | 0723156 A3 | 4/1998 | |
| EP | 1217377 B1 | 6/2002 | |
| WO | 1992020796 A2 | 11/1992 | |
| WO | 1993014791 A2 | 8/1993 | |
| WO | 1995034315 A1 | 12/1995 | |
| WO | 1998010795 A3 | 3/1998 | |
| WO | 1999004238 A2 | 1/1999 | |
| WO | 2000066182 A1 | 11/2000 | |
| WO | 2001009611 A2 | 2/2001 | |
| WO | 2001009611 A3 | 7/2001 | |
| WO | 2006028993 A2 | 3/2006 | |
| WO | WO-2007142277 A1 * | 12/2007 | ............ C07K 16/22 |
| WO | WO-2008102359 A1 * | 8/2008 | ............... A61P 1/04 |
| WO | WO-2008145338 A2 * | 12/2008 | ............ C07K 16/30 |
| WO | WO-2010040572 A2 * | 4/2010 | ......... C07K 16/1018 |
| WO | 2013019730 A1 | 2/2013 | |
| WO | 2013049830 A2 | 4/2013 | |
| WO | WO-2014130965 A1 * | 8/2014 | ............... A61P 3/00 |
| WO | WO-2015017113 A2 * | 2/2015 | ............ C07K 16/30 |
| WO | WO-2015089449 A2 * | 6/2015 | ............. A61P 35/00 |
| WO | 2015116653 A1 | 8/2015 | |
| WO | 2018148595 A1 | 8/2016 | |
| WO | WO-2020257760 A1 * | 12/2020 | ......... C07K 16/2803 |

OTHER PUBLICATIONS

Reynaud, C. et al., "The PDZ Protein TIP-1 Interacts with the Rho Effector Rhotekin and Is Involved in Rho Signaling to the Serum Response Element," J. Biol. Chem., Oct. 2000, pp. 33962-33968, vol. 275, No. 43.

Rosell, R. et al., "Maintenance therapy and precision medicine in NSCLC," Nat. Rev. Clin. Oncol., 2013, pp. 549-550, vol. 10.

Rosenberg, E. et al., "Destruction of Human Lymphoid Tissue-Culture Cell Lines by Human Peripheral Lymphocytes in 51Cr-Release Cellular Cytotoxicity Assays," J. Nat. Cancer Inst., Feb. 1974, pp. 345-352, vol. 52, No. 2.

Rousset, R. et al., "The C-terminus of the HTLV-1 Tax oncoprotein mediates interaction with the PDZ domain of cellular proteins," Oncogene, 1998, pp. 643-654, vol. 16, Stockton Press.

Rudikoff, S. et al., "Single amino acid substitution altering antigen-binding specificity," PNAS, Mar. 1982, pp. 1979-1983, vol. 79.

Ruoslahti, E., "RGD and Other Recognition Sequences for Integrins," Annu. Rev. Cell Dev. Biol., 1996, pp. 697-715, vol. 12.

Ryder, K. et al., "An Enzyme Immunoassay Procedure for Cancer Antigen 125 Evaluated," Clin. Chem., 1988, pp. 2513-2516, vol. 34, No. 12.

Sakamoto, N. et al., "Inhibition of Angiogenesis and Tumor Growth by a Synthetic Laminin Peptide, CDPGYIGSR-NH2," Cancer Res., Feb. 1991, pp. 903-906, vol. 51.

Sano, T. et al., "Immunohistochemical overexpression of p16 protein associated with intact retinoblastoma protein expression in cervical cancer and cervical intraepithelial neoplasia," Pathology Int., 1998, pp. 580-585, vol. 48.

Sano, T. et al., "Overexpression of p16 and p14ARF is associated with human papillomavirus infection in cervical squamous cell carcinoma and dysplasia," Pathology Int., 2002, pp. 375-383, vol. 52.

Sano, T., et al., "Expression Status of p16 Protein Is Associated with Human Papillomavirus Oncogenic Potential in Cervical and Genital Lesions," Am. J. Pathol., 1998, pp. 1741-1748, vol. 153, No. 6.

Scott, A. et al., "Antibody therapy of cancer," Nat. Rev. Cancer, Apr. 2012, pp. 278-287, vol. 12.

Serrano, M. et al., "A new regulatory motif in cell-cycle control causing specific inhibition of cyclin D/CDK4," Nature, Dec. 16, 1993, pp. 704-707, vol. 366.

Shalaby, M. et al., "Development of Humanized Bispecific Antibodies Reactive with Cytotoxic Lymphocytes and Tumor Cells Overexpressing the HER2 Protooncogene," J. Exp. Med., Jan. 1992, pp. 217-225, vol. 175, The Rockefeller University Press.

Sherr, C., "The INK4a/ARF Network in Tumor Suppression," Nat. Rev. Mol. Cell Bio., Oct. 2001, pp. 731-737, vol. 2.

Shigemasa, K. et al., "p16 overexpression: a potential early indicator of transformation in ovarian carcinoma," J. Soc. Gynecol. Invest., 1997, pp. 95-102, vol. 4, No. 2.

Shim, C. et al., "Profiling of differentially expressed genes in human primary cervical cancer by complementary DNA expression array," Clin. Cancer Res., Dec. 1998, pp. 3045-3050, vol. 4.

Siegel, R. et al., "Cancer Statistics, 2015," CA Cancer J. Clin., 2015, pp. 5-29, vol. 65.

Sivam, G. et al., "Therapeutic Efficacy of a Doxorubicin Immunoconjugate in a Preclinical Model of Spontaneous Metastatic Human Melanoma," Cancer Res., Jun. 1, 1995, pp. 2352-2356, vol. 55.

Stupp, R. et al., "Radiotherapy plus Concomitant and Adjuvant Temozolomide for Glioblastoma," N. Engl. J. Med., Mar. 2005, pp. 987-996, vol. 352, No. 10.

Sudarsanam, S., "Structural Diversity of Sequentially Identical Subsequences of Proteins: Identical Octapeptides Can Have Different Conformations," Proteins: Structure, Function, and Genetics, 1998, pp. 228-231, vol. 30, Wiley-Liss, Inc.

Suneja, S. et al., "Quantification of a neurotrophin receptor from submilligram quantities of brain tissue using Western blotting," Brain Res. Protocols, 1998, pp. 88-93, vol. 3.

Takeuchi, H. et al., "Altered p16/MTS1/CDKN2 and cyclin D1/PRAD-1 gene expression is associated with the prognosis of squamous cell carcinoma of the esophagus," Clin. Cancer Res., Dec. 1997, pp. 2229-2236, vol. 3.

Tam, S. et al., "Differential Expression and Cell Cycle Regulation of the Cyclin-dependent Kinase 4 Inhibitor p16Ink4," Cancer Res., Nov. 15, 1994, pp. 5816-5820, vol. 54.

Tolsma, S. et al., "Transformation of NIH/3T3 to Anchorage Independence by H-Ras Is Accompanied by Loss of Suppressor Activity," Exp Cell Res., 1993, pp. 232-239, vol. 205.

(56) References Cited

OTHER PUBLICATIONS

Topper, M. et al., "Differentiation between the EGFR antibodies necitumumab, cetuximab, and panitumumab: Antibody internalization and EGFR degradation," J. Clin. Oncol., 2011, 3 pgs., vol. 29, No. 15_suppl.

Tsujie, M. et al., "Expression of Tumor Suppressor Gene p16INK4 Products in Primary Gastric Cancer," Oncology, 2000, pp. 126-136, vol. 58.

Vajdos, F. et al., "Comprehensive Functional Maps of the Antigen-binding Site of an Anti-ErbB2 Antibody Obtained with Shotgun Scanning Mutagenesis," J. Mol. Biol., 2002, pp. 415-428, vol. 320.

Vithayathil, R. et al., "The Scope of Phage Display for Membrane Proteins," NIH Public Access Author Manuscript, 18 pgs., J. Mol. Biol., Dec. 9, 2011, pp. 499-510, vol. 414, No. 4.

Voest, E. et al., "Inhibition of Angiogenesis In Vivo by Interleukin 12," J. Natl. Cancer Inst., Apr. 19, 1995, pp. 581-586, vol. 87, No. 8.

Walther, W. et al., "Therapeutic Genes for Cancer Gene Therapy," Molecular Biotechnology, 1999, pp. 21-28, vol. 13.

Wang, H. et al., "TIP-1 Translocation onto the Cell Plasma Membrane Is a Molecular Biomarker of Tumor Response to Ionizing Radiation," PLoS One, Aug. 2010, pp. 1-12, vol. 5, No. 8, e12051.

Wang, H. et al., "Tax-interacting protein 1 coordinates the spatiotemporal activation of Rho GTPases and regulates the infiltrative growth of human glioblastoma," Oncogene, 2014, pp. 1558-1569, vol. 33.

Weiss, G. et al., "Rapid mapping of protein functional epitopes by combinatorial alanine scanning," PNAS, Aug. 1, 2000, pp. 8950-8954, vol. 97, No. 16.

Wentzensen, N. et al., "Identification of High-Grade Cervical Dysplasia by the Detection of p16INK4a in Cell Lysates Obtained From Cervical Samples," Cancer, Nov. 1, 2006, pp. 2307-2313, vol. 107, No. 9.

Woltering, E. et al., "Somatostatin Analogues Inhibit Angiogenesis in the Chick Chorioallantoic Membrane," J. Surg. Res., 1991, pp. 245-251, vol. 50.

Wong, Y. et al., "Frequent loss of heterozygosity of chromosome 3 short arm detected by PCR-based microsatellite polymorphisms in cervical squamous cell carcinoma," Cancer Letters, 1997, pp. 161-164, vol. 115.

Wong, Y. et al., "p16INK4 and p15INK4B Alterations in Primary Gynecologic Malignancy," Gynecologic Onco., 1997, pp. 319-324, vol. 65, Article No. GO974669.

Wu, C-C. et al., "Identification of a New Peptide for Fibrosarcoma Tumor Targeting and Imaging In Vivo," J. Biomed. Biotechnol., 2010, pp. 1-10, vol. 2010, Article 167045.

Wu, H. et al., "Humanization of a Murine Monoclonal Antibody by Simultaneous Optimization of Framework and CDR Residues," J. Mol. Biol., 1999, pp. 151-162, vol. 294, Academic Press.

Xu, X. et al., "Cell cycle proteins PP5 associated with Rad9 and uses in screening for a bioactive agent," Database HCAPLUS on STN, 2001, Abstract WO01/64913, Accession No. 2001:661624, Registry No. 263887-03-02 for human gene rad9 for SEQ ID No. 8, 1 pg.

Xu, X. et al., "The tandem affinity purification method: An efficient system for protein complex purification and protein interaction identification," Protein Expr. Purif., 2010, pp. 149-156, vol. 72, No. 2.

Yan, H. et al., "Anti-tax interacting protein-1 (TIP-1) monoclonal antibody targets human cancers," Oncotarget, 2016, pp. 43352-43362, vol. 7, No. 28.

Yokota, T. et al., "Rapid Tumor Penetration of a Single-Chain Fv and Comparison with Other Immunoglobulin Forms," Can. Res., Jun. 15, 1992, pp. 3402-3408, vol. 52.

Zang, L. et al., "Screening and Identification of a peptide specifically targeted to NCI-H1299 from a phage display peptide library," Cancer Letters, 2009, pp. 64-70, vol. 281, No. 1.

Zhang, J. et al., "Structural Basis of beta-Catenin Recognition by Tax-interacting Protein-1," J. Mol. Biol., 2008, pp. 255-263, vol. 384, No. 1.

Zhang, Y. et al., "XL-184, a MET, VEGFR-2 and RET kinase inhibitor for the treatment of thyroid cancer, glioblastoma multiforme and NSCLC," NIH Public Access Author Manuscript, Jan. 2012, pp. 1-16, published in final edited form as: IDrugs, Feb. 2010, pp. 112-121, vol. 13, No. 2.

Zoetewey, D. et al., "Promiscuous Binding at the Crossroads of Numerous Cancer Pathways: Insight from the Binding of Glutaminase Interacting Protein with Glutaminase L," Biochem., 2011, pp. 3528-3539, vol. 50.

Hallahan, D. et al., "Cell Adhesion Molecules Mediate Radiation-induced Leukocyte Adhesion to the Vascular Endothelium," Cancer Res., Nov. 15, 1996, pp. 5150-5155, vol. 56.

Hallahan, D. et al., "c-jun and Egr-1 Participate in DNA Synthesis and Cell Survival in Response to Ionizing Radiation Exposure," J. Bio. Chem., Dec. 22, 1995, pp. 30303-30309, vol. 270, No. 51.

Hallahan, D. et al., "E-selectin gene induction by ionizing radiation is independent of cytokine induction," Biochem. Biophys. Res. Commun., Dec. 26, 1995, pp. 784-795, vol. 217, No. 3.

Hallahan, D. et al., "Integrin-mediated targeting of drug delivery to irradiated tumor blood vessels," Cancer Cell, Jan. 2003, pp. 63-74, vol. 3.

Hallahan, D. et al., "Intercellular adhesion molecule 1 knockout abrogates radiation induced pulmonary inflammation," PNAS, Jun. 1997, pp. 6432-6437, vol. 94.

Hallahan, D. et al., "Ionizing Radiation Mediates Expression of Cell Adhesion Molecules in Distinct Histologicfrudial Patterns within the Lung," Cancer Res., Jun. 1, 1997, pp. 2096-2099, vol. 57.

Hallahan, D. et al., "Nuclear Factor kB Dominant Negative Genetic Constructs Inhibit X-ray Induction of Cell Adhesion Molecules in the Vascular Endothelium," Cancer Res., Dec. 1, 1998, pp. 5484-5488, vol. 58.

Hallahan, D. et al., "Radiation Signaling Mediated by Jun Activation following Dissociation from a Cell Type-specific Repressor," J. Bio. Chem., Mar. 5, 1993, pp. 4903-4907, vol. 268, No. 7.

Hallahan, D. et al., "Radiation-Mediated Control of Drug Delivery," Am. J. Clin. Oncol., 2001, pp. 473-480, vol. 24, No. 5.

Hallahan, D. et al., "Spatial and temporal control of gene therapy using ionizing radiation," Nature Medicine, Aug. 1995, pp. 786-791, vol. 1, No. 8.

Hallahan, D. et al., Targeting drug delivery to radiation-induced neoantigens in tumor microvasculature, J. Controlled Release, 2001, pp. 183-191, vol. 74.

Hallahan, D., "Radiation-Mediated Gene Expression in the Pathogenesis of the Clinical Radiation Response," Seminars Radiat. Oncol., Oct. 1996, pp. 250-267, vol. 6, No. 4.

Hampson, L. et al., "The PDZ protein Tip-1 is a gain of function target of the HPV16 E6 oncoprotein," Int. J. Oncol., 2004, pp. 1249-1256, vol. 25.

Han, Z. et al., "Noninvasive assessment of cancer response to therapy," Nat. Med., Mar. 2008, pp. 343-349, vol. 14, No. 3.

Han, M. et al., "The PDZ protein TIP-1 facilitates cell migration and pulmonary metastasis of human invasive breast cancer cells in athymic mice," NIH Public Access Author Manuscript, 13 pgs., Biochem. Biophys. Res. Commun., May 2012, pp. 139-145, vol. 422, No. 1.

Han, M. et al., "Expression of TIP-1 Confers Radioresistance of Malignant Glioma Cells," PLoS One, Sep. 2012, pp. 1-13, vol. 7, No. 9, e45402.

Han, M. et al., "Expression of Tax-interacting protein 1 (TIP-1) facilitates angiogenesis and tumor formation of human glioblastoma cells in nude mice," NIH Public Access Author Manuscript, Jan. 2014, pp. 1-19, published in final edited form as: Cancer Lett., Jan. 2013, pp. 55-64, vol. 328, No. 1.

Harari, O. et al., "Targeting an adenoviral gene vector to cytokine-activated vascular endothelium via E-selectin," Gene Therapy, 1999, pp. 801-807, vol. 6, Stockton Press.

Hariri, G. et al., "Radiation-Guided Drug Delivery to Mouse Models of Lung Cancer," Clin. Cancer Res., Oct. 2010, pp. 4968-4977, vol. 16, No. 20.

Harris, B. et al., "Mechanism and role of PDZ domains in signaling complex assembly," J. Cell Sci., 2001, pp. 3219-3231, vol. 114, No. 18.

He, X-S. et al., "Expression, deleton and mutation of p16 gene in human gastric cancer," World J. Gastroenterol., 2001, pp. 515-521, vol. 7, No. 4.

(56) References Cited

OTHER PUBLICATIONS

Hirama, T. et al., "p16 (CDKN2-Cyclin-dependent Kinase-4 Inhibitor-Multiple Tumor Suppressor-1) Gene Is Not Altered in Uterine Cervical Carcinomas or Cell Lines," Modern Pathology, 1996, pp. 26-30, vol. 9, No. 1, Abstract only.

Hirata, "Fate of Intravenously Injected Human Tumor Cells in the Lung of Nude Mice Following Whole-Body X-Irradiation," Invasion Metastasis, 1985, pp. 61-70, Abstract only.

Hirata, H. et al., "Artificial Metastases and Decrease of Fibrinolysis in the Nude Mouse Lung After Hemithoracic Irradiation," Clin. Expl. Metatasis, 1984, pp. 311-319, vol. 2, No. 4, Abstract only.

Humira™ (adalimumab) Package Insert, Dec. 20, 2002, 16 pgs.

Huston, J., "Protein engineering of antibody binding sites: Recovery of specific activity in an anti-digoxin single-chain Fv analogue produced in *Escherichia coli*," PNAS, Aug. 1998, pp. 5879-5883, vol. 85.

Ikeda, K. et al., "Extraction and Analysis of Diagnostically Useful Proteins from Formalin-fixed, Paraffin-embedded Tissue Sections," J. Histochem. Cytochem., 1998, pp. 397-403, vol. 46, No. 3.

Ingber, D. et al., "Synthetic analogues of fumagillin that inhibit angiogenesis and suppress tumour growth," Nature, Dec. 6, 1990, pp. 555-557, vol. 348.

International Search Report and Written Opinion dated Jan. 4, 2013 from related Patent Application No. PCT/US2012/048856; 13 pgs.

International Search Report and Written Opinion dated May 17, 2018 from related Patent Application No. PCT/US2018/017696; 9 pgs.

International Search Report and Written Opinion dated May 7, 2015 from related Patent Application No. PCT/US2015/013241; 9 pgs.

Ito, T. et al., "Preclinical Assessments of 90Y-labeled C110 Anti-Carcinoembryonic Antigen Immunotoxin: A Therapeutic Immunoconjugate for Human Colon Cancer," Cancer Res., Jan. 1, 1991, pp. 255-260, vol. 51.

Jaboin, J. et al., "Using In Vivo Biopanning for the Development of Radiation-Guided Drug Delivery Systems," Methods Mol. Biol., Gene Ther. Cancer, 2009, pp. 285-300, vol. 542, Humana Pres0073.

Jahroudi, N. et al., "Ionizing irradiation increases transcription of the von Willebrand factor gene in endothelial cells," Blood, Nov. 15, 19966, pp. 3801-3814, vol. 88, No. 10.

Jain, R., "Barriers to Drug Delivery in Solid Tumors," Scientific American, Jul. 1994, pp. 58-65, vol. 271.

Johnson, T. et al., "Therapy of B-cell lymphomas with monoclonal antibodies and radioimmunoconjugates: the Seattle experience," Ann. Hematol., 2000 pp. 175-182, vol. 79.

Kanamori, M. et al., "The PDZ Protein Tax-interacting Protein-1 Inhibits beta-Catenin Transcriptional Activity and Growth of Colorectal Cancer Cells," J. Biol. Chem., Oct. 2003, pp. 38758-38764, vol. 278, No. 40.

Kapoor, V. et al., "Abstract 4599: Antibody targeting PDZ domain of TIP-1 induces proliferation arrest through AKT/mTOR signaling inhibition in lung cancer and glioblastoma," In: Proceedings AACR Annual Meeting, Apr. 1-5, 2017, Washington, D.C., Cancer Res., Jul. 2017, Vol. 77, No. 13 Suppl.

Kastan, M. et al., "ATM kinase modulation for screening and therapies," Database HCAPLUS on STN, 2000, Abstract WO00/47760, Accession No. 2000:573954, Registry No. 288259-02-9 for SEQ ID No. 8 and SEQ ID No. 10 and Registry No. 288259-18-7 for SEQ ID No. 13, 1 pg.

Kay, B. et al., "PDZ Domains and Their Ligands," Chem. Biol., Apr. 2004, pp. 423-425, vol. 11.

Kelley, M. et al., "CDKN2 in HPV-Positive and HPV-Negative Cervical-Carcinoma Cell Lines," Int. J. Cancer, 1995 pp. 226-230, vol. 63.

Khleif, S. et al., "Inhibition of cyclin D-CDK4/CDK6 activity is associated with an E2F-mediated induction of cyclin kinase inhibitor activity," PNAS, Apr. 1996, pp. 4350-4354, vol. 93.

Kim, J. et al., "Absence of p15INK4B and p16INK4A Gene Alterations in Primary Cervical Carcinoma Tissues and Cell Lines with Human Papillomavirus Infection," Gynecologic Oncology, 1998, pp. 75-79, vol. 70, Article No. GO985041.

Kim, Y. et al., "Underexpression of Cyclin-Dependent Kinase (CDK) Inhibitors in Cervical Carcinoma," Gynecologic Oncology, 1998, pp. 38-45, vol. 71, Article No. GO985134.

Kirk, C. et al., "Gene-Modified Dendritic Cells for Use in Tumor Vaccines," Human Gene Therapy, Apr. 10, 2000, pp. 797-806, vol. 11, Mary Ann Liebert, Inc.

Klaes, R. et al., "Overexpression of p16INK4A as a Specific Marker for Dysplastic and Neoplastic Epthelial Cells of the Cervis Uteri," Int. J. Cancer, 2001, pp. 276-284, vol. 92.

Koivunen, E. et al., "Isolation of a Highly Specific Ligand for the alpha5beta1 Integrin from a Phage Display Library," J. Cell Biol., 1994, pp. 373-380, vol. 124.

Koivunen, E. et al., "Selection of Peptides Binding to the alpha5beta1 Integrin from Phage Display Library," J. Bio. Chem., Sep. 25, 1993, pp. 20205-20210, vol. 268, No. 27.

Kolb, H. et al., "Click Chemistry: Diverse Chemical Function from a Few Good Reactions," Angew. Chem. Int. Ed., 2001, pp. 2004-2021, vol. 40, Wiley-VCH Verlag GmbH, Weinheim.

Kosfeld, M. et al., "Identification of a New Cell Adhesion Motif in Two Homologous Peptides from the COOH-terminal Cell Binding Domain of Human Thrombospondin," J. Biol. Chem., Apr. 25, 1993, pp. 8808-8814, vol. 268, No. 12.

Krauer, K. et al., "Antitumor Effect of 2'-Deoxy-5-fluorouridine Conjugates against a Murine Thymoma and Colon Carcinoma Xenografts," Cancer Res., Jan. 1, 1992, pp. 132-137, vol. 52.

Kurnik, B. et al., "Prospective study of atrial natriuretic peptide for the prevention of radio-contrast-induced nephropathy," Database HCAPLUS on STN, Abstract, Am. J. Kidney Disease, 1998, Accession No. 1998:248017, Registry No. 95896-08-5 for atrial natriuetic peptide-25, for SEQ ID No. 11, 1 pg.

Kwon, T. et al., "Akt Protein Kinase Inhibits Rac1-GTP Binding Through Phosphorylation at Serine 71 of Rac1," J. Biol. Chem., Jan. 2000, pp. 423-428, vol. 275, No. 1.

Li, H-F. et al., "Radiation-induced Akt activation modulates radioresistance in human glioblastoma cells," Radiation Oncology, 2009, pp. 1-10, vol. 4, No. 43.

Lieberman, H. et al., "A human homolog of the Schizosaccharomyces pombe rad9+ checkpoint control gene," PNAS, Nov. 1996, pp. 13890-13895, vol. 93.

Liggett, W. et al., "Role of the p16 Tumor Suppressor Gene in Cancer," J. Clin. Onocl., Mar. 1998, pp. 1197-1206, vol. 16, No. 3.

Llovet, J. et al., "Arterial embolisation or chemoembolisation versus symptomatic treatment in patients with unresectable hepatocellular carcinoma: a randomised controlled trial," Lancet, May 18, 2002, pp. 1734-1739, vol. 359.

Lohse, J. et al., "Fluorescein-Conjugated Lysine Monomers for Solid Phase Synthesis of Fluorescent Peptides and PNA Oligomers," Bioconj. Chem., 1997, pp. 503-509, vol. 8, No. 4.

Lowery, A. et al., "Tumor-targeted delivery of liposome-encapsulated doxorubicin by use of a peptide that selectively binds to irradiated tumors," NIH Public Access Author Manuscript, 15 pgs. , J. Control Release, Feb. 28, 2011, pp. 117-124, vol. 150, No. 1.

Maccallum, R. et al., "Antibody-antigen Interactions: Contact Analysis and Binding Site Topography," J. Mol. Biol., 1998, pp. 732-745, vol. 262.

Mackensen, A. et al., "Immunostimulatory Cytokines in Somatic Cells and Gene Therapy of Cancer," Cytokine & Growth Factor Rev., 1997, pp. 119-128, vol. 8, No. 2, Elsevier Science Ltd., Great Britain.

Maione, T. et al., "Inhibition of Angiogenesis by Recombinant Human Platelet Factor-4 and Related Peptides," Science, New Series, Jan. 5, 1990, pp. 77-79, vol. 247, No. 4938.

Mao, C. et al., "Evaluation of a new p16INK4a ELISA test and a high-risk HPV DNA test for cervical cancer screening: Results from proof-of-concept study," Int. J. Cancer, 2007, pp. 2435-2438, vol. 120.

Martin, F., et al., "Targeted Retroviral Infection of Tumor Cells by Receptor Cooperation," J. Virology, Feb. 2003, pp. 2753-2756, vol. 77, No. 4.

Mauceri, H. et al., "Tumor Necrosis Factor alpha (TNF-alpha) Gene Therapy Targeted by Ionizing Radiation Selectively Damages Tumor Vasculature," Cancer Res., Oct. 1, 1996, pp. 4311-4314, vol. 56.

(56) References Cited

OTHER PUBLICATIONS

Mccabe, J., "The effects of detergents on the enzyme-linked immunosorbent assay (ELISA) of blood group substances," J. Immunol., Methods, Apr. 1988, pp. 129-135, vol. 108, No. 1, Abstract only.

Menon, R. et al., "Functional Implications of Structural Predictions for Alternative Splice Proteins Expressed in Her2/neu-Induced Breast Cancers," NIH Public Access Author Manuscript, Dec. 2, 2012, pp. 1-19, published in final edited form as: J. Proteome Res., Dec. 2, 2011, pp. 5503-5511, vol. 10, No. 12.

Milde-Langosch, K. et al., "P16/MTS1 and pRB expression in endometrial carcinomas," Virchows Arch, 1999, pp. 23-28, vol. 434.

Milde-Langosch, K. et al., "p16/MTS1 Inactivation in Ovarian Carcinomas: High Frequency Of Reduced Protein Expression Associated With Hyper-Methylation Or Mutation In Endometrioid and Mucinous Tumors," Int. J. Cancer (Pred. Oncol.), 1998, pp. 61-65, vol. 79.

Mohanty, S. et al., "PDZ Domain Recognition: Insight from Human Tax-Interacting Protein 1 (TIP-1) Interaction with Target Proteins," Biology, 2015, pp. 88-103, vol. 4.

Molema, G. et al., "Tumor Vascular Endothelium: Barrier or Target in Tumor Directed Drug Delivery and Immunotherapy," Pharm. Res., 1997, pp. 2-10, vol. 14, No. 1.

Munro, S. et al., "An Hsp70-like Protein in the ER: Identity with the 78 kd Glucose-Regulated Protein and Immunoglobulin Heavy Chain Binding Protein," Cell, Jul. 18, 1986, pp. 291-300, vol. 46.

Myung, N. et al., "Loss of p16 and p27 is associated with progression of Human gastric cancer," Cancer Letters, 2000, pp. 129-136, vol. 153.

Nakao, Y. et al., "Induction of p16 during immortalization by HPV 16 and 18 and not during malignant transformation," British J. Cancer, 1997, pp. 1410-1416, vol. 75, No. 10.

Newton, J. et al., "In Vivo Bacteriophage Display for the Discovery of Novel Peptide-Based Tumor-Targeting Agents," Methods Mol. Biol.: Biosensors and Biodetection, 2009, pp. 275-290, vol. 504, Humana Press.

Newton, J. et al., "Phage Peptide Display," Handb. Exp. Pharmacol., 2008, pp. 145-163, vol. 185, Part 2.

Notice of Allowance dated Mar. 20, 2017 from related U.S. Appl. No. 14/166,251; 9 pgs.

Notice of Allowance dated Sep. 20, 2018 from related U.S. Appl. No. 15/628,209; 9 pgs.

Nuovo, G. et al., "In situ detection of the hypermethylation-induced inactivation of the p16 gene as an early event in oncogenesis," PNAS, Oct. 26, 1999, pp. 12754-12759, vol. 96, No. 22.

O'Brien, P. et al., "Antibody Phage Display: Methods and Protocols," E-Streams, Dec. 2002, pp. 1-2, vol. 5, No. 12.

Office Action dated Jan. 13, 2017 from related U.S. Appl. No. 14/166,251; 8 pgs.

Office Action dated Jul. 5, 2016 from related U.S. Appl. No. 14/166,251; 14 pgs.

Oliver, A. et al., "The HPV16 E6 binding protein Tip-1 interacts with ARHGEF16, which activates Cdc42," Br. J. Cancer, 2011, pp. 324-331, vol. 104, No. 2.

O'Nions, J. et al., "p73 is over-expressed in vulval cancer principally as the Δ2 isoform," British J. Cancer, 2001, pp. 1551-1556, vol. 85, No. 10.

O'Reilly, M. et al., "Angiostatin: A Novel Angiogenesis Inhibitor That Mediates the Suppression of Metastases by a Lewis Lung Carcinoma," Cell, Oct. 21, 1994, pp. 315-328, vol. 79.

O'Reilly, M. et al., "Endostatin: An Endogenous Inhibitor of Angiogenesis and Tumor Growth," Cell, Jan. 24, 1997, pp. 277-285, vol. 88.

Pan, X-M. et al., "What Is the Minimum Number of Residues to Determine the Secondary Structural State?," J. Protein Chem., 1999, pp. 579-584, vol. 18, No. 5.

Pasqualini, R. et al., "Organ targeting in vivo using phage display peptide libraries," Nature, Mar. 28, 1996, pp. 364-366, vol. 380.

Passarella, R. et al., "Recombinant Peptides as Biomarkers for Tumor Response to Molecular Targeted Therapy," NIH Public Access Author Manuscript, 25 pgs., Clin. Cancer Res., Oct. 15, 2009, pp. 6421-6429, vol. 15, No. 20.

Passarella, R. et al., "Targeted Nanoparticles That Deliver a Sustained, Specific Release of Paclitaxel to Irradiated Tumors," Cancer Res., Jun. 1, 2010, pp. 4550-4559, vol. 70, No. 11.

Passaro, A. et al., "Personalized treatment in advanced ALK-positive non-small cell lung cancer: from bench to clinical practice," Onco Targets Ther., 2016, pp. 6361-6376, vol. 9.

Pastan, I., "Targeted therapy of cancer with recombinant immunotoxins," Biochimica et Biophysica Acta, 1997, pp. C1-C6, vol. 1333.

Paul, W., Fundamental Immunology, 3rd Edition, 1993, pp. 292-295, Chapter 9, Raven Press, Ltd.

Phillips, J. et al., "Scalable Molecular Dynamics with NAMD," NIH Public Access Author Manuscript, 43 pgs., J. Comput. Chem., Dec. 2005, pp. 1781-1802, vol. 26, No. 16.

Pinsky, D. et al., "Hypoxia-induced Exocytosis of Endothelial Cell Weibel-Palade Bodies. A Mechanism for Rapid Neutrophil Recruitment after Cardiac Preservation," J. Clin. Invest., Jan. 1996, pp. 493-500, vol. 97, No. 2.

Plath, T. et al., "A Novel Function for the Tumor Suppressor p16INK4a: Induction of Anoikis via Upregulation of the alpha5beta1 Fibronectin Receptor," J. Cell Bio., Sep. 18, 2000, pp. 1467-1477, vol. 150, No. 6.

Qualtiere, L. et al., "Effects of Ionic and Nonionic Detergents on Antigen-Antibody Reactions," J. Immunol., Nov. 1977, pp. 1645-1651, vol. 119.

Queen, C. et al., "Immunoglobulin Gene Transcription Is Activated by Downstream Sequence Elements," Cell, Jul. 1983, pp. 741-748, vol. 33, No. 3.

Rajotte, D. et al., "Membrane Dipeptidase Is he Receptor for a Lung-targeting Peptide Identified by in vivo Phage Display," J. Bio. Chem., Apr. 23, 1999, p. 11593-11598, vol. 274, No. 17.

Rangel, R. et al., "Combinatorial targeting and discovery of ligand-receptors in organelles of mammalian cells," Nat. Commun., 2012, pp. 1-10, vol. 3, No. 788.

Albini, A. et al., "Inhibition of Angiogenesis and Vascular Tumor Growth by Interferon-Producing Cells," Am. J. Pathol., 2000, pp. 1381-1393, vol. 156.

Alewine, C. et al., "TIP-1 Has PDZ Scaffold Antagonist Activity," Mol. Biol. Cell, Oct. 2006, pp. 4200-4211, vol. 17, No. 10.

Arap, W. et al., "Cancer Treatment by Targeted Drug Delivery to Tumor Vasculature in a Mouse Model," Sci., Jan. 16, 1998, pp. 377-380, vol. 279.

Auperin, A. et al., "Meta-Analysis Of Concomitant Versus Sequential Radiochemotherapy in Locally Advanced Non-Small-Cell Lung Cancer," J. Clin. Oncol., May 2010, pp. 2181-2190, vol. 28, No. 13.

Baillie, C.T. et al., "Tumor vasculature—a potential therapeutic agent," British J. Can., 1995, pp. 257-267, vol. 72.

Barani, I. et al., "Radiation Therapy of Glioblastoma," In: J. Raizer and A. Parsa (eds.), Current Understanding and Treatment of Gliomas, Cancer Treat. Res., 2015, pp. 49-73, vol. 163.

Bender, H. et al., "External Beam Radiation Enhances Antibody Mediated Radiocytotoxicity in Human Glioma Cells in Vitro," Anticancer Res., 1997, pp. 1797-1802, vol. 17.

Bendig, M., "Humanization of Rodent Monoclonal Antibodies by CDR Grafting," Methods: A Companion to Methods in Enzymology, 1995, pp. 83-93, vol. 8.

Besser, J. et al.,"Tip-1 induces filopodia growth and is important for gastrulation movements during zebrafish development," Dev. Growth Differ., 2007, pp. 205-214, vol. 49.

Bhakdi, S., "Removal of SDS From Proteins For Immunochemical Analyses: A Simple Method Utilizing Ultracentrifugation in Sucrose Density Gradients Containing Non-Ionic Detergent," J. Biochem. Biophys. Methods, 1980, pp. 79-90, vol. 2.

Bird, R. et al., "Single-Chain Antigen-Binding Proteins," Science, New Series, Oct. 21, 1988, pp. 423-426, vol. 242, No. 4877.

Boothman, D. et al., "Induction of Tissue-type Plasminogen Activator by Ionizing Radiation in Human Malignant Melanoma Cells," Cancer Res., 1991, pp. 5587-5595, vol. 51.

Brach, M. et al, "Ionizing Radiation Induces Expression of Interleukin 6 by Human Fibroblasts Involving Activation of Nuclear Factor-kB," J. Biolog. Chem., Apr. 25, 1993, pp. 8466-8472, vol. 268, No. 12.

(56) References Cited

OTHER PUBLICATIONS

Brooks, B. et al., "CHARMM: The Biomolecular Simulation Program," NIH Public Access Author Manuscript, 124 pgs., J. Comput. Chem., Jul. 30, 2009, pp. 1545-1614, vol. 30, No. 10.
Burg, M. et al., "NG2 Proteoglycan-binding Peptides Target Tumor Neovasculature," Cancer Res., Jun. 15, 1999, pp. 2869-2874, vol. 59.
Cai, X. et al., "Anti-melanoma antibodies from melanoma patients immunized with genetically modified autologous tumor cells: Selection of specific antibodies from single-chain Fv fusion phage libraries," PNAS, Jul. 1995, pp. 6537-6541, vol. 92.
Carpizo, D. et al., "Endogenous regulators of angiogenesis—emphasis on proteins with thrombospondin—type I motifs," Cancer Metastasis Rev., 2000, pp. 159-165, vol. 19, Kluwer Academic Publishers, Netherlands.
Casset, F. et al., "A peptide mimetic of an anti-CD4 monoclonal antibody by rational design," Biochem. Biophys. Res. Commun., 2003, pp. 198-205, vol. 307.
Castellano, M. et al., "CDKN2A/p16 Is Inactivated in Most Melanoma Cell Lines," Cancer Res, 1997, pp. 4868-4875, vol. 57.
Chen, C. et al., "Reactivity of Synthetic Peptide Analogs of Adhesive Proteins in Regard to the Interaction of Human Endothelial Cells With Extracellular Matrix," Blood, May 15, 1991, pp. 2200-2206, vol. 77, No. 10.
Cheresh, D. et al., "Human endothelial cells synthesize and express an Arg-Gly-Asp-directed adhesion receptor involved in attachment to fibrinogen and von Willebrand factor," PNAS, Sep. 1987, pp. 6471-6475, vol. 84.
Chothia, C. et al., "Canonical Structures for the Hypervariable Regions of Immunoglobulins," J. Mol. Biol., 1987, pp. 901-917, vol. 196.
Chothia, C. et al., "Conformations of immunoglobulin hypervariable regions," Nature, Dec. 1989, pp. 877-883, vol. 342.
Clapp, C. et al., "The 16-Kilodalton N-Terminal Fragment of Human Prolactin Is a Potent Inhibitor of Angiogenesis," Endocrinology, Sep. 1993, pp. 1292-1299, vol. 133, No. 3.
Co, M. et al., "Humanized antibodies for antiviral therapy," PNAS, Apr. 1991, pp. 2869-2873, vol. 88.
Collins, M. et al., "Mapping multiprotein complexes by affinity purification and mass spectrometry," Curr. Opin. Biotechnol., 2008, pp. 324-330, vol. 19, No. 4.
Croce, C. et al., "Cloning of human RAD54 gene homolog and its diagnostic and therapeutic uses," Database HCAPLUS on STN, 1998, Abstract EP0844305, Accession No. 1998:365000, Registry No. 208601-90-5 for human rad54 for SEQ ID No. 12, 1 pg.
Dai, C. et al., "p16INK4a Expression Begins Early in Human Colon Neoplasia and Correlates Inversely With Markers of Cell Proliferation," Gastroenterology, 2000, pp. 929-942, vol. 119.
Dameron, K. et al., "The p53 Tumor Suppressor Gene Inhibits Angiogenesis by Stimulating the Production of Thrombospondin," Cold Spring Harbor Symposia on Quantitative Biology, 1994, pp. 483-489, vol. LIX.
De Bree, R. et al., "Selection of monoclonal antibody E48 IgG or U36 IgG for adjuvant radioimmunotherapy in head and neck cancer patients," British J. Cancer, 1997, pp. 1049-1060, vol. 75, No. 7.
Diaz, R. et al., "Determining glioma response to radiation therapy using recombinant peptides," Expert Rev. Anticancer Ther., 2008, pp. 1787-1796, vol. 8, No. 11.

Dimitriadis, G., "Effect of Detergents on Antibody-Antigen Interaction," Anal. Biochem., 1979, pp. 445-451, vol. 98.
Dolganov, G., "The human RAD50 and Septin-2 genes and their roles in myelodysplastic diseases and their diagnostic and therapeutic uses," Database HCAPLUS on STN, 1997, Abstract WO97/27284, Accession No. 1997:513697, Registry No. 194813-18-8 for human clone B15.2, for SEQ ID No. 8, 1 pg.
Donovan, E. et al., "Targeting VEGF in Cancer Therapy," Curr. Probl. Cancer, Jan./Feb. 2006, pp. 7-32, vol. 30.
Edmonds, S., "Antibody-Targeted Chemotherapy with Mylotarg Shows Promise for Many Adults with Deadly Form of Leukemia," American Society of Clinical Oncology 36th Annual Meeting, May 21, 2000, New Orleans, Louisana.
Eijan, A. et al., "Modulation of tumor-induced angiogenesis by proteins of extracellular matrix," Mol. Biother., Mar. 1991, pp. 38-40, vol. 3, No. 1.
Ellerby, H. et al., "Anti-cancer activity of targeted pro-apoptotic peptides," Nature Medicine, Sep. 1999, pp. 1032-1038, vol. 5, No. 9.
Evan, G. et al., "Isolation of Monoclonal Antibodies Specific for Human c-myc Proto-Oncogene Product," Mol. Cell Biol., Dec. 1985, pp. 3610-3616, vol. 5, No. 12.
Fan, Q-W. et al., "Targeting the RTK-PI3K-mTOR Axis in Malignant Glioma: Overcoming Resistance," NIH Public Access Author Manuscript, Jan. 2011, pp. 1-16, published in final edited form as: Curr. Top. Microbiol. Immunol., 2010, pp. 279-296, vol. 347.
Ferlay, J. et al., "Estimates of worldwide burden of cancer in 2008: GLOBOCAN 2008," Int. J. Cancer, 2010, pp. 2893-2917, vol. 127.
Figini, M. et al., "Panning Phage Antibody Libraries on Cells: Isolation of Human Fab Fragments against Ovarian Carcinoma Using Guided Selection," Cancer Res., Mar. 1, 1998, pp. 991-996, vol. 58.
Fox, S. et al., "Markers of tumor angiogenesis: clinical applications in prognosis and anti-angiogenic therapy," Investigational New Drugs, 1997, pp. 15-28, vol. 15.
Franken, N. et al., "Clonogenic assay of cells in vitro," Nat. Protoc., 2006, pp. 2315-2319, vol. 1, No. 5.
GenBank AAD40244.1 dated Jun. 22, 1999.
GenBank AEC23014.1 dated Jul. 17, 2011.
Geradts, J. et al., "Frequent Loss of KAI1 Expression in Squamous and Lymphoid Neoplasms," Am. J. Path., Jun. 1999, pp. 1665-1671, vol. 154, No. 6.
Geradts, J. et al., "Immunohistochemical Detection of the Cyclin-dependent Kinase Inhibitor 2/Multiple Tumor Suppressor Gene 1 (CDKN2/MTS1) Product p16INK4A in Archival Human Solid Tumors: Correlation with Retinoblastoma Protein Expression," Cancer Res., 1995, pp. 6006-6011, vol. 55.
Goldman, C. et al., "Targeted Gene Delivery to Kaposi's Sarcoma Cells via the Fibroblast Growth Factor Receptor," Cancer Res., Apr. 15, 1997, pp. 1447-1451, vol. 57.
Gump, J. et al., "Phosphorylation of p16INK4A Correlates with Cdk4 Association," J. Biol. Chem., Feb. 28, 2003, pp. 6619-6622, vol. 278, No. 9.
Extended European Search Report dated Dec. 8, 2020 from related European Patent Application No. 18751856.8; 10 pgs.
Hallahan, D. et al., "Activation of immune cells and enhanced efficacy of radiotherapy by anti-TIP1 antibodies in cancer," Radiotherapy and Oncology, Apr. 29, 2016, p. S477, vol. 119, Elsevier, Ireland.

* cited by examiner

Synthesized PDZ peptide sequence:
IDQD PSQNPFSEDK TDKG

Localization of designed PDZ peptide in whole human Tip1 protein sequence. (in Blue)

```
         10         20         30         40         50         60
MSYIPGQPVT AVVQRVEIHK LRQGENLILG FSIGGGIDQD PSQNPFSEDK TDKGIYVIRV
         70         80         90        100        110        120
SEGGPAEIAG LQIGDKIMQV NGWDMTMVTH DQARKRLIKR SEEVVRLLVT RQSLQKAVQQ
124
SMLS
```

FIG. 7

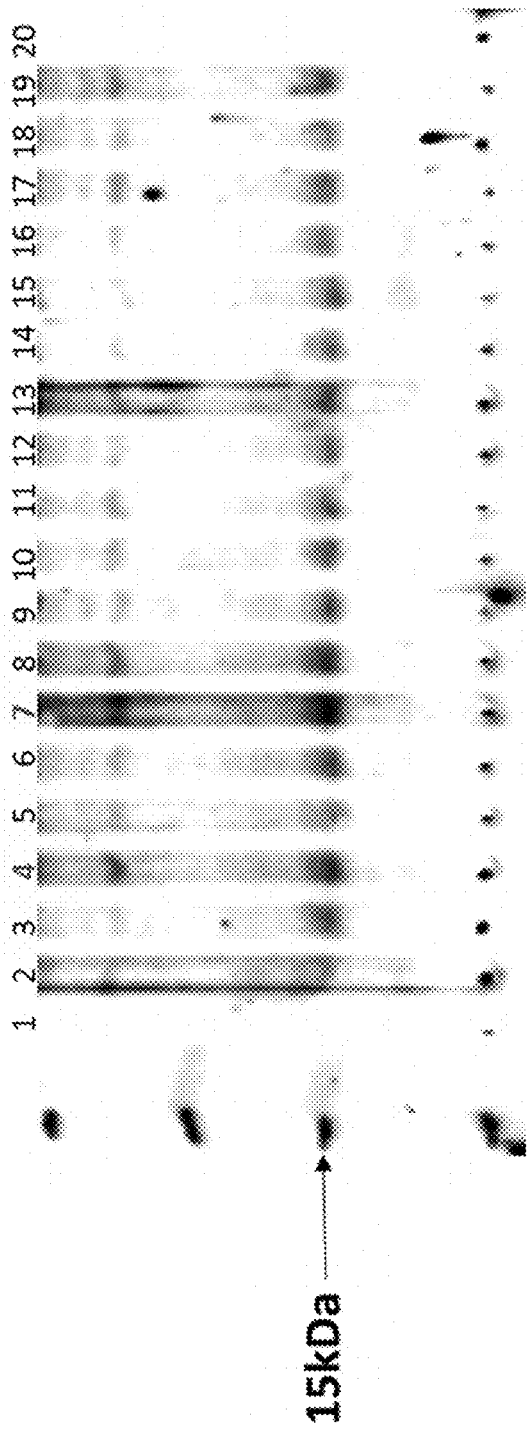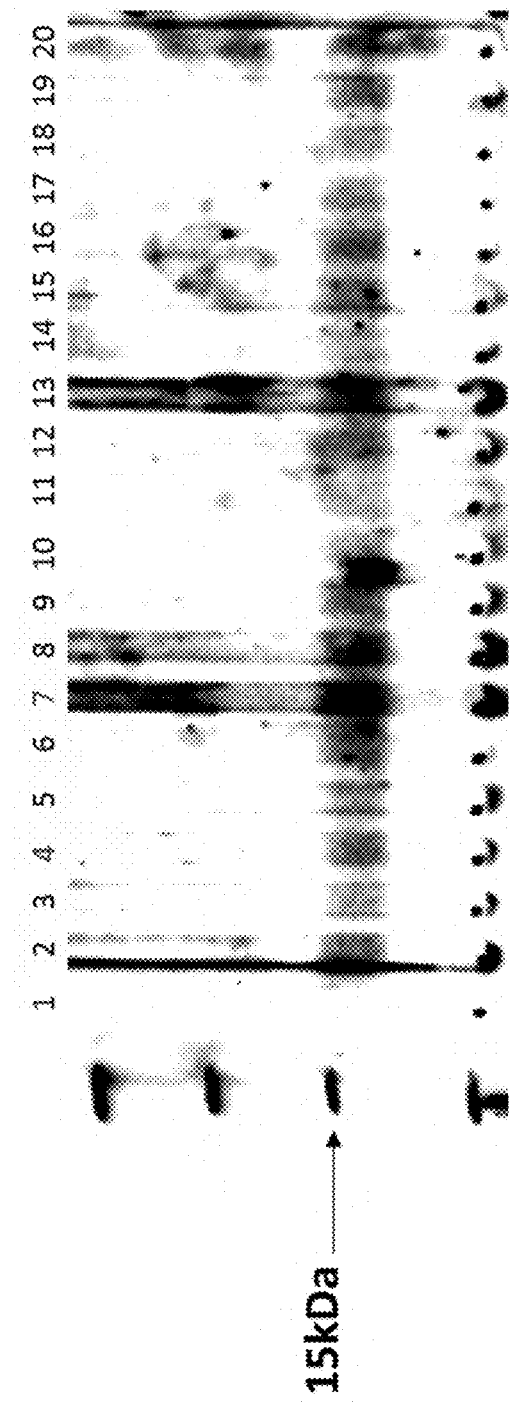
FIG. 10A
FIG. 10B

16h

Day 1

Day 2

Day 3

PDZ peptide ScFv clone G14

CDR analysis VH

----CDR1---> <--CDR2--> <---CDR3----
GFTFSNYA    VSGSGAST    AKHGTRFDYWGQRTLVTVS

CDR analysis VL

----CDR1---> <--CDR2--> <---CDR3----
QSVSSY      GAS         QQT

FIG. 14A

PDZ peptide ScFv clone H2

CDR analysis VH

----CDR1---> <--CDR2--> <---CDR3----
GFTFSNYA    VSGSGAST    AKHGTRFDYWGQRTLVTVS

CDR analysis VL

----CDR1---> <--CDR2--> <---CDR3----
QSVSSY      GAS         QQTYPLTFGRWKIK

FIG. 14B

Affinity of the purified mouse monoclonal
anti-TIP antibodies as detected by Biacore

| Name of mAb | KD | KA |
|---|---|---|
| 7H5 | $1.1 \times 10^{-9}$ | $9.4 \times 10^{8}$ |
| 3D6 | $5.1 \times 10^{-11}$ | $2 \times 10^{10}$ |
| 2F10 | $1.3 \times 10^{-10}$ | $7.5 \times 10^{9}$ |

FIG. 16B

Antibody sequences of 2F10-1 were listed as below:

Heavy chain: DNA sequence (426 bp)

Leader sequence-FR1-CDR1-FR2-CDR2-FR3-CDR3-FR4

ATGGAATGGATCTGGATCTTTCTCTTCATCCTGTCAGGAACTGCAGGTGTCCAATCCCAGGTTCAGC

TGCAGCAGTCTGGAGCTGAGCTGGCGAGGCCTGGGGCTTCAGTGAAGCTGTCCTGCAAGGCTTCTGG

CTACACCTTCACAAGCTCTGGTATAAGCTGGGTGATTCAAAAAACTGGACAGGGCCTTGAGTGGATT

GGAGAGATTTATCCTAGAAGTGGTAATACTTACTACAATGAGAAGTTCAAGGCCAAGGCCGCACTGA

CTGCAGACAAATCCTCCAGCACAGTGCACATGGAGCTCCGCAGCCTGACATCTGAGGACTCTGCGGT

CTATTTCTGTGCAAGATCGAAGACCTACTATAGTAAATACGGAGGGTTTTTGACTACTGGGGCCAA

GGCACCCCTCTCACAGTCTCCTCA

FIG. 17A

Antibody sequences of 2F10-1 were listed as below:

Heavy chain: Amino acids sequence (142 aa)
Leader sequence-FR1-CDR1-FR2-CDR2-FR3-CDR3-FR4
MEWIWIFLFILSGTAGVQSQVQLQQSGAELARPGASVKLSCKASGYTFTSSGISWVIQKTGQGLEWI
GEIYPRSGNTYYNEKFKAKAALTAIKSSSTASMELRSLTSEDSAVYFCARSKTYYSKYGGFFDYWGQ
GTPLTVSS

FIG. 17B

Antibody sequences of 2F10-1 were listed as below:

Light chain: DNA sequence (393 bp)
Leader sequence-FR1-CDR1-FR2-CDR2-FR3-CDR3-FR4
ATGAAGTTGCCTGTTAGGCTGTTGGTGCTGATGTTCTGGATTCCTGCTTCCAGCAGTGATGTTTTGA
TGACCCAAACTCCACTCTCCCTGCCTGTCAGTCTTGGAGATCAAGCCTCCATCTCTTGCAGATCTAG
TCAGAGCATTGTACATGGTAATGGAAACACCTATTTAGAATGGTACCTGCAGAAACCAGGCCAGTCT
CCAAAGCTCCTGATCCACAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCTGGGAGTTTATTACTG
CTTTCAAGGTTCACATGTTCCTCCCACGTTCGGAGGGGGGACCAAGCTGGAAATAAAA

FIG. 17C

Antibody sequences of 2F10-1 were listed as below:

Light chain: Amino acids sequence (131 aa)

Leader sequence-FR1-CDR1-FR2-CDR2-FR3-CDR3-FR4

MKLPVRLLVLMFWIPASSSDVLMTQTPLSLPVSLGDQASISCRSSQSIVHGNGNTYLEWYLQKPGQS
PKLLIHKVSNRFSGVPDRFSGSGSGTDFTLKISRVEAEDLGVYYCFQGSHVPPTFGGGTKLEIK

FIG. 17D

Antibody sequences of 3D6-1 were listed as below:

Heavy chain: DNA sequence (426 bp)

Leader sequence-FR1-CDR1-FR2-CDR2-FR3-CDR3-FR4

ATGGAATGGATCTGGATCTTTCTCTTCATCCTGTCAGGAACTGCAGGTGTCCAATCCCAGGTTCAGT

TGCACCAGTCAGGAGCTGAGCTGGCGAGGCCTGGGGCTGCAGTGAAGCTGACCTGCAAGGCTTCTGG

CTACACCCTCACAAACTCCGGTATAAGCTGGGTGAAGCAGAGATCTGGACAGGGCCTTGAGTGGATT

GGAGAGATTTATCCTGGAAGTGGTAATATTTACTATAATGAGAAGTTCAAGGTCAAGGCCACACTGA

CTGCAGACAAATCCTCCAGTACAACGTACATGGAGCTCCGCAGCCTGACATCTGAGGACTCTGCGGT

CTATTTCTGTGCAAGATCGAGGACCTACTATAGTAAATATGGAGGGCTTTTTGACTACTGGGGCCAG

GGCGCCACTCTCACTGTCTCCTCA

FIG. 18A

Antibody sequences of 3D6-1 were listed as below:

Heavy chain: Amino acids sequence (142 aa)
Leader sequence-FR1-CDR1-FR2-CDR2-FR3-CDR3-FR4
MEWIWIFLFILSGTAGVQSQVQLHQSGAELARPGAAVKLTCKASGYTLTNSGISWVKQRSGQGLEWI
GEIYPGSGNIYYNEKFKVKATLTADKSSSTTYMELRSLTSEDSAVYFCARSRTYYSKYGGLFDYWGQ
GTLTVSS

FIG. 18B

Antibody sequences of 3D6-1 were listed as below:

Light chain: DNA sequence (393 bp)
Leader sequence-FR1-CDR1-FR2-CDR2-FR3-CDR3-FR4

ATGAAGTTGCCTGTTAGGCTGTTGGTGCTGATGTTCTGGATTCCTGGTTCCAACAGTGATGTTTTGA
TGACCCAAACTCCACTCTCCCTGCCTGTCCGTCTTGGAGATCAAGCCTCCATCTCTTGCAGATCTAG
TCAGAGCCTTCTACATAATAATGGAAACACCTATTTAGAATGGTACCTGCAGAAACCAGGCCAGTCT
CCAAAGCTCCTGATCTACAAAGTTTCCAGCCGATTTTCTGGGGTCCCAGACAGGTTCAGTGGCAGTG
GATCAGGGACAGATTTCACACTCAGATCAGCAGAGTGGAGGCTAAGGATCTGGGAGTTTATTACTG
CTTTCAAGGTTCACATATTCCTCCCACGTTCGGAGGGGGGACCAAGCTGGAAATAAAA

FIG. 18C

Antibody sequences of 3D6-1 were listed as below:

Light chain: Amino acids sequence (131 aa)

Leader sequence-FR1-CDR1-FR2-CDR2-FR3-CDR3-FR4

MKLPVRLLVLMFWIPGSNSDVLMTQTPLSLPVRLGDQASISCRSSQSLLHSNGNTYLEWYLQKPGQS
PKLLIYKVSSRFSGVPDRFSGSGSGTDFTLKISRVEAEDLGVYYCFQGSHIPPTFGGGTKLEIK

FIG. 18D

Antibody sequences of 4B12-1 were listed as below:

Heavy chain: DNA sequence (426 bp)

Leader sequence-FR1-CDR1-FR2-CDR2-FR3-CDR3-FR4

ATGGAATGGATCTGGATCTTTCTCTTCATCCTGTCAGGAACTGCAGGTGTCCACTCCCAGGTTTCAAC
TACAGCAGTCTGGAGCTGAGCTGGCGAGGCCTGGGGCTTCAGTGAAGCTGTCCTGCAAGGCTTCTGG
CTACACCTTCACAAGCTATGGTATAAGCTGGGTGAAGCAGAGAACTGGACAGGGCCTTGAGTGGATT
GGAGAGATTTATTTTAGAAGTGGTAATATTTACTACAATGAGAAATTTAAGGGCAAGGCCACACTGA
CTGCAGACAAATCCTCCAGCACAGCGTACATGGAGCTCCGCAGCCTGACATCTGAGGACTCTGCGGT
CTATTTCTGTGCAAGATCGAAGACCTTCTATAGTAACTACGGAGGGGTTTTTGACTACTGGGGCCAA
GGCACCACTCTCACAGTCTCCTCA

FIG. 19A

Antibody sequences of 4B12-1 were listed as below:

Heavy chain: Amino acids sequence (142 aa)
Leader sequence-FR1-CDR1-FR2-CDR2-FR3-CDR3-FR4
MEWIWIFLFILSGTAGVHSQFQLQQSGAELARPGASVKLSCKASGYTFTSYGISWVKQRTGQGLEWI
GEIYPRSGNIYYNEKFKGKATLTADKSSSTAYMELRSLTSEDSAVYFCARSKTFYSNYGGVFDYWGQ
GTTLTVSS

FIG. 19B

Antibody sequences of 4B12-1 were listed as below:

Light chain: DNA sequence (393 bp)
Leader sequence-FR1-CDR1-FR2-CDR2-FR3-CDR3-FR4

ATGAAGTTGCCTGTTAGGCTGTTGGTGCTGATGTTCTGGATTCCTGTTTCCACCTGTGATGTTTTGT
GACCCAAACTCCACTCTCCCTGCCTGTCAGTCTTGGAGATCAAGCCTCCATCTCTTGCAGATCTAG
TCGAGCATTGTTCATAATAATGGAAACACCTATTTAGAATGGTACCTGCAGAAACCAGGCCAGTCT
CCAAAGCTCCTGATCTACAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCTGGGAGTTTATTACTG
CTTTCAAGGTTCACATGTTCCTCCACGTTCGGAGGGGGGACCAGGCTGGAAATAAAA

FIG. 19C

Antibody sequences of 4B12-1 were listed as below:

Light chain: Amino acids sequence (131 aa)
Leader sequence-FR1-CDR1-FR2-CDR2-FR3-CDR3-FR4
MKLPVRLLVLMFWIPVSTCDVLVTQTPLSLPVSLGDQASISCRSSRSIVHNNGNTYLEWYLQKPGQS
PKLLIYKVSNRFSGVPDRFSGSGSGTDFTLKISRVEAEDLGVYYCFQGSHVPPTFGGGTRLEIK

FIG. 19D

Antibody sequences of 7H5-1 were listed as below:

Heavy chain: DNA sequence (426 bp)

Leader sequence-FR1-CDR1-FR2-CDR2-FR3-CDR3-FR4

ATGGAAAGGATCTGGATCTTTCTCTTCATCCTGTCAGGAACTGCAGGTGTCCAATCCCAGGCTCAGC
TGCAGCAGTCTGGAGCTGAACTGGCCAGGCCTGGGGCTTCAGTGAGGCTGTCCTGCAAGGCTTCTGG
CTACATCCTCACAAGTTCTGGTATAAGCTGGGTGAAGCAGAGAACTGGACAGGGCCTTGAGTGGATT
GGAGAGATTTATCCTAGAAGTGGCAATACTTACTACAATGAAGTTCAAGGGCAAGGCCACACTGA
CTGCAGACAAATCCTCCAGTATAGCCTACATGGACCTCCGCACCCTGACATCTGAGGACTCTGCGGT
CTATTTCTGCGCAAGATCGAAGACGTTCTATAGTAAATACGGAGGGGTTTTTGACTACTGGGGCCAA
GGCACCACTCTCACAGTCTCCTCA

FIG. 20A

Antibody sequences of 7H5-1 were listed as below:

Heavy chain: Amino acids sequence (142 aa)

Leader sequence-FR1-CDR1-FR2-CDR2-FR3-CDR3-FR4

MERHWIFLFILSGTAGVQSQAQLQQSGAELARPGASVRLSCRASGYILTSSGISWVKQRTGQGLEWI
GEIYPRSGNTYYNEKFKGKATLTADKSSSIAYMDLRTLTSEDSAVYFCARSKTFYSKYGGVFDYWGQ
GTTLTVSS

FIG. 20B

Antibody sequences of 7H5-1 were listed as below:

Light chain: DNA sequence (393 bp)
Leader sequence-FR1-CDR1-FR2-CDR2-FR3-CDR3-FR4
ATGAAGTTGCCTGTTAGGCTGTTGGTGCTGATGTTCTGGATTCCTGCTTCCAGCAGTGATGTTTTGA
TGACCCAAACTCCACTCTCCCTGCCTGTCAGTCTTGGAGATCAAGCCTCCATCTCTTGCAGATCTAG
TCAGAACATTGTACATAATAATGGAAACACCTATTTAGATTGGTACCTGCAGAAACCAGGCCAGTCT
CCAAAGCTCCTGATCTACAAAGTTTCCAACCGATTTTCGGGGGTCCCAGACAGGTTCAGTGGCAGTG
GATCAGGGACAGATTTCACACTCAAGATCAGCAGAGTGGAGGCTGAGGATCTGGGAGTTTATTACTG
CTTTCAAGGTTCACATGTTCCTCCCACGTTCGGAGGGGGGACCAAGCTGGAAATAAAA

FIG. 20C

Antibody sequences of 7H5-1 were listed as below:

Light chain: Amino acids sequence (131 aa)
Leader sequence-FR1-CDR1-FR2-CDR2-FR3-CDR3-FR4
MKLPVRLLVLMFWIPASSSDVLMTQTPLSLPVSLGDQASISCRSSQNIVHNNGNTYLDWYLQKPGQS
PKLLIYKVSNRFSGVPDRFSGSGSGADFTLKISRVEAEDLGVYYCFQGSHVPPTFGGGTKLEIK

FIG. 20D

SEQUENCE LISTING

<160> NUMBER OF SEQ ID NOS: 53

<210> SEQ ID NO 1
<211> LENGTH: 124
<212> TYPE: PRT
<213> ORGANISM: Homo sapiens

<400> SEQUENCE: 1

Met Ser Tyr Ile Pro Gly Gln Pro Val Thr Ala Val Val Gln Arg Val
1               5                   10                  15

Glu Ile His Lys Leu Arg Gln Gly Glu Asn Leu Ile Leu Gly Phe Ser
            20                  25                  30

Ile Gly Gly Gly Ile Asp Gln Asp Pro Ser Gln Asn Pro Phe Ser Glu
        35                  40                  45

Asp Lys Thr Asp Lys Gly Ile Tyr Val Thr Arg Val Ser Glu Gly Gly
    50                  55                  60

Pro Ala Glu Ile Ala Gly Leu Gln Ile Gly Asp Lys Ile Met Gln Val
65                  70                  75                  80

Asn Gly Trp Asp Met Thr Met Val Thr His Asp Gln Ala Arg Lys Arg
                85                  90                  95

Leu Thr Lys Arg Ser Glu Glu Val Val Arg Leu Leu Val Thr Arg Gln
            100                 105                 110

Ser Leu Gln Lys Ala Val Gln Gln Ser Met Leu Ser
        115                 120

<210> SEQ ID NO 2
<211> LENGTH: 100
<212> TYPE: PRT
<213> ORGANISM: Homo sapiens

<400> SEQUENCE: 2

Val Gln Arg Val Glu Ile His Lys Leu Arg Gln Gly Glu Asn Leu Ile
1               5                   10                  15

Leu Gly Phe Ser Ile Gly Gly Gly Ile Asp Gln Asp Pro Ser Gln Asn
            20                  25                  30

Pro Phe Ser Glu Asp Lys Thr Asp Lys Gly Ile Tyr Val Thr Arg Val
        35                  40                  45

Ser Glu Gly Gly Pro Ala Glu Ile Ala Gly Leu Gln Ile Gly Asp Lys
    50                  55                  60

Ile Met Gln Val Asn Gly Trp Asp Met Thr Met Val Thr His Asp Gln
65                  70                  75                  80

Ala Arg Lys Arg Leu Thr Lys Arg Ser Glu Glu Val Val Arg Leu Leu
                85                  90                  95

Val Thr Arg Gln
            100

<210> SEQ ID NO 3
<211> LENGTH: 18
<212> TYPE: PRT
<213> ORGANISM: Homo sapiens

<400> SEQUENCE: 3

Ile Asp Gln Asp Pro Ser Gln Asn Pro Phe Ser Glu Asp Lys Thr Asp
1               5                   10                  15

Lys Gly

<210> SEQ ID NO 4
<211> LENGTH: 8

```
<212> TYPE: PRT
<213> ORGANISM: Artificial Sequence
<220> FEATURE:
<223> OTHER INFORMATION: Synthesized

<400> SEQUENCE: 4

Gly Phe Thr Phe Ser Asn Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Synthesized

<400> SEQUENCE: 5

Val Ser Gly Ser Gly Ala Ser Thr
1               5

<210> SEQ ID NO 6
<211> LENGTH: 19
<212> TYPE: PRT
<213> ORGANISM: Artificial Sequence
<220> FEATURE:
<223> OTHER INFORMATION: Synthesized

<400> SEQUENCE: 6

Ala Lys His Gly Thr Arg Phe Asp Tyr Trp Gly Gln Arg Thr Leu Val
1               5                   10                  15

Thr Val Ser

<210> SEQ ID NO 7
<211> LENGTH: 6
<212> TYPE: PRT
<213> ORGANISM: Artificial Sequence
<220> FEATURE:
<223> OTHER INFORMATION: Synthesized

<400> SEQUENCE: 7

Gln Ser Val Ser Ser Tyr
1               5

<210> SEQ ID NO 8
<211> LENGTH: 3
<212> TYPE: PRT
<213> ORGANISM: Artificial Sequence
<220> FEATURE:
<223> OTHER INFORMATION: Synthesized

<400> SEQUENCE: 8

Gly Ala Ser
1

<210> SEQ ID NO 9
<211> LENGTH: 3
<212> TYPE: PRT
<213> ORGANISM: Artificial Sequence
<220> FEATURE:
<223> OTHER INFORMATION: Synthesized

<400> SEQUENCE: 9

Gln Gln Thr
1

<210> SEQ ID NO 10
```

```
<211> LENGTH: 14
<212> TYPE: PRT
<213> ORGANISM: Artificial Sequence
<220> FEATURE:
<223> OTHER INFORMATION: Synthesized

<400> SEQUENCE: 10

Gln Gln Thr Tyr Pro Leu Thr Phe Gly Arg Trp Lys Ile Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthesized

<400> SEQUENCE: 11

Ile Asp Gln Asp Pro Ser Gln Asn Pro Phe
1               5                   10

<210> SEQ ID NO 12
<211> LENGTH: 20
<212> TYPE: DNA
<213> ORGANISM: Artificial Sequence
<220> FEATURE:
<223> OTHER INFORMATION: Synthesized

<400> SEQUENCE: 12
ccagggtatt tatgtcacac                                           20

<210> SEQ ID NO 13
<211> LENGTH: 20
<212> TYPE: DNA
<213> ORGANISM: Artificial Sequence
<220> FEATURE:
<223> OTHER INFORMATION: Synthesized

<400> SEQUENCE: 13
cattggaggt ggaatcgacc                                           20

<210> SEQ ID NO 14
<211> LENGTH: 5
<212> TYPE: PRT
<213> ORGANISM: Artificial Sequence
<220> FEATURE:
<223> OTHER INFORMATION: Synthesized

<400> SEQUENCE: 14

Ser Ser Gly Ile Ser
1               5

<210> SEQ ID NO 15
<211> LENGTH: 17
<212> TYPE: PRT
<213> ORGANISM: Artificial Sequence
<220> FEATURE:
<223> OTHER INFORMATION: Synthesized

<400> SEQUENCE: 15

Glu Ile Tyr Pro Arg Ser Gly Asn Thr Tyr Tyr Asn Glu Lys Phe Lys
1               5                   10                  15

Ala

<210> SEQ ID NO 16
<211> LENGTH: 14
```

```
<212> TYPE: PRT
<213> ORGANISM: Artificial Sequence
<220> FEATURE:
<223> OTHER INFORMATION: Synthesized

<400> SEQUENCE: 16

Ser Lys Thr Tyr Tyr Ser Lys Tyr Gly Gly Phe Phe Asp Tyr
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Synthesized

<400> SEQUENCE: 17

Arg Ser Ser Gln Ser Ile Val His Gly Asn Gly Asn Thr Tyr Leu Glu
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Synthesized

<400> SEQUENCE: 18

Val Ser Asn Arg Phe Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthesized

<400> SEQUENCE: 19

Phe Gln Gly Ser His Val Pro Pro Thr
1               5

<210> SEQ ID NO 20
<211> LENGTH: 142
<212> TYPE: PRT
<213> ORGANISM: Artificial Sequence
<220> FEATURE:
<223> OTHER INFORMATION: Synthesized

<400> SEQUENCE: 20

Met Glu Trp Ile Trp Ile Phe Leu Phe Ile Leu Ser Gly Thr Ala Gly
1               5                   10                  15

Val Gln Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Ser Ser Gly Ile Ser Trp Val Ile Gln Lys Thr Gly Gln Gly Leu
    50                  55                  60

Glu Trp Ile Gly Glu Ile Tyr Pro Arg Ser Gly Asn Thr Tyr Tyr Asn
65                  70                  75                  80

Glu Lys Phe Lys Ala Lys Ala Ala Leu Thr Ala Asp Lys Ser Ser Ser
                85                  90                  95

Thr Ala His Met Glu Leu Arg Ser Leu Thr Ser Glu Asp Ser Ala Val
            100                 105                 110
```

```
Tyr Phe Cys Ala Arg Ser Lys Thr Tyr Tyr Ser Lys Tyr Gly Gly Phe
            115                 120                 125

Phe Asp Tyr Trp Gly Gln Gly Thr Pro Leu Thr Val Ser Ser
            130                 135                 140

<210> SEQ ID NO 21
<211> LENGTH: 131
<212> TYPE: PRT
<213> ORGANISM: Artificial Sequence
<220> FEATURE:
<223> OTHER INFORMATION: Synthesized

<400> SEQUENCE: 21

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Gly Asn Gly Asn Thr Tyr Leu Glu Trp Tyr Leu Gln Lys Pro
    50                  55                  60

Gly Gln Ser Pro Lys Leu Leu Ile His Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Pro Thr Phe Gly Gly Gly Thr Lys Leu
        115                 120                 125

Glu Ile Lys
    130

<210> SEQ ID NO 22
<211> LENGTH: 426
<212> TYPE: PRT
<213> ORGANISM: Artificial Sequence
<220> FEATURE:
<223> OTHER INFORMATION: Synthesized

<400> SEQUENCE: 22

Ala Thr Gly Gly Ala Ala Thr Gly Gly Ala Thr Cys Thr Gly Gly Ala
1               5                   10                  15

Thr Cys Thr Thr Thr Cys Thr Cys Thr Thr Cys Ala Thr Cys Cys Thr
            20                  25                  30

Gly Thr Cys Ala Gly Gly Ala Ala Cys Thr Gly Cys Ala Gly Gly Thr
        35                  40                  45

Gly Thr Cys Cys Ala Ala Thr Cys Cys Cys Ala Gly Gly Thr Thr Cys
    50                  55                  60

Ala Gly Cys Thr Gly Cys Ala Gly Cys Ala Gly Thr Cys Thr Gly Gly
65                  70                  75                  80

Ala Gly Cys Thr Gly Ala Gly Cys Thr Gly Gly Cys Gly Ala Gly Gly
                85                  90                  95

Cys Cys Thr Gly Gly Gly Cys Thr Thr Cys Ala Gly Thr Gly Ala Ala
            100                 105                 110

Ala Gly Cys Thr Gly Thr Cys Cys Thr Gly Cys Ala Ala Gly Gly Cys
        115                 120                 125

Thr Thr Cys Thr Gly Gly Cys Thr Ala Cys Ala Cys Cys Thr Thr Cys
```

```
130 135 140

Ala Cys Ala Ala Gly Cys Thr Cys Thr Gly Gly Thr Ala Thr Ala Ala
145 150 155 160

Gly Cys Thr Gly Gly Gly Thr Gly Ala Thr Thr Cys Ala Ala Ala Ala
165 170 175

Ala Ala Cys Thr Gly Gly Ala Cys Ala Gly Gly Gly Cys Cys Thr Thr
180 185 190

Gly Ala Gly Thr Gly Gly Ala Thr Thr Gly Gly Ala Gly Ala Gly Ala
195 200 205

Thr Thr Thr Ala Thr Cys Cys Thr Ala Gly Ala Ala Gly Thr Gly Gly
210 215 220

Thr Ala Ala Thr Ala Cys Thr Thr Ala Cys Thr Ala Cys Ala Ala Thr
225 230 235 240

Gly Ala Gly Ala Ala Gly Thr Thr Cys Ala Ala Gly Gly Cys Cys Ala
245 250 255

Ala Gly Gly Cys Cys Gly Cys Ala Cys Thr Gly Ala Cys Thr Gly Cys
260 265 270

Ala Gly Ala Cys Ala Ala Ala Thr Cys Cys Thr Cys Cys Ala Gly Cys
275 280 285

Ala Cys Ala Gly Cys Gly Cys Ala Cys Ala Thr Gly Gly Ala Gly Cys
290 295 300

Thr Cys Cys Gly Cys Ala Gly Cys Cys Thr Gly Ala Cys Ala Thr Cys
305 310 315 320

Thr Gly Ala Gly Gly Ala Cys Thr Cys Thr Gly Cys Gly Gly Thr Cys
325 330 335

Thr Ala Thr Thr Thr Cys Thr Gly Thr Gly Cys Ala Ala Gly Ala Thr
340 345 350

Cys Gly Ala Ala Gly Ala Cys Cys Thr Ala Cys Thr Ala Thr Ala Gly
355 360 365

Thr Ala Ala Ala Thr Ala Cys Gly Gly Ala Gly Gly Gly Thr Thr Thr
370 375 380

Thr Thr Thr Gly Ala Cys Thr Ala Cys Thr Gly Gly Gly Gly Cys Cys
385 390 395 400

Ala Ala Gly Gly Cys Ala Cys Cys Cys Cys Thr Cys Thr Cys Ala Cys
405 410 415

Ala Gly Thr Cys Thr Cys Cys Thr Cys Ala
420 425

<210> SEQ ID NO 23
<211> LENGTH: 393
<212> TYPE: PRT
<213> ORGANISM: Artificial Sequence
<220> FEATURE:
<223> OTHER INFORMATION: Synthesized

<400> SEQUENCE: 23

Ala Thr Gly Ala Ala Gly Thr Thr Gly Cys Cys Thr Gly Thr Thr Ala
1 5 10 15

Gly Gly Cys Thr Gly Thr Thr Gly Gly Thr Gly Cys Thr Gly Ala Thr
20 25 30

Gly Thr Thr Cys Thr Gly Gly Ala Thr Thr Cys Cys Thr Gly Cys Thr
35 40 45

Thr Cys Cys Ala Gly Cys Ala Gly Thr Gly Ala Thr Gly Thr Thr Thr
50 55 60

Thr Gly Ala Thr Gly Ala Cys Cys Cys Ala Ala Ala Cys Thr Cys Cys

```
             65                  70                  75                  80
Ala Cys Thr Cys Thr Cys Cys Thr Gly Cys Cys Thr Gly Thr Cys
                    85                  90                  95

Ala Gly Thr Cys Thr Thr Gly Gly Ala Gly Ala Thr Cys Ala Ala Gly
                100                 105                 110

Cys Cys Thr Cys Cys Ala Thr Cys Thr Cys Thr Thr Gly Cys Ala Gly
                115                 120                 125

Ala Thr Cys Thr Ala Gly Thr Cys Ala Gly Ala Gly Cys Ala Thr Thr
                130                 135                 140

Gly Thr Ala Cys Ala Thr Gly Thr Ala Ala Thr Gly Gly Ala Ala
145                 150                 155                 160

Ala Cys Ala Cys Thr Ala Thr Thr Ala Gly Ala Ala Thr Gly
                165                 170                 175

G

```
<213> ORGANISM: Artificial Sequence
<220> FEATURE:
<223> OTHER INFORMATION: Synthesized

<400> SEQUENCE: 25

Glu Ile Tyr Pro Gly Ser Gly Asn Ile Tyr Tyr Asn Glu Lys Phe Lys
1               5                   10                  15

Val

<210> SEQ ID NO 26
<211> LENGTH: 14
<212> TYPE: PRT
<213> ORGANISM: Artificial Sequence
<220> FEATURE:
<223> OTHER INFORMATION: Synthesized

<400> SEQUENCE: 26

Ser Arg Thr Tyr Tyr Ser Lys Tyr Gly Gly Leu Phe Asp Tyr
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Synthesized

<400> SEQUENCE: 27

Arg Ser Ser Gly Ser Leu Leu His Asn Asn Gly Asn Thr Tyr Leu Glu
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Synthesized

<400> SEQUENCE: 28

Lys Val Ser Ser Arg Phe Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthesized

<400> SEQUENCE: 29

Phe Gln Gly Ser His Ile Pro Pro Thr
1               5

<210> SEQ ID NO 30
<211> LENGTH: 142
<212> TYPE: PRT
<213> ORGANISM: Artificial Sequence
<220> FEATURE:
<223> OTHER INFORMATION: Synthesized

<400> SEQUENCE: 30

Met Glu Trp Ile Trp Ile Phe Leu Phe Ile Leu Ser Gly Thr Ala Gly
1               5                   10                  15

Val Gln Ser Gln Val Gln Leu His Gln Ser Gly Ala Glu Leu Ala Arg
            20                  25                  30
```

Pro Gly Ala Ala Val Lys Leu Thr Cys Lys Ala Ser Gly Tyr Thr Leu
              35                  40                  45

Thr Asn Ser Gly Ile Ser Trp Val Lys Gln Arg Ser Gly Gln Gly Leu
 50                  55                  60

Glu Trp Ile Gly Glu Ile Tyr Pro Gly Ser Gly Asn Ile Tyr Tyr Asn
 65                  70                  75                  80

Glu Lys Phe Lys Val Lys Ala Thr Leu Thr Ala Asp Lys Ser Ser Ser
                 85                  90                  95

Thr Thr Tyr Met Glu Leu Arg Ser Leu Thr Ser Glu Asp Ser Ala Val
                100                 105                 110

Tyr Phe Cys Ala Arg Ser Arg Thr Tyr Tyr Ser Lys Tyr Gly Gly Leu
                115                 120                 125

Phe Asp Tyr Trp Gly Gln Gly Ala Thr Leu Thr Val Ser Ser
            130                 135                 140

<210> SEQ ID NO 31
<211> LENGTH: 131
<212> TYPE: PRT
<213> ORGANISM: Artificial Sequence
<220> FEATURE:
<223> OTHER INFORMATION: Synthesized

<400> SEQUENCE: 31

Met Lys Leu Pro Val Arg Leu Leu Val Leu Met Phe Trp Ile Pro Gly
 1               5                  10                  15

Ser Asn Ser Asp Val Leu Met Thr Gln Thr Pro Leu Ser Leu Pro Val
                 20                  25                  30

Arg Leu Gly Asp Gln Ala Ser Ile Ser Cys Arg Ser Ser Gln Ser Leu
             35                  40                  45

Leu His Asn Asn Gly Asn Thr Tyr Leu Glu Trp Tyr Leu Gln Lys Pro
 50                  55                  60

Gly Gln Ser Pro Lys Leu Leu Ile Tyr Lys Val Ser Ser Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Lys Asp Leu Gly Val Tyr Tyr Cys
                100                 105                 110

Phe Gln Gly Ser His Ile Pro Pro Thr Phe Gly Gly Gly Thr Lys Leu
                115                 120                 125

Glu Ile Lys
    130

<210> SEQ ID NO 32
<211> LENGTH: 426
<212> TYPE: PRT
<213> ORGANISM: Artificial Sequence
<220> FEATURE:
<223> OTHER INFORMATION: Synthesize

<400> SEQUENCE: 32

Ala Thr Gly Gly Ala Ala Thr Gly Gly Ala Thr Cys Thr Gly Gly Ala
 1               5                  10                  15

Thr Cys Thr Thr Thr Cys Thr Cys Thr Thr Cys Ala Thr Cys Cys Thr
                 20                  25                  30

Gly Thr Cys Ala Gly Gly Ala Ala Cys Thr Gly Cys Ala Gly Gly Thr
             35                  40                  45

Gly Thr Cys Cys Ala Ala Thr Cys Cys Cys Ala Gly Gly Thr Thr Cys
 50                  55                  60

Ala Gly Thr Thr Gly Cys Ala Cys Cys Ala Gly Thr Cys Ala Gly Gly
65                  70                  75                  80

Ala Gly Cys Thr Gly Ala Gly Cys Thr Gly Cys Gly Ala Gly Gly
            85                  90                  95

Cys Cys Thr Gly Gly Gly Cys Thr Gly Cys Ala Gly Thr Gly Ala
            100                 105                 110

Ala Gly Cys Thr Gly Ala Cys Cys Thr Gly Cys Ala Ala Gly Gly Cys
            115                 120                 125

Thr Thr Cys Thr Gly Gly Cys Thr Ala Cys Ala Cys Cys Thr Cys
130                 135                 140

Ala Cys Ala Ala Ala Cys Thr Cys Cys Gly Gly Thr Ala Thr Ala Ala
145                 150                 155                 160

Gly Cys Thr Gly Gly Thr Gly Ala Ala Gly Cys Ala Gly Ala Gly
            165                 170                 175

Ala Thr Cys Thr Gly Gly Ala Cys Ala Gly Gly Cys Cys Thr Thr
            180                 185                 190

Gly Ala Gly Thr Gly Gly Ala Thr Gly Gly Ala Gly Ala Gly Ala
            195                 200                 205

Thr Thr Thr Ala Thr Cys Cys Thr Gly Gly Ala Ala Gly Thr Gly Gly
210                 215                 220

Thr Ala Ala Thr Ala Thr Thr Ala Cys Thr Ala Thr Ala Ala Thr
225                 230                 235                 240

Gly Ala Gly Ala Ala Gly Thr Thr Cys Ala Ala Gly Gly Thr Cys Ala
            245                 250                 255

Ala Gly Gly Cys Cys Ala Cys Ala Cys Thr Gly Ala Cys Thr Gly Cys
            260                 265                 270

Ala Gly Ala Cys Ala Ala Ala Thr Cys Cys Thr Cys Cys Ala Gly Thr
            275                 280                 285

Ala Cys Ala Ala Cys Gly Thr Ala Cys Ala Gly Gly Ala Gly Cys
290                 295                 300

Thr Cys Cys Gly Cys Ala Gly Cys Cys Thr Gly Ala Cys Ala Thr Cys
305                 310                 315                 320

Thr Gly Ala Gly Gly Ala Cys Thr Cys Thr Gly Cys Gly Gly Thr Cys
            325                 330                 335

Thr Ala Thr Thr Thr Cys Thr Gly Thr Gly Cys Ala Ala Gly Ala Thr
            340                 345                 350

Cys Gly Ala Gly Gly Ala Cys Cys Thr Ala Cys Thr Ala Thr Ala Gly
            355                 360                 365

Thr Ala Ala Thr Ala Thr Gly Gly Ala Gly Gly Gly Cys Thr Thr
            370                 375                 380

Thr Thr Thr Gly Ala Cys Thr Ala Cys Thr Gly Gly Gly Gly Cys Cys
385                 390                 395                 400

Ala Gly Gly Gly Cys Gly Cys Cys Cys Thr Cys Thr Cys Ala Cys
            405                 410                 415

Thr Gly Thr Cys Thr Cys Cys Thr Cys Ala
            420                 425

<210> SEQ ID NO 33
<211> LENGTH: 393
<212> TYPE: PRT
<213> ORGANISM: Artificial Sequence
<220> FEATURE:
<223> OTHER INFORMATION: Synthesized

<400> SEQUENCE: 33

-continued

```
Ala Thr Gly Ala Ala Gly Thr Gly Cys Cys Thr Gly Thr Thr Ala
1               5                   10                  15

Gly Gly Cys Thr Gly Thr Thr Gly Thr Gly Cys Thr Gly Ala Thr
            20                  25                  30

Gly Thr Thr Cys Thr Gly Gly Ala Thr Thr Cys Cys Thr Gly Gly Thr
        35                  40                  45

Thr Cys Cys Ala Ala Cys Ala Gly Thr Gly Ala Gly Thr Thr Thr
    50                  55                  60

Thr Gly Ala Thr Gly Ala Cys Cys Cys Ala Ala Cys Thr Cys Cys
65              70                  75                  80

Ala Cys Thr Cys Thr Cys Cys Thr Gly Cys Cys Thr Gly Thr Cys
                85                  90                  95

Cys Gly Thr Cys Thr Thr Gly Gly Ala Gly Ala Thr Cys Ala Ala Gly
                100                 105                 110

Cys Cys Thr Cys Cys Ala Thr Cys Thr Cys Thr Thr Gly Cys Ala Gly
        115                 120                 125

Ala Thr Cys Thr Ala Gly Thr Cys Ala Gly Ala Gly Cys Cys Thr Thr
    130                 135                 140

Cys Thr Ala Cys Ala Thr Ala Ala Thr Ala Ala Thr Gly Gly Ala Ala
145                 150                 155                 160

Ala Cys Ala Cys Cys Thr Ala Thr Thr Thr Ala Gly Ala Ala Thr Gly
                165                 170                 175

Gly Thr Ala Cys Cys Thr Gly Cys Ala Gly Ala Ala Ala Cys Cys Ala
        180                 185                 190

Gly Gly Cys Cys Ala Gly Thr Cys Thr Cys Cys Ala Ala Ala Gly Cys
        195                 200                 205

Thr Cys Cys Thr Gly Ala Thr Cys Thr Ala Cys Ala Ala Ala Gly Thr
210                 215                 220

Thr Thr Cys Cys Ala Gly Cys Cys Gly Ala Thr Thr Thr Thr Cys Thr
225                 230                 235                 240

Gly Gly Gly Gly Thr Cys Cys Ala Gly Ala Cys Ala Gly Gly Thr
                245                 250                 255

Thr Cys Ala Gly Thr Gly Gly Cys Ala Gly Thr Gly Gly Ala Thr Cys
        260                 265                 270

Ala Gly Gly Gly Ala Cys Ala Gly Ala Thr Thr Thr Cys Ala Cys Ala
    275                 280                 285

Cys Thr Cys Ala Ala Gly Ala Thr Cys Ala Gly Cys Ala Gly Ala
        290                 295                 300

Thr Gly Gly Ala Gly Gly Cys Thr Ala Ala Gly Gly Ala Thr Cys Thr
305                 310                 315                 320

Gly Gly Gly Ala Gly Thr Thr Thr Ala Thr Thr Ala Cys Thr Gly Cys
                325                 330                 335

Thr Thr Thr Cys Ala Ala Gly Gly Thr Thr Cys Ala Cys Ala Thr Ala
            340                 345                 350

Thr Thr Cys Cys Thr Cys Cys Cys Ala Cys Gly Thr Thr Cys Gly Gly
            355                 360                 365

Ala Gly Gly Gly Gly Gly Ala Cys Cys Ala Ala Gly Cys Thr Gly
    370                 375                 380

Gly Ala Ala Ala Thr Ala Ala Ala
385                 390
```

<210> SEQ ID NO 34
<211> LENGTH: 5

```
<212> TYPE: PRT
<213> ORGANISM: Artificial Sequence
<220> FEATURE:
<223> OTHER INFORMATION: Synthesized

<400> SEQUENCE: 34

Ser Ser Gly Ile Ser
1               5

<210> SEQ ID NO 35
<211> LENGTH: 17
<212> TYPE: PRT
<213> ORGANISM: Artificial Sequence
<220> FEATURE:
<223> OTHER INFORMATION: Synthesized

<400> SEQUENCE: 35

Glu Ile Tyr Pro Arg Ser Gly Asn Thr Tyr Tyr Asn Glu Lys Phe Lys
1               5                   10                  15

Gly

<210> SEQ ID NO 36
<211> LENGTH: 15
<212> TYPE: PRT
<213> ORGANISM: Artificial Sequence
<220> FEATURE:
<223> OTHER INFORMATION: Synthesized

<400> SEQUENCE: 36

Ser Lys Thr Phe Tyr Ser Lys Tyr Gly Gly Val Phe Asp Tyr Trp
1               5                   10                  15

<210> SEQ ID NO 37
<211> LENGTH: 48
<212> TYPE: PRT
<213> ORGANISM: Artificial Sequence
<220> FEATURE:
<223> OTHER INFORMATION: Synthesized

<400> SEQUENCE: 37

Ala Gly Ala Thr Cys Thr Ala Gly Thr Cys Ala Gly Ala Ala Cys Ala
1               5                   10                  15

Thr Thr Gly Thr Ala Cys Ala Thr Ala Ala Thr Ala Ala Thr Gly Gly
            20                  25                  30

Ala Ala Ala Cys Ala Cys Cys Thr Ala Thr Thr Thr Ala Gly Ala Thr
            35                  40                  45

<210> SEQ ID NO 38
<211> LENGTH: 21
<212> TYPE: PRT
<213> ORGANISM: Artificial Sequence
<220> FEATURE:
<223> OTHER INFORMATION: Synthesized

<400> SEQUENCE: 38

Ala Ala Ala Gly Thr Thr Thr Cys Cys Ala Ala Cys Cys Gly Ala Thr
1               5                   10                  15

Thr Thr Thr Cys Gly
            20

<210> SEQ ID NO 39
<211> LENGTH: 27
<212> TYPE: PRT
<213> ORGANISM: Artificial Sequence
<220> FEATURE:
```

<223> OTHER INFORMATION: Synthesized

<400> SEQUENCE: 39

```
Thr Thr Thr Cys Ala Ala Gly Gly Thr Thr Cys Ala Cys Ala Thr Gly
1               5                   10                  15

Thr Thr Cys Cys Thr Cys Cys Ala Cys Gly
            20                  25
```

<210> SEQ ID NO 40
<211> LENGTH: 142
<212> TYPE: PRT
<213> ORGANISM: Artificial Sequence
<220> FEATURE:
<223> OTHER INFORMATION: Synthesized

<400> SEQUENCE: 40

```
Met Glu Arg Ile Trp Ile Phe Leu Phe Ile Leu Ser Gly Thr Ala Gly
1               5                   10                  15

Val Gln Ser Gln Ala Gln Leu Gln Gln Ser Gly Ala Glu Leu Ala Arg
            20                  25                  30

Pro Gly Ala Ser Val Arg Leu Ser Cys Lys Ala Ser Gly Tyr Ile Leu
        35                  40                  45

Thr Ser Ser Gly Ile Ser Trp Val Lys Gln Arg Thr Gly Gln Gly Leu
    50                  55                  60

Glu Trp Ile Gly Glu Ile Tyr Pro Arg Ser Gly Asn Thr Tyr Tyr Asn
65                  70                  75                  80

Glu Lys Phe Lys Gly Lys Ala Thr Leu Thr Ala Asp Lys Ser Ser Ser
                85                  90                  95

Ile Ala Tyr Met Asp Leu Arg Thr Leu Thr Ser Glu Asp Ser Ala Val
            100                 105                 110

Tyr Phe Cys Ala Arg Ser Lys Thr Phe Tyr Ser Lys Tyr Gly Gly Val
        115                 120                 125

Phe Asp Tyr Trp Gly Gln Gly Thr Thr Leu Thr Val Ser Ser
    130                 135                 140
```

<210> SEQ ID NO 41
<211> LENGTH: 131
<212> TYPE: PRT
<213> ORGANISM: Artificial Sequence
<220> FEATURE:
<223> OTHER INFORMATION: Synthesized

<400> SEQUENCE: 41

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Asn Ile
        35                  40                  45

Val His Asn Asn Gly Asn Thr Tyr Leu Asp Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Ala Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Pro Thr Phe Gly Gly Gly Thr Lys Leu
```

```
              115                 120                 125

Glu Ile Lys
    130

<210> SEQ ID NO 42
<211> LENGTH: 426
<212> TYPE: PRT
<213> ORGANISM: Artificial Sequence
<220> FEATURE:
<223> OTHER INFORMATION: Synthesized

<400> SEQUENCE: 42

Ala Thr Gly Gly Ala Ala Gly Gly Ala Thr Cys Thr Gly Ala
1               5                   10                  15

Thr Cys Thr Thr Thr Cys Thr Cys Thr Thr Cys Ala Thr Cys Cys Thr
                20                  25                  30

Gly Thr Cys Ala Gly Gly Ala Ala Cys Thr Gly Cys Ala Gly Gly Thr
                35                  40                  45

Gly Thr Cys Cys Ala Ala Thr Cys Cys Ala Gly Gly Cys Thr Gly Cys
            50                  55                  60

Ala Gly Cys Thr Gly Cys Ala Gly Cys Ala Gly Thr Cys Thr Gly Gly
65                  70                  75                  80

Ala Gly Cys Thr Gly Ala Ala Cys Thr Gly Gly Cys Gly Ala Gly Gly
                85                  90                  95

Cys Cys Thr Gly Gly Gly Cys Thr Thr Cys Ala Gly Thr Gly Ala
                100                 105                 110

Gly Gly Cys Thr Gly Thr Cys Cys Thr Gly Cys Ala Ala Gly Gly Cys
                115                 120                 125

Thr Thr Cys Thr Gly Gly Cys Thr Ala Cys Ala Cys Cys Thr Cys
            130                 135                 140

Ala Cys Ala Ala Gly Thr Thr Cys Thr Gly Gly Thr Ala Thr Ala Ala
145                 150                 155                 160

Gly Cys Thr Gly Gly Gly Thr Gly Ala Ala Gly Cys Ala Gly Ala Gly
                165                 170                 175

Ala Ala Cys Thr Gly Gly Ala Cys Ala Gly Gly Cys Cys Thr Thr
                180                 185                 190

Gly Ala Gly Thr Gly Gly Ala Thr Thr Gly Gly Ala Gly Ala Gly Ala
                195                 200                 205

Thr Thr Thr Ala Thr Cys Cys Thr Ala Gly Ala Ala Gly Thr Gly Gly
            210                 215                 220

Cys Ala Ala Thr Ala Cys Thr Ala Cys Thr Ala Cys Ala Ala Thr
225                 230                 235                 240

Gly Ala Gly Ala Ala Gly Thr Thr Cys Ala Ala Gly Gly Gly Cys Ala
                245                 250                 255

Ala Gly Gly Cys Cys Ala Cys Ala Cys Thr Gly Ala Cys Thr Gly Cys
                260                 265                 270

Ala Gly Ala Cys Ala Ala Ala Thr Cys Cys Thr Cys Cys Ala Gly Thr
                275                 280                 285

Ala Thr Ala Gly Cys Gly Thr Ala Cys Ala Thr Gly Gly Ala Cys Cys
                290                 295                 300

Thr Cys Cys Gly Cys Ala Cys Cys Cys Thr Gly Ala Cys Ala Thr Cys
305                 310                 315                 320

Thr Gly Ala Gly Gly Ala Cys Thr Cys Thr Gly Cys Gly Gly Thr Cys
                325                 330                 335

Thr Ala Thr Thr Thr Cys Thr Gly Cys Gly Cys Ala Ala Gly Ala Thr
```

```
                340             345             350
Cys Gly Ala Ala Gly Ala Cys Gly Thr Thr Cys Thr Ala Thr Ala Gly
            355             360             365

Thr Ala Ala Ala Thr Ala Cys Gly Gly Ala Gly Gly Gly Thr Thr
370             375             380

Thr Thr Thr Gly Ala Cys Thr Ala Cys Thr Gly Gly Gly Cys Cys
385             390             395             400

Ala Ala Gly Gly Cys Ala Cys Cys Ala Cys Thr Cys Thr Cys Ala Cys
                405             410             415

Ala Gly Thr Cys Thr Cys Cys Thr Cys Ala
            420             425

<210> SEQ ID NO 43
<211> LENGTH: 393
<212> TYPE: PRT
<213> ORGANISM: Artificial Sequence
<220> FEATURE:
<223> OTHER INFORMATION: Synthesized

<400> SEQUENCE: 43

Ala Thr Gly Ala Ala Gly Thr Thr Gly Cys Cys Thr Gly Thr Thr Ala
1               5               10              15

Gly Gly Cys Thr Gly Thr Thr Gly Thr Gly Cys Thr Gly Ala Thr
            20              25              30

Gly Thr Thr Cys Thr Gly Ala Thr Thr Cys Cys Thr Gly Cys Thr
            35              40              45

Thr Cys Cys Ala Gly Cys Ala Gly Thr Gly Ala Thr Thr Thr Thr
50              55              60

Thr Gly Ala Thr Gly Ala Cys Cys Ala Ala Cys Thr Cys Cys
65                  70              75              80

Ala Cys Thr Cys Thr Cys Cys Thr Gly Cys Cys Thr Gly Thr Cys
                85              90              95

Ala Gly Thr Cys Thr Thr Gly Gly Ala Gly Ala Thr Cys Ala Ala Gly
            100             105             110

Cys Cys Thr Cys Cys Ala Thr Cys Thr Cys Thr Thr Gly Cys Ala Gly
                115             120             125

Ala Thr Cys Thr Ala Gly Thr Cys Ala Gly Ala Ala Cys Ala Thr Thr
            130             135             140

Gly Thr Ala Cys Ala Thr Ala Ala Thr Ala Thr Gly Gly Ala Ala
145             150             155             160

Ala Cys Ala Cys Cys Thr Ala Thr Thr Ala Gly Ala Thr Thr Gly
                165             170             175

Gly Thr Ala Cys Cys Thr Gly Cys Ala Gly Ala Ala Cys Cys Ala
            180             185             190

Gly Gly Cys Cys Ala Gly Thr Cys Thr Cys Ala Ala Ala Gly Cys
            195             200             205

Thr Cys Cys Thr Gly Ala Thr Cys Thr Ala Cys Ala Ala Ala Gly Thr
                210             215             220

Thr Thr Cys Cys Ala Ala Cys Cys Gly Ala Thr Thr Thr Thr Cys Gly
225             230             235             240

Gly Gly Gly Gly Thr Cys Cys Cys Ala Gly Ala Cys Ala Gly Gly Thr
                245             250             255

Thr Cys Ala Gly Thr Gly Gly Cys Ala Gly Thr Gly Gly Ala Thr Cys
            260             265             270

Ala Gly Gly Gly Gly Cys Ala Gly Ala Thr Thr Thr Cys Ala Cys Ala
```

```
              275                 280                 285
Cys Thr Cys Ala Ala Gly Ala Thr Cys Ala Gly Cys Ala Gly Ala Gly
        290                 295                 300

Thr Gly Gly Ala Gly Gly Cys Thr Gly Ala Gly Gly Ala Thr Cys Thr
305                 310                 315                 320

Gly Gly Gly Ala Gly Thr Thr Ala Thr Thr Ala Cys Thr Gly Cys
                325                 330                 335

Thr Thr Thr Cys Ala Ala Gly Gly Thr Thr Cys Ala Cys Ala Thr Gly
                340                 345                 350

Thr Thr Cys Cys Thr Cys Cys Cys Ala Cys Gly Thr Thr Cys Gly Gly
                355                 360                 365

Ala Gly Gly Gly Gly Gly Ala Cys Cys Ala Ala Gly Cys Thr Gly
        370                 375                 380

Gly Ala Ala Ala Thr Ala Ala Ala
385                 390

<210> SEQ ID NO 44
<211> LENGTH: 5
<212> TYPE: PRT
<213> ORGANISM: Artificial Sequence
<220> FEATURE:
<223> OTHER INFORMATION: Synthesized

<400> SEQUENCE: 44

Ser Tyr Gly Ile Ser
1               5

<210> SEQ ID NO 45
<211> LENGTH: 17
<212> TYPE: PRT
<213> ORGANISM: Artificial Sequence
<220> FEATURE:
<223> OTHER INFORMATION: Synthesized

<400> SEQUENCE: 45

Glu Ile Tyr Phe Arg Ser Gly Asn Ile Tyr Tyr Asn Glu Lys Phe Lys
1               5                   10                  15

Gly

<210> SEQ ID NO 46
<211> LENGTH: 14
<212> TYPE: PRT
<213> ORGANISM: Artificial Sequence
<220> FEATURE:
<223> OTHER INFORMATION: Synthesized

<400> SEQUENCE: 46

Ser Lys Thr Phe Tyr Ser Asn Tyr Gly Gly Val Phe Asp Tyr
1               5                   10

<210> SEQ ID NO 47
<211> LENGTH: 48
<212> TYPE: PRT
<213> ORGANISM: Artificial Sequence
<220> FEATURE:
<223> OTHER INFORMATION: Synthesized

<400> SEQUENCE: 47

Ala Gly Ala Thr Cys Thr Ala Gly Thr Cys Gly Gly Ala Gly Cys Ala
1               5                   10                  15

Thr Thr Gly Thr Thr Cys Ala Thr Ala Ala Thr Ala Ala Thr Gly Gly
                20                  25                  30
```

Ala Ala Ala Cys Ala Cys Cys Thr Ala Thr Thr Ala Gly Ala Ala
    35                  40                  45

<210> SEQ ID NO 48
<211> LENGTH: 21
<212> TYPE: PRT
<213> ORGANISM: Artificial Sequence
<220> FEATURE:
<223> OTHER INFORMATION: Synthesized

<400> SEQUENCE: 48

Ala Ala Ala Gly Thr Thr Thr Cys Cys Ala Cys Cys Gly Ala Thr
1               5                   10                  15

Thr Thr Thr Cys Thr
            20

<210> SEQ ID NO 49
<211> LENGTH: 27
<212> TYPE: PRT
<213> ORGANISM: Artificial Sequence
<220> FEATURE:
<223> OTHER INFORMATION: Synthesized

<400> SEQUENCE: 49

Thr Thr Thr Cys Ala Ala Gly Gly Thr Thr Cys Ala Cys Ala Thr Gly
1               5                   10                  15

Thr Thr Cys Cys Thr Cys Cys Ala Cys Gly
            20                  25

<210> SEQ ID NO 50
<211> LENGTH: 142
<212> TYPE: PRT
<213> ORGANISM: Artificial Sequence
<220> FEATURE:
<223> OTHER INFORMATION: Synthesized

<400> SEQUENCE: 50

Met Glu Trp Ile Trp Ile Phe Leu Phe Ile Leu Ser Gly Thr Ala Gly
1               5                   10                  15

Val His Ser Gln Phe Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Ser Tyr Gly Ile Ser Trp Val Lys Gln Arg Thr Gly Gln Gly Leu
    50                  55                  60

Glu Trp Ile Gly Glu Ile Tyr Phe Arg Ser Gly Asn Ile Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Arg Ser Lys Thr Phe Tyr Ser Asn Tyr Gly Gly Val
        115                 120                 125

Phe Asp Tyr Trp Gly Gln Gly Thr Thr Leu Thr Val Ser Ser
    130                 135                 140

<210> SEQ ID NO 51
<211> LENGTH: 131
<212> TYPE: PRT
<213> ORGANISM: Artificial Sequence
<220> FEATURE:

<223> OTHER INFORMATION: Synthesized

<400> SEQUENCE: 51

Met Lys Leu Pro Val Arg Leu Leu Val Leu Met Phe Trp Ile Pro Val
1               5                   10                  15

Ser Thr Cys Asp Val Leu Val Thr Gln Thr Pro Leu Ser Leu Pro Val
            20                  25                  30

Ser Leu Gly Asp Gln Ala Ser Ile Ser Cys Arg Ser Ser Arg Ser Ile
        35                  40                  45

Val His Asn Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Pro Thr Phe Gly Gly Gly Thr Arg Leu
        115                 120                 125

Glu Ile Lys
    130

<210> SEQ ID NO 52
<211> LENGTH: 426
<212> TYPE: PRT
<213> ORGANISM: Artificial Sequence
<220> FEATURE:
<223> OTHER INFORMATION: Synthesized

<400> SEQUENCE: 52

Ala Thr Gly Gly Ala Ala Thr Gly Gly Ala Thr Cys Thr Gly Gly Ala
1               5                   10                  15

Thr Cys Thr Thr Thr Cys Thr Cys Thr Thr Cys Ala Thr Cys Cys Thr
            20                  25                  30

Gly Thr Cys Ala Gly Gly Ala Ala Cys Thr Gly Cys Ala Gly Gly Thr
        35                  40                  45

Gly Thr Cys Cys Ala Cys Thr Cys Cys Cys Ala Gly Thr Thr Thr Cys
        50                  55                  60

Ala Ala Cys Thr Ala Cys Ala Gly Cys Ala Gly Thr Cys Thr Gly Gly
65                  70                  75                  80

Ala Gly Cys Thr Gly Ala Gly Cys Thr Gly Gly Cys Gly Ala Gly Gly
                85                  90                  95

Cys Cys Thr Gly Gly Gly Cys Thr Thr Cys Ala Gly Thr Gly Ala Ala
                100                 105                 110

Ala Gly Cys Thr Gly Thr Cys Cys Thr Gly Cys Ala Ala Gly Gly Cys
            115                 120                 125

Thr Thr Cys Thr Gly Gly Cys Thr Ala Cys Ala Cys Cys Thr Thr Cys
            130                 135                 140

Ala Cys Ala Ala Gly Cys Thr Ala Thr Gly Gly Thr Ala Thr Ala Ala
145                 150                 155                 160

Gly Cys Thr Gly Gly Gly Thr Gly Ala Ala Gly Cys Ala Gly Ala Gly
                165                 170                 175

Ala Ala Cys Thr Gly Gly Ala Cys Ala Gly Gly Gly Cys Cys Thr Thr
        180                 185                 190

Gly Ala Gly Thr Gly Gly Ala Thr Thr Gly Gly Ala Gly Ala Gly Ala
                195                 200                 205

```
Thr Thr Thr Ala Thr Thr Thr Thr Ala Gly Ala Ala Gly Thr Gly Gly
    210                 215                 220

Thr Ala Ala Thr Ala Thr Thr Thr Ala Cys Thr Ala Cys Ala Ala Thr
225                 230                 235                 240

Gly Ala Gly Ala Ala Ala Thr Thr Thr Ala Ala Gly Gly Gly Cys Ala
                245                 250                 255

Ala Gly Gly Cys Cys Ala Cys Ala Cys Thr Gly Ala Cys Thr Gly Cys
            260                 265                 270

Ala Gly Ala Cys Ala Ala Ala Thr Cys Cys Thr Cys Cys Ala Gly Cys
        275                 280                 285

Ala Cys Ala Gly Cys Gly Thr Ala Cys Ala Thr Gly Gly Ala Gly Cys
    290                 295                 300

Thr Cys Cys Gly Cys Ala Gly Cys Cys Thr Gly Ala Cys Ala Thr Cys
305                 310                 315                 320

Thr Gly Ala Gly Gly Ala Cys Thr Cys Thr Gly Cys Gly Gly Thr Cys
                325                 330                 335

Thr Ala Thr Thr Thr Cys Thr Gly Thr Gly Cys Ala Ala Gly Ala Thr
            340                 345                 350

Cys Gly Ala Ala Gly Ala Cys Cys Thr Thr Cys Thr Ala Thr Ala Gly
        355                 360                 365

Thr Ala Ala Cys Thr Ala Cys Gly Gly Ala Gly Gly Gly Gly Thr Thr
    370                 375                 380

Thr Thr Thr Gly Ala Cys Thr Ala Cys Thr Gly Gly Gly Gly Cys Cys
385                 390                 395                 400

Ala Ala Gly Gly Cys Ala Cys Cys Ala Cys Thr Cys Thr Cys Ala Cys
                405                 410                 415

Ala Gly Thr Cys Thr Cys Cys Thr Cys Ala
            420                 425
```

<210> SEQ ID NO 53
<211> LENGTH: 393
<212> TYPE: PRT
<213> ORGANISM: Artificial Sequence
<220> FEATURE:
<223> OTHER INFORMATION: Synthesized

<400> SEQUENCE: 53

```
Ala Thr Gly Ala Ala Gly Thr Thr Gly Cys Cys Thr Gly Thr Thr Ala
1               5                   10                  15

Gly Gly Cys Thr Gly Thr Thr Gly Gly Thr Gly Cys Thr Gly Ala Thr
            20                  25                  30

Gly Thr Thr Cys Thr Gly Gly Ala Thr Thr Cys Cys Thr Gly Thr Thr
        35                  40                  45

Thr Cys Cys Ala Cys Cys Thr Gly Thr Gly Ala Thr Gly Thr Thr Thr
    50                  55                  60

Thr Gly Gly Thr Gly Ala Cys Cys Cys Ala Ala Ala Cys Thr Cys Cys
65                  70                  75                  80

Ala Cys Thr Cys Thr Cys Cys Cys Thr Gly Cys Cys Thr Gly Thr Cys
                85                  90                  95

Ala Gly Thr Cys Thr Thr Gly Gly Ala Gly Ala Thr Cys Ala Ala Gly
            100                 105                 110

Cys Cys Thr Cys Cys Ala Thr Cys Thr Cys Thr Thr Gly Cys Ala Gly
        115                 120                 125

Ala Thr Cys Thr Ala Gly Thr Cys Gly Gly Ala Gly Cys Ala Thr Thr
    130                 135                 140
```

-continued

```
Gly Thr Thr Cys Ala Thr Ala Ala Thr Ala Ala Thr Gly Gly Ala Ala
145                 150                 155                 160

Ala Cys Ala Cys Cys Thr Ala Thr Thr Thr Ala Gly Ala Ala Thr Gly
                165                 170                 175

Gly Thr Ala Cys Cys Thr Gly Cys Ala Gly Ala Ala Cys Cys Ala
            180                 185                 190

Gly Gly Cys Cys Ala Gly Thr Cys Thr Cys Ala Ala Ala Gly Cys
        195                 200                 205

Thr Cys Cys Thr Gly Ala Thr Cys Thr Ala Cys Ala Ala Ala Gly Thr
    210                 215                 220

Thr Thr Cys Cys Ala Ala Cys Cys Gly Ala Thr Thr Thr Cys Thr
225                 230                 235                 240

Gly Gly Gly Gly Thr Cys Cys Ala Gly Ala Cys Ala Gly Gly Thr
                245                 250                 255

Thr Cys Ala Gly Thr Gly Gly Cys Ala Gly Thr Gly Gly Ala Thr Cys
            260                 265                 270

Ala Gly Gly Gly Ala Cys Ala Gly Ala Thr Thr Thr Cys Ala Cys Ala
        275                 280                 285

Cys Thr Cys Ala Ala Gly Ala Thr Cys Ala Gly Cys Ala Gly Ala Gly
        290                 295                 300

Thr Gly Gly Ala Gly Gly Cys Thr Gly Ala Gly Gly Ala Thr Cys Thr
305                 310                 315                 320

Gly Gly Gly Ala Gly Thr Thr Ala Thr Thr Ala Cys Thr Gly Cys
                325                 330                 335

Thr Thr Thr Cys Ala Ala Gly Gly Thr Thr Cys Ala Cys Ala Thr Gly
            340                 345                 350

Thr Thr Cys Cys Thr Cys Cys Cys Ala Cys Gly Thr Thr Cys Gly Gly
            355                 360                 365

Ala Gly Gly Gly Gly Gly Ala Cys Cys Ala Gly Gly Cys Thr Gly
    370                 375                 380

Gly Ala Ala Ala Thr Ala Ala Ala
385                 390
```

ANTIBODIES TO TIP1 AND METHODS OF USE THEREOF

CROSS REFERENCE TO RELATED APPLICATIONS

This application claims the benefit of International application number PCT/US2018/017696, filed Feb. 9, 2018, which claims the benefit of U.S. Provisional Application No. 62/457,624, filed on Feb. 10, 2017, the disclosures of which are hereby incorporated by reference in their entirety.

GOVERNMENTAL RIGHTS

This invention was made with government support under CA210687 and CA196002 awarded by the National Institutes of Health. The government has certain rights in the invention.

FIELD OF THE INVENTION

The disclosure provides antigen binding proteins useful in the recognition of tumor cells and tumor specific delivery of drugs and therapies.

BACKGROUND OF THE INVENTION

Glioblastoma multiforme (GBM) and non-small-cell lung cancer (NSCLC) are among the most difficult and challenging cancers to treat. Lung cancer is the most common type of malignancy and is one of the leading causes of cancer-related deaths worldwide. According to 2016 cancer statistics, an estimated total of 221,200 new lung cancer cases and 158,040 lung cancer deaths occurred in the United States in 2015. Of all lung cancer cases, 85% are NSCLC. Although advancements in diagnosis and treatment have improved, the survival of patients with lung cancer, the 5-year overall survival rate is only ~15%. GBM is a highly malignant form of brain tumor with an annual incidence of approximately 12,000 in the United States. It is reported to have a five-year survival rate of about five percent. Thus, there is an urgent need to develop novel treatment strategies for NSCLC and GBM patients.

Exposure of tumor cells to ionizing radiation (IR) is widely known to induce a number of cellular changes. One way that IR can affect tumor cells is through the development of neoantigens which are new molecules that tumor cells express at the cell membrane following some insult or change to the cell. There have been numerous reports in the literature of changes in both tumor and tumor vasculature cell surface molecule expression following treatment with IR. The usefulness of neoantigens for imaging and therapeutic applications lies in the fact that they are differentially expressed on the surface of irradiated tumor cells to a greater extent than on normal tissues. This differential expression provides a mechanism by which tumor cells can be "marked" by radiation for further targeting. Drug delivery vehicles or imaging agents conjugated to ligands that recognize and interact with the neoantigens can help to improve tumor-specific targeting and reduce systemic toxicity with cancer drugs.

Other objects, advantages and features of the present invention will become apparent from the following specification taken in conjunction with the accompanying figures.

SUMMARY OF THE INVENTION

In an aspect, the present invention encompasses cell line that expresses an antigen binding protein comprising an amino acid sequence selected from the group consisting of SEQ ID NO:4, SEQ ID NO:5, SEQ ID NO:6 SEQ ID NO:7, SEQ ID NO:8, SEQ ID NO:9, SEQ ID NO:10, SEQ ID NO:14, SEQ ID NO:15, SEQ ID NO: 16, SEQ ID NO:17, SEQ ID NO:18, SEQ ID NO:19, SEQ ID NO:20, SEQ ID NO:21, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:34, SEQ ID NO:35, SEQ ID NO: 36, SEQ ID NO:37, SEQ ID NO:38, SEQ ID NO:39, SEQ ID NO: 40, SEQ ID NO:41, SEQ ID NO:44, SEQ ID NO:45, SEQ ID NO:46, SEQ ID NO:47, SEQ ID NO:48, SEQ ID NO:49, SEQ ID NO:50 and SEQ ID NO:51, wherein the antigen binding protein specifically bind to tax interacting protein 1 (TIP1). Specifically, antigen binding proteins of the disclosure bind to the PSD-95/DIgA/ZO-1 (PDZ) domain of TIP1.

In another aspect, the present invention encompasses an isolated antigen binding protein that specifically binds TIP1 and comprises a heavy chain variable region comprising SEQ ID NO:4, SEQ ID NO:5, and SEQ ID NO:6. In another aspect, the present invention encompasses an isolated antigen binding protein that specifically binds TIP1 and comprises a heavy chain variable region comprising SEQ ID NO:14, SEQ ID NO:15, and SEQ ID NO:16. In another aspect, the present invention encompasses an isolated antigen binding protein that specifically binds TIP1 and comprises a heavy chain variable region comprising SEQ ID NO:24, SEQ ID NO:25, and SEQ ID NO:26. In another aspect, the present invention encompasses an isolated antigen binding protein that specifically binds TIP1 and comprises a heavy chain variable region comprising SEQ ID NO:34, SEQ ID NO:35, and SEQ ID NO:36. In another aspect, the present invention encompasses an isolated antigen binding protein that specifically binds TIP1 and comprises a heavy chain variable region comprising SEQ ID NO:44, SEQ ID NO:45, and SEQ ID NO:46.

In still another aspect, the present invention encompasses an isolated antigen binding protein that specifically binds TIP1 and comprises a light chain variable region comprising SEQ ID NO:7, SEQ ID NO:8, and SEQ ID NO:9 or SEQ ID NO:10. In another aspect, the present invention encompasses an isolated antigen binding protein that specifically binds TIP1 and comprises a light chain variable region comprising SEQ ID NO:17, SEQ ID NO:18, and SEQ ID NO:19. In another aspect, the present invention encompasses an isolated antigen binding protein that specifically binds TIP1 and comprises a light chain variable region comprising SEQ ID NO:27, SEQ ID NO:28, and SEQ ID NO:29. In another aspect, the present invention encompasses an isolated antigen binding protein that specifically binds TIP1 and comprises a light chain variable region comprising SEQ ID NO:37, SEQ ID NO:38, and SEQ ID NO:39. In another aspect, the present invention encompasses an isolated antigen binding protein that specifically binds TIP1 and comprises a light chain variable region comprising SEQ ID NO:47, SEQ ID NO:48, and SEQ ID NO:49.

In another aspect, the present invention encompasses an isolated antigen binding protein that specifically binds TIP1 and comprises a heavy chain CDR3 comprising the amino acid sequence of SEQ ID NO:6 with zero to two amino acid substitutions. In another aspect, the present invention encompasses an isolated antigen binding protein that specifically binds TIP1 and comprises a heavy chain CDR3 comprising the amino acid sequence of SEQ ID NO:16 with zero to two amino acid substitutions. In another aspect, the present invention encompasses an isolated antigen binding protein that specifically binds TIP1 and comprises a heavy chain CDR3 comprising the amino acid sequence of SEQ ID NO:26 with zero to two amino acid substitutions. In another aspect, the present invention encompasses an isolated antigen binding protein that specifically binds TIP1 and comprises a heavy chain CDR3 comprising the amino acid sequence of SEQ ID NO:36 with zero to two amino acid substitutions. In another aspect, the present invention encompasses an isolated antigen binding protein that specifically binds TIP1 and comprises a heavy chain CDR3 comprising the amino acid sequence of SEQ ID NO:46 with zero to two amino acid substitutions.

In yet another aspect, the present invention encompasses an antigen binding protein comprising a heavy chain variable region comprising a sequence selected from the group consisting of SEQ ID NO:20, SEQ ID NO:30, SEQ ID NO:40 and SEQ ID NO:50 and/or a light chain variable region comprising a sequence selected from the group consisting of SEQ ID NO:21, SEQ ID NO:31, SEQ ID NO:41 and SEQ ID NO:51.

In yet still another aspect, the present invention encompasses a method of detecting a tumor in a subject. The method comprises exposing a target area of the subject where the presence of a tumor is suspected to ionizing radiation; administering to the subject a composition to detect the presence of TIP1 in the target area, wherein the composition comprises one or more targeting antigen binding proteins wherein each targeting antigen binding protein specifically binds to the PDZ domain of TIP1 exposed on an irradiated cell and is conjugated to a detectable label; and detecting the detectable label to detect the presence of TIP1, wherein the presence of TIP1 indicates the presence of a tumor in the target area of the subject.

In a different aspect, the present invention encompasses a method of enhancing radiotherapy in a subject. The method comprises administering a pharmacologically effective amount of an isolated antigen binding protein of the invention to the subject, such that radiotherapy is enhanced.

In other aspects, the present invention encompasses a method of delivering a therapeutic agent to a cell expressing TIP1 in a subject. The method comprises exposing a target area of the subject where the presence of a tumor is suspected to ionizing radiation; and administering an isolated antigen binding protein of the invention to the subject.

In still other aspects, the present invention encompasses a method of detecting TIP1 in a sample. The method comprises obtaining a sample, and detecting and/or measuring the amount of TIP1 in the sample using an antigen binding protein of the invention.

In yet still in other aspects, the present invention encompasses a method of attenuating proliferation of a tumor cell and/or killing a tumor cells. The method comprises contacting the tumor cell with an isolated antigen binding protein of the invention. Specifically, an isolated antigen binding protein which binds to the PDZ domain of TIP1.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

The application file contains at least one drawing executed in color. Copies of this patent application publication with color drawing(s) will be provided by the Office upon request and payment of the necessary fee. Figures represented herein are not limitations to the various embodiments according to the invention and are presented for exemplary illustration of the invention.

(FIG. 1A) A549 cells, (FIG. 1B) D54 cells, (FIG. 1C) H460 cells, and (FIG. 1D) U251 cells. (FIG. 1E and FIG. 1F) Proliferation of A549 and U251 cells which were transduced with either CRISPR control vector or TIP1 sgRNAs was evaluated by the trypan blue dye exclusion assay at the indicated time points. Shown are the mean fold change in cell number relative to CRISPR control and SD from three different experiments *P<0.05, *P<0.001, **P<0.0001

(FIG. 2A) NSCLC (A549 and LLC) and GBM (D54 and GL261) cell proliferation following treatment with non-PDZ antibody or anti-PDZ antibody for 96 h. Proliferating cells were evaluated using Trypan blue dye exclusion assays. Shown are the mean percentages of proliferating cells relative to the isotype control and SD from three treatments. (FIG. 2B) Anti-PDZ Ab treatment does not alter cell viability in normal lung (MRC-5) and endothelial (HU-VEC) cells. Cells were treated with 1 µg/ml anti-PDZ or isotype control antibody for 96 hours. Trypan blue dye exclusion assay was performed to count the viable cells. Shown are the percent viable cells as bar graph with SD from three different experiments. (FIG. 2C) TIP1 knockout abrogates the effect of the anti-PDZ/TIP1 antibody on cell proliferation. A549 and U251 cells having TIP1 KO were treated with anti-PDZ/TIP1 antibody and cell proliferation was evaluated. Shown are the mean percentages of proliferating cells relative to the untreated CRISPR control cells and SD from three treatments. (FIG. 2C and FIG. 2D) TIP1 knockout abrogates the effect of the anti-PDZ/TIP1 antibody on cell proliferation. A549 and U251 cells having TIP1 KO were treated with anti-PDZ/TIP1 antibody and cell proliferation was evaluated. Shown are the mean percentages of proliferating cells relative to the untreated CRISPR control cells and SD from three treatments.

(FIG. 4A, FIG. 4B, FIG. 4C, FIG. 4D) Live cell fluorescent imaging showing internalization of anti-PDZ antibody. A549 cells were labeled with cell mask orange dye and treated with Alexa-Flour 488 labeled anti-PDZ antibody. Live cell images were captured every 5 minutes in a spinning-disk fluorescent microscope. Shown are representative images at various time points. Yellow spots indicate the internalized antibodies. (FIG. 4E, FIG. 4F, FIG. 4G, FIG. 4H) Annexin V/PI assays with lung cancer (A549 and H460, FIG. 4E and FIG. 4G, respectively) and glioblastoma (D54 and U251, FIG. 4F and FIG. 4H, respectively) cells. A549, H460, D54 and U251 cells were treated with 1 µg/ml of anti-PDZ antibody. Cells were stained with Annexin V and PI 96 h after treatment and analyzed by flow cytometry. Shown are the mean percentage of late apoptotic cells (Annexin V and PI positive) and dead cells (PI positive) with SD from three different experiments ****P<0.0001

(FIG. 5A) Total cellular proteins were immunoblotted using antibodies against phospho-Akt (S473), total Akt, and GAPDH was used as a loading control. (FIG. 5B) Total cellular proteins were immunoblotted using antibodies against phospho-mTOR (S2448), total mTOR, phospo-P70S6 (T389) total-P70S6 phospo-4EBP1 (T70), 4EBP1 (T70) and GAPDH was used as a loading control.

(FIG. 6A, FIG. 6B, FIG. 6C, FIG. 6D) Colony formation assays with lung cancer (A549 and H460, FIG. 6A and FIG. 6C, respectively) and glioblastoma (D54 and U251, FIG. 6B and FIG. 6D, respectively) cells. A549, H460, D54 and U251 cells were treated with 1 µg/ml of anti-PDZ antibody or isotype control for 96 h and plated to measure colony formation. Cells were then irradiated with 3 Gy and incubated for 10-14 days. Colonies comprising of 50 or more were scored. Shown are the mean surviving fraction normalized to the isotype control with SD from three different experiments *P<0.05, P<0.01, *P<0.001, **P<0.0001 A549 (FIG. 6E, FIG. 6G) and U251 (FIG. 6F, FIG. 6H) cells were implanted into the left and right flank of athymic nude mice. Once the tumors were palpable (~200 mm³), the tumors on the right flank were irradiated with 2 Gy for 5 consecutive days for a total of 10 Gy. The tumors on the left flank served as un-irradiated sham control. The tumor bearing mice were treated either with isotype control antibody or anti-TIP-1 antibody on days 1 and 4 after initiating the XRT treatment. Tumor volumes were measured using digital calipers. Shown are the mean tumor volumes of A549 and U251 with SD from 5 mice in each treatment P<0.01, ****P<0.0001. (FIG. 6I and FIG. 6J) Western blot analysis of tumor lysates showing downregulation of phospho- and total AKT and phospho-, total-mTOR and 4EBP-1. (FIG. 6K, FIG. 6L, FIG. 6M and FIG. 6N) Lung cancer (A549 and H460) and glioblastoma (D54 and U251) cells were treated with 1 µg/ml antibody and irradiated with 3Gy or 0Gy. Trypan blue dye exclusion assay was performed after 96 h. Shown are the percent viable cells as a bar graph with SD from three treatments.

FIG. 7 depicts the localization of designed PDZ peptide (SEQ ID NO:3) in the whole Tip1 protein sequence (SEQ ID NO:1).

(FIG. 8A) PDZ peptide on NC membrane reacted with 24 positive clones. (FIG. 8B) Tip1 peptide on NC membrane reacted with 24 positive clones.

(FIG. 9A) PDZ scFv test: peptide on ELISA plate. (FIG. 9B) PDZ peptide scFv test: Tip 1 on ELISA plate.

FIG. 10A and FIG. 10B depict Western-blot assays of anti PDZ scFv clones. (FIG. 10A) A549 3Gyx3 cell lysate. (FIG. 10B) Recombinant Tip1 protein.

(FIG. 11A) Treatment with PDZ scFv G14. (FIG. 11B) Treatment with PDZ scFv H2. (FIG. 11C) Treatment with PDZ scFv D2.

(FIG. 12A) Effect of PDZ scFv on cell proliferation using A549 cells. (FIG. 12B) Effect of PDZ scFv on cell proliferation using U251 cells.

FIG. 14A depicts the CDRs of PDZ scFv clone G14. SEQ ID NO:4 (GFTFSNYA), SEQ ID NO:5 (VSGSGAST), SEQ ID NO:6 (AKHGTRFDYWGQRTLVTVS) and SEQ ID NO:7 (QSVSSY), SEQ ID NO:8 (GAS), and SEQ ID NO:9 (QQT). FIG. 14B depicts the CDRs of PDZ scFv clone H2. SEQ ID NO:4 (GFTFSNYA), SEQ ID NO:5 (VSGSGAST), SEQ ID NO:6 (AKHGTRFDYWGQRTLVTVS) and SEQ ID NO:7 (QSVSSY), SEQ ID NO:8 (GAS), and SEQ ID NO:10 (QQTYPLTFGRWKIK).

FIG. 15A shows viable cells following treatment with 10 µg of antibody. FIG. 15B shows viable cells following treatment with 15 µg of antibody.

FIG. 16A, FIG. 16B and FIG. 16C show the specificity of 2F10, 3D6, 7H5, and 4612 TIP1 PDZ domain binding proteins. FIG. 16A depicts an ELISA assay with the TIP1 mouse monoclonal hybridoma supernatants showing saturation curves. FIG. 16B shows the affinity of the purified mouse monoclonal anti-TIP antibodies as detected by Biacore. FIG. 16C shows the mean fluorescence intensity of the anti-TIP1 antibodies showing cell surface binding by flow cytometry.

FIG. 17A depicts the heavy chain DNA sequence of 2F10 with a leader sequence (SEQ ID NO:22). FIG. 17B depicts the heavy chain amino acid sequence of 2F10 with a leader sequence (SEQ ID NO:20), including heavy chain CDR1 (SEQ ID NO:14), CDR2 (SEQ ID NO:15), and CDR3 (SEQ ID NO:16). FIG. 17C depicts the light chain DNA sequence of 2F10 with a leader sequence (SEQ ID NO:23). FIG. 17D depicts the light chain amino acid sequence of 2F10 with a leader sequence (SEQ ID NO:21), including heavy chain CDR1 (SEQ ID NO:17), CDR2 (SEQ ID NO:18), and CDR3 (SEQ ID NO:19).

FIG. 18A depicts the heavy chain DNA sequence of 3D6 with a leader sequence (SEQ ID NO:32). FIG. 18B depicts the heavy chain amino acid sequence of 3D6 with a leader sequence (SEQ ID NO:30), including heavy chain CDR1 (SEQ ID NO:24), CDR2 (SEQ ID NO:25), and CDR3 (SEQ ID NO:26). FIG. 18C depicts the light chain DNA sequence of 3D6 with a leader sequence (SEQ ID NO:33). FIG. 18D depicts the light chain amino acid sequence of 3D6 with a leader sequence (SEQ ID NO:31), including heavy chain CDR1 (SEQ ID NO:27), CDR2 (SEQ ID NO:28), and CDR3 (SEQ ID NO:29).

FIG. 19A depicts the heavy chain DNA sequence of 4612 with a leader sequence (SEQ ID NO:52). FIG. 19B depicts the heavy chain amino acid sequence of 4612 with a leader sequence (SEQ ID NO:50), including heavy chain CDR1 (SEQ ID NO:44), CDR2 (SEQ ID NO:45), and CDR3 (SEQ ID NO:46). FIG. 19C depicts the light chain DNA sequence of 4B12 with a leader sequence (SEQ ID NO:53). FIG. 19D depicts the light chain amino acid sequence of 4B12 with a leader sequence (SEQ ID NO:51), including heavy chain CDR1 (SEQ ID NO:47), CDR2 (SEQ ID NO:48), and CDR3 (SEQ ID NO:49).

FIG. 20A depicts the heavy chain DNA sequence of 7H5 with a leader sequence (SEQ ID NO:42). FIG. 20B depicts the heavy chain amino acid sequence of 7H5 with a leader sequence (SEQ ID NO:40), including heavy chain CDR1 (SEQ ID NO:34), CDR2 (SEQ ID NO:35), and CDR3 (SEQ ID NO:36). FIG. 20C depicts the light chain DNA sequence of 7H5 with a leader sequence (SEQ ID NO:43). FIG. 20D depicts the light chain amino acid sequence of 7H5 with a leader sequence (SEQ ID NO:41), including heavy chain CDR1 (SEQ ID NO:37), CDR2 (SEQ ID NO:38), and CDR3 (SEQ ID NO:39).

DETAILED DESCRIPTION OF THE INVENTION

Figure 1A:
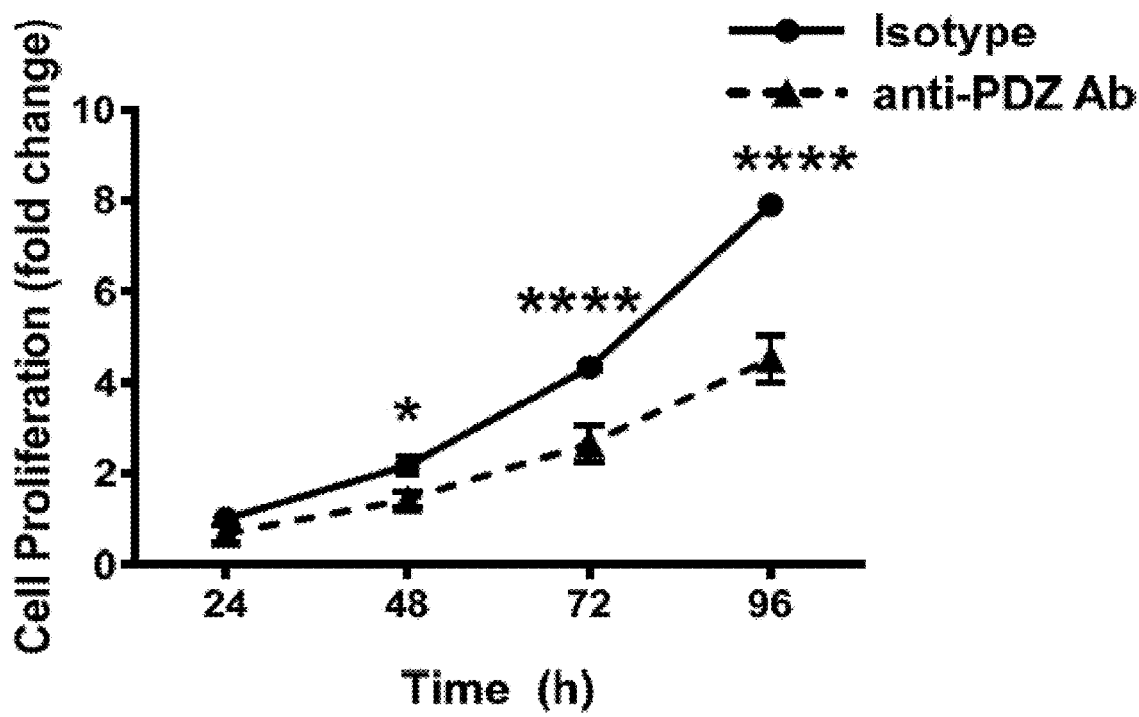
FIG. 1A, FIG. 1B, FIG. 1C, FIG. 1D, FIG. 1E and FIG. 1F depict graphs showing anti-PDZ antibody treatment reduces cancer cell proliferation in a time-dependent manner. Cells were treated with 1 µg/ml of the anti-PDZ antibody or isotype control, antibody for 24 h, 48 h, 72 h, and 96 h. Proliferating cells (Viable) were evaluated by trypan blue dye exclusion assay at the indicated time points. Shown are the mean fold change in cell number relative to control and SD from three different experiments.
Figure 1B:
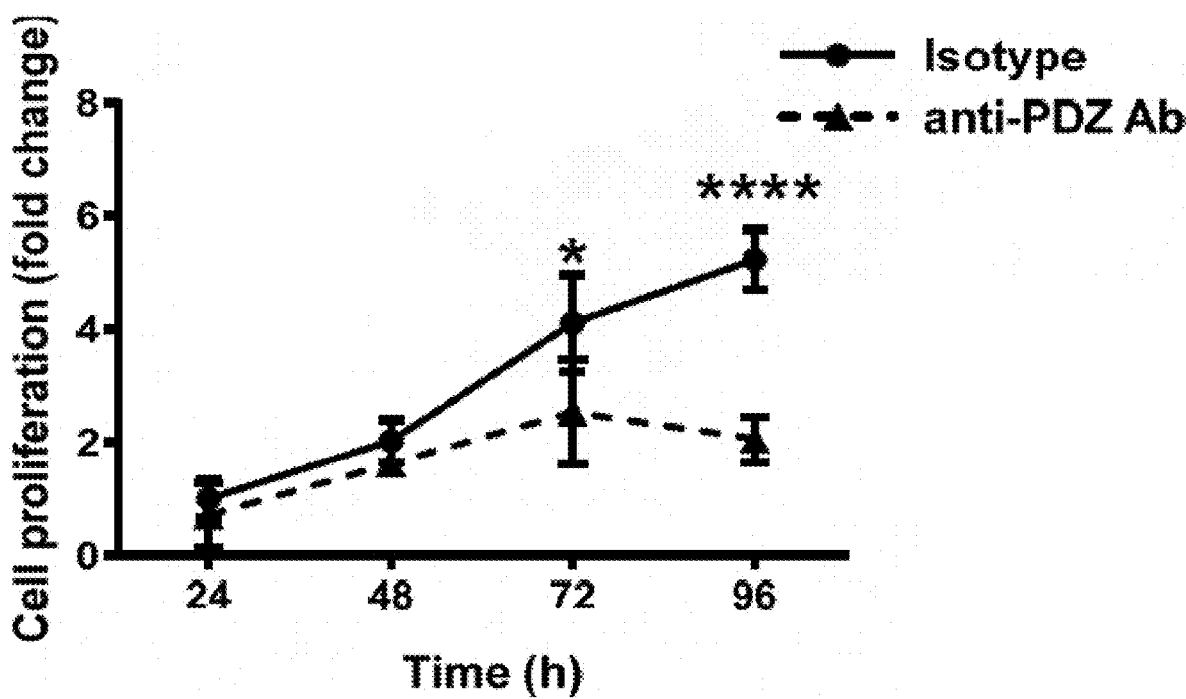
Figure 1C:
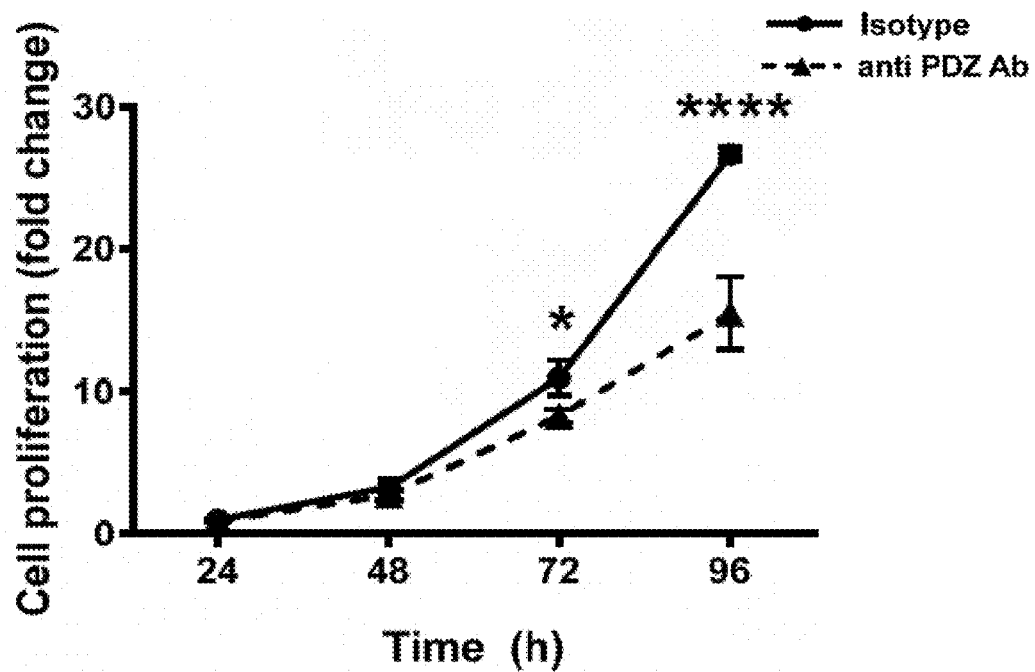
Figure 1D:
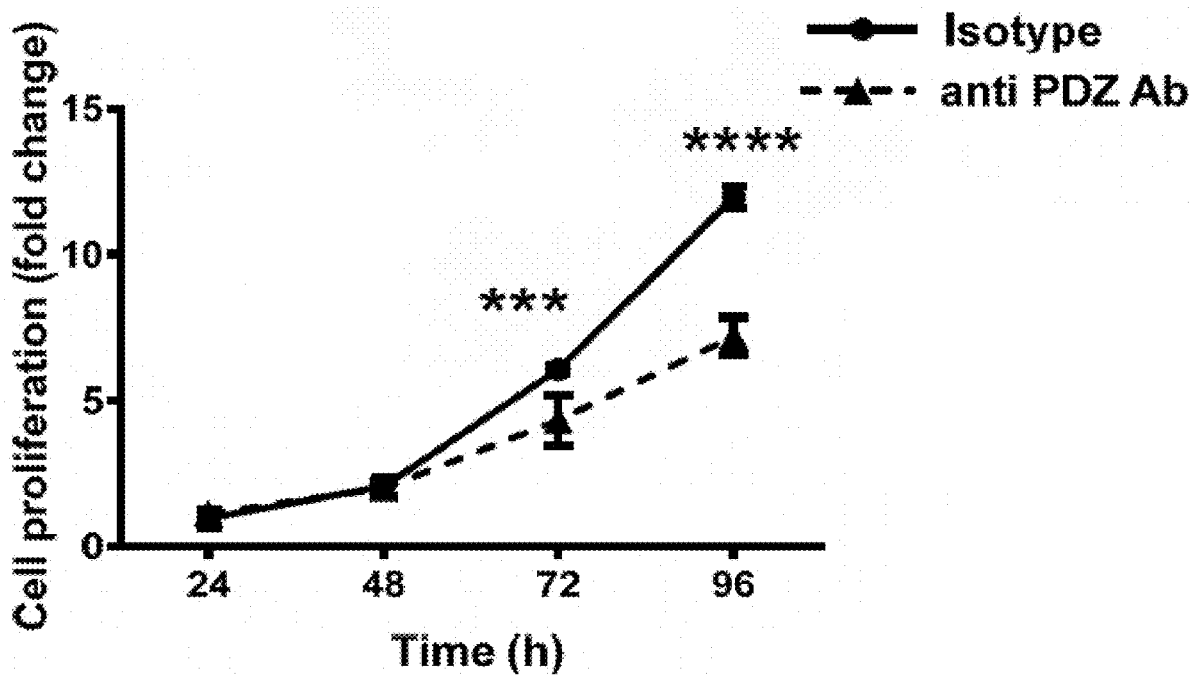

The present disclosure provides antigen binding proteins that recognize tumor cells. The antigen binding proteins may be used to provide tumor specific delivery, for instance, of drugs or therapeutic agents, as well as enhancing the efficacy of radiotherapy. In particular, the present disclosure provides for antigen binding proteins that bind to tax interacting protein 1 (TIP1). Advantageously, these antigen binding proteins specifically bind tumor cells and not normal cells. In an exemplary embodiment, antigen binding proteins of the disclosure specifically bind to epitopes exposed on irradiated tumor related cells. For instance, antigen binding proteins of the disclosure may bind to extracellular, transmembrane or intracellular epitopes on irradiated tumor related cells. Specifically, antigen binding proteins of the disclosure bind to the PSD-95/DIgA/ZO-1 (PDZ) domain of TIP1 on irradiated tumor related cells.

The antibodies and methods of their use are described in further detail below.

I. Anti-TIP1 Antigen Binding Proteins

In an aspect, anti-TIP1 antigen binding proteins include antigen binding proteins that specifically bind an epitope within the PDZ domain. More specifically, anti-TIP1 antigen binding proteins include antigen binding proteins that specifically bind an epitope within the PDZ domain of TIP1. Generally speaking, the epitope is detectable on the surface of a tumor cell following irradiation. The epitope may or may not be detectable on the cell surface in the absence of irradiation. Alternatively, an epitope may be detectable on the surface of a tumor cell both in the absence of irradiation and following irradiation, though the detectable signal is greater following irradiation. The PDZ domain spans about 80 to about 100 amino acid residues and is comprised of six β-sheets and two α-helices. TIP1 comprises a single PDZ domain from about residue 13 to about residue 112 of the 124-amino acid protein (SEQ ID NO:1; MSYIPGQPVTAVVQRVEIHKLRQGENLILGFSIGG-GIDQDPSQNPFSEDK TDKGIYVTRVSEGGPAE-IAGLQIGDKIMQVNGWDMTMVTHDQARKRLTKR-SEEVV RLLVTRQSLQKAVQQSMLS). Accordingly, in certain embodiments, anti-TIP1 antigen binding proteins include antigen binding proteins that specifically bind an epitope within SEQ ID NO:2 (VQRVEIHKLRQGEN-LILGFSIGGGIDQDPSQNPFSEDKTDKGIYVTRV SEGGPAEIAGLQIGD-KIMQVNGWDMTMVTHDQARKRLTKRSEEVVRLL-VTRQ). The epitope may be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids within SEQ ID NO:2. Specifically, the epitope may be about 13, about 14, about 15, about 16, about 17, about 18, about 19, about 20, about 21, about 22, or about 23 amino acids within SEQ ID NO:2. The epitope may be linear or conformational. In an embodiment, the epitope may be about 5, about 6, about 7, about 8, about 9, about 10, about 11, about 12, about 13, about 14, about 15, about 16, about 17, about 18 amino acids within SEQ ID NO:3 (IDQDPSQNPFSEDKTDKG). In a specific embodiment, anti-TIP1 antigen binding proteins include antigen binding proteins that specifically bind an epitope consisting of SEQ ID NO:3. In a specific embodiment, anti-TIP1 antigen binding proteins include antigen binding proteins that specifically bind an epitope consisting of SEQ ID NO:11 (IDQDPSQNPF).

The phrase "specifically binds" herein means antigen binding proteins bind to the protein with an affinity constant or affinity of interaction ($K_D$) of less than 300 nM, less than 250 nM, less than 200 nM, less than 150 nM, less than 100 nM, less than 75 nM, less than 50 nM, less than 25 nM, less than 20 nM, less than 15 nM, less than 10 nM, less than 5 nM, or less than 1 nM. In one embodiment, an anti-TIP1 antigen binding protein binds to an epitope within the PDZ domain with a $K_D$ of less than 250 nM. In an embodiment, an anti-TIP1 antigen binding protein binds to an epitope within the PDZ domain with a $K_D$ of less than 100 nM. In another embodiment, an anti-TIP1 antigen binding protein binds to an epitope within the PDZ domain with a $K_D$ of less than 50 nM. In still another embodiment, an anti-TIP1 antigen binding protein binds to an epitope within the PDZ domain with a $K_D$ of less than 20 nM. In still yet another embodiment, an anti-TIP1 antigen binding protein binds to an epitope within the PDZ domain with a $K_D$ of less than 10 nM. Methods of determining whether an antigen binding protein binds to the PDZ domain of TIP1 are known in the art.

The term "antigen binding protein" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g. bispecific antibodies), and antibody fragments so long as they exhibit the desired biological activity.

The term "monoclonal antibody" refers to an antibody that is derived from a single copy or clone, including e.g., any eukaryotic, prokaryotic, or phage clone. Monoclonal antibodies are obtained from a population of substantially homogeneous antibodies, i.e., the individual antibodies comprising the population are identical except for possible naturally occurring mutations or post-translational modification that may be present in minor amounts. Monoclonal antibodies are highly specific, being directed against a single antigenic epitope. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

The term "fragment thereof" encompasses a fragment or a derivative of an antibody that still substantially retain its biological activity. Therefore, the term "antibody fragment" or "fragment thereof" refers to a portion of a full length antibody, generally the antigen binding or variable region thereof. Examples of an immunologically effective fragment thereof include Fab, Fab', F(ab')$_2$ and Fv fragments, diabodies, linear antibodies, single-chain molecules, and multispecific antibodies formed from antibody fragments. In some contexts herein, fragments will be mentioned specifically for emphasis; nevertheless, it will be understood that regardless of whether fragments are specified, the term "antibody" includes such fragments.

Also included within the definition "antibody" for example are single chain forms, generally designated Fv, regions, of antibodies with this specificity. These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art. In a preferred embodiment, the scFvs of the present disclosure are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

The term "antibody" also includes bispecific monoclonal antibodies (i.e. a protein that comprises fragments of two different monoclonal antibodies and consequently binds two different antigens). A specific example of a bispecific monoclonal antibody may be a Bi-specific T-cell Engager (BiTE) which is a fusion protein consisting of two single-chain variable fragments (scFvs) of different antibodies. In certain embodiments, BiTEs from a link between T cells and infected cells. Accordingly, one scFv is a specific for TIP1 and one scFv binds a T cell. Additionally, an antibody of the disclosure may be a chimeric antigen receptor (CAR), also referred to as an artificial T cell receptor, a chimeric T cell receptor, or a chimeric immunoreceptor. CARs are engineered receptors, which graft an arbitrary specificity onto an immune effector cell. Typically, these receptors are used to graft the specificity of a monoclonal antibody onto a T cell. Additionally, included within the definition "antibody" are single-domain antibodies, generally designated sdAb, which is an antibody fragment consisting of a single monomeric variable antibody domain. A sdAb antibody may be derived from camelids ($V_HH$ fragments) or cartilaginous fishes ($V_{NAR}$ fragments). As long as the protein retains the ability specifically to bind its intended target, it is included within the term "antibody."

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is known.

The basic antibody structural unit of an antibody useful herein comprises a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites, although recombinant versions can be of higher valency. The chains exhibit the same general structure of relatively conserved framework regions (FR) joined by three hypervariable regions, also called complementarity determining regions (hereinafter referred to as "CDRs"). The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883). For example, Kabat, Chothia, combinations thereof, or other known methods of determining CDRs may be used.

Additionally, an antibody of the disclosure can be modified to optimize or minimize effector function. Further, an antibody of the disclosure can be modified to extend half-life. Still further, an antibody of the disclosure can be modified to improve binding affinity. Methods of modifying an antibody to improve the aforementioned characteristics are known in the art. For example, the crystal structures disclosed herein may be used to rationally alter amino acids to optimize contact with the antibody and antigen.

In an aspect, monoclonal anti-TIP1 antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing the PDZ domain or an appropriate subregion thereof. Specifically, such antibodies could be generated by immunizing a human, rabbit, rat or mouse, for example, with a peptide comprising SEQ ID NO:2. More specifically, such antibodies could be generated by immunizing a human, rabbit, rat or mouse, for example, with a peptide comprising SEQ ID NO:3. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-TIP1 antibody that is composed partially or fully of amino acid sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for the PDZ domain of TIP1 is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-TIP1 antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, et al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

The antigen binding proteins of the present disclosure may also be conjugated to a payload, such as a therapeutic agent, a detectable, and/or a delivery device (including, but not limited to, a liposome or a nanoparticle) containing the drug or detectable label. Methods of conjugating an antigen binding protein to a therapeutic agent, a detectable label, a liposome, a nanoparticle or other delivery device are known in the art. Generally speaking, the conjugation should not interfere with the antigen binding protein recognizing its target, and should not interfere with the active site of the target. In some instances, an antigen binding protein may be generated with a cleavable linkage between the antibody and the payload. Such a linker may allow release of the payload at a specific cellular location. Suitable linkers include, but are not limited to, amino acid chains and alkyl chains functionalized with reactive groups for conjugating to both the antigen binding protein of the disclosure and the detectable label and/or therapeutic agent.

A preferred antigen binding protein is a scFv antibody derived from a clone designated G14, H2, 2F10, 3D6, 4B12 or 7H5. As used herein, the term "derived from" means that the "derived" antibody comprises at least one CDR region from the antibody produced by G14, H2, 2F10, 3D6, 4B12 or 7H5. Stated another way, the "derived antibody" comprises at least one amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:14, SEQ ID NO:15, SEQ ID NO:16, SEQ ID NO:17, SEQ ID NO:18, SEQ ID NO:19, SEQ ID NO:24, SEQ ID NO:25, SEQ ID NO:26, SEQ ID NO:27, SEQ ID NO:28, SEQ ID NO:29, SEQ ID NO:34, SEQ ID NO:35, SEQ ID NO:36, SEQ ID NO:37, SEQ ID NO:38, SEQ ID NO:39, SEQ ID NO:44, SEQ ID NO:45, SEQ ID NO:46, SEQ ID NO:47, SEQ ID NO:48, or SEQ ID NO:49.

In one embodiment, an antigen binding protein of the disclosure may be derived from the clone 2F10, and may comprise an amino acid sequence with 90, 91, 92, 93, 94, 95, 96, 97, 98, or 99% identity to the heavy chain variable region of SEQ ID NO:20, and/or may comprise an amino acid sequence with 90, 91, 92, 93, 94, 95, 96, 97, 98, or 99% identity to the light chain variable region of SEQ ID NO:21. In another embodiment, an antigen binding protein of the disclosure may be derived from the clone 3D6, and may comprise an amino acid sequence with 90, 91, 92, 93, 94, 95, 96, 97, 98, or 99% identity to the heavy chain variable region of SEQ ID NO:30, and/or may comprise an amino acid sequence with 90, 91, 92, 93, 94, 95, 96, 97, 98, or 99% identity to the light chain variable region of SEQ ID NO:31. In one embodiment, an antigen binding protein of the disclosure may be derived from the clone 7H5, and may comprise an amino acid sequence with 90, 91, 92, 93, 94, 95, 96, 97, 98, or 99% identity to the heavy chain variable region of SEQ ID NO:40, and/or may comprise an amino acid sequence with 90, 91, 92, 93, 94, 95, 96, 97, 98, or 99% identity to the light chain variable region of SEQ ID NO:41. In another embodiment, an antigen binding protein of the disclosure may be derived from the clone 4B12, and may comprise an amino acid sequence with 90, 91, 92, 93, 94, 95, 96, 97, 98, or 99% identity to the heavy chain variable region of SEQ ID NO:50, and/or may comprise an amino acid sequence with 90, 91, 92, 93, 94, 95, 96, 97, 98, or 99% identity to the light chain variable region of SEQ ID NO:51.

In an exemplary embodiment, an antigen binding protein of the disclosure that binds to the PDZ domain of TIP1 comprises the heavy chain amino acid sequence of SEQ ID NO:20 and the light chain amino acid sequence of SEQ ID NO:21 [i.e. the scFv antibody referred to as 2F10]. In another exemplary embodiment, an antigen binding protein of the disclosure that binds to the PDZ domain of TIP1 comprises the heavy chain amino acid sequence of SEQ ID NO:30 and the light chain amino acid sequence of SEQ ID NO:31 [i.e. the scFv antibody referred to as 3D6].

In yet another exemplary embodiment, an antigen binding protein of the disclosure that binds to the PDZ domain of TIP1 comprises the heavy chain amino acid sequence of SEQ ID NO:40 and the light chain amino acid sequence of SEQ ID NO:41 [i.e. the scFv antibody referred to as 7H5]. In another exemplary embodiment, an antigen binding protein of the disclosure that binds to the PDZ domain of TIP1 comprises the heavy chain amino acid sequence of SEQ ID NO:50 and the light chain amino acid sequence of SEQ ID NO:51 [i.e. the scFv antibody referred to as 4B12].

In one embodiment, an antigen binding protein of the disclosure may comprise a light chain CDR1, such as antibody 1, 70, 118, 166, and 214 of Table A. In another embodiment, an antigen binding protein of the disclosure may comprise a light chain CDR2, such as antibody 4, 73, 121, 169, and 217 of Table A. In yet another embodiment, an antigen binding protein of the disclosure may comprise a light chain CDR3, such as antibody 6, 51, 75, 123, 171, and 219 of Table A. In an alternative embodiment, an antigen binding protein of the disclosure may comprise a combination of two or three light chain CDRs, such as the antibodies 2, 3, 5, 49, 50, 71, 72, 74, 119, 120, 122, 167, 168, 170, 215, 216, and 218 of Table A.

Similarly, in one embodiment, an antigen binding protein of the disclosure may comprise a heavy chain CDR1, such as antibody 7, 76, 124, 172, and 220 of Table A. In another embodiment, an antigen binding protein of the disclosure may comprise a heavy chain CDR2, such as antibody 10, 79, 127, 175 and 223 of Table A. In yet another embodiment, an antigen binding protein of the disclosure may comprise a heavy chain CDR3, such as antibody 12, 81, 129, 177, and 225 of Table A. In an alternative embodiment, an antigen binding protein of the disclosure may comprise a combination of two or three heavy chain CDRs, such as the antibodies 8, 9, 11, 77, 78, 80, 125, 126, 128, 173, 174, 176, 221, 222 and 224 of Table A.

Alternatively, an antigen binding protein of the disclosure may comprise one or more light chain CDRs and one or more heavy chain CDRs, such as the antibodies 13-48, 52-69, 82-117, 130-165, 178-213, and 226-261 of Table A.

TABLE A

| Antibody | Light Chain | | | Heavy Chain | | |
|---|---|---|---|---|---|---|
| | CDR1 | CDR2 | CDR3 | CDR1 | CDR2 | CDR3 |
| 1 | SEQ ID NO: 7 | | | | | |
| 2 | SEQ ID NO: 7 | SEQ ID NO: 8 | | | | |
| 3 | SEQ ID NO: 7 | SEQ ID NO: 8 | SEQ ID NO: 9 | | | |
| 4 | | SEQ ID NO: 8 | | | | |
| 5 | | SEQ ID NO: 8 | SEQ ID NO: 9 | | | |
| 6 | | | SEQ ID NO: 9 | | | |
| 7 | | | | SEQ ID NO: 4 | | |
| 8 | | | | SEQ ID NO: 4 | SEQ ID NO: 5 | |
| 9 | | | | SEQ ID NO: 4 | SEQ ID NO: 5 | SEQ ID NO: 6 |
| 10 | | | | | SEQ ID NO: 5 | |
| 11 | | | | | SEQ ID NO: 5 | SEQ ID NO: 6 |
| 12 | | | | | | SEQ ID NO: 6 |
| 13 | SEQ ID NO: 7 | | | SEQ ID NO: 4 | | |
| 14 | SEQ ID NO: 7 | | | SEQ ID NO: 4 | SEQ ID NO: 5 | |
| 15 | SEQ ID NO: 7 | | | SEQ ID NO: 4 | SEQ ID NO: 5 | SEQ ID NO: 6 |
| 16 | SEQ ID NO: 7 | | | | SEQ ID NO: 5 | |
| 17 | SEQ ID NO: 7 | | | | SEQ ID NO: 5 | SEQ ID NO: 6 |
| 18 | SEQ ID NO: 7 | | | | | SEQ ID NO: 6 |
| 19 | SEQ ID NO: 7 | SEQ ID NO: 8 | | SEQ ID NO: 4 | | |
| 20 | SEQ ID NO: 7 | SEQ ID NO: 8 | | SEQ ID NO: 4 | SEQ ID NO: 5 | |
| 21 | SEQ ID NO: 7 | SEQ ID NO: 8 | | SEQ ID NO: 4 | SEQ ID NO: 5 | SEQ ID NO: 6 |
| 22 | SEQ ID NO: 7 | SEQ ID NO: 8 | | | SEQ ID NO: 5 | |
| 23 | SEQ ID NO: 7 | SEQ ID NO: 8 | | | SEQ ID NO: 5 | SEQ ID NO: 6 |
| 24 | SEQ ID NO: 7 | SEQ ID NO: 8 | | | | SEQ ID NO: 6 |
| 25 | SEQ ID NO: 7 | SEQ ID NO: 8 | SEQ ID NO: 9 | SEQ ID NO: 4 | | |
| 26 | SEQ ID NO: 7 | SEQ ID NO: 8 | SEQ ID NO: 9 | SEQ ID NO: 4 | SEQ ID NO: 5 | |
| 27 | SEQ ID NO: 7 | SEQ ID NO: 8 | SEQ ID NO: 9 | SEQ ID NO: 4 | SEQ ID NO: 5 | SEQ ID NO: 6 |
| 28 | SEQ ID NO: 7 | SEQ ID NO: 8 | SEQ ID NO: 9 | | SEQ ID NO: 5 | |
| 29 | SEQ ID NO: 7 | SEQ ID NO: 8 | SEQ ID NO: 9 | | SEQ ID NO: 5 | SEQ ID NO: 6 |
| 30 | SEQ ID NO: 7 | SEQ ID NO: 8 | SEQ ID NO: 9 | | | SEQ ID NO: 6 |
| 31 | | SEQ ID NO: 8 | | SEQ ID NO: 4 | | |
| 32 | | SEQ ID NO: 8 | | SEQ ID NO: 4 | SEQ ID NO: 5 | |
| 33 | | SEQ ID NO: 8 | | SEQ ID NO: 4 | SEQ ID NO: 5 | SEQ ID NO: 6 |
| 34 | | SEQ ID NO: 8 | | | SEQ ID NO: 5 | |
| 35 | | SEQ ID NO: 8 | | | SEQ ID NO: 5 | SEQ ID NO: 6 |
| 36 | | SEQ ID NO: 8 | | | | SEQ ID NO: 6 |
| 37 | | SEQ ID NO: 8 | SEQ ID NO: 9 | SEQ ID NO: 4 | | |
| 38 | | SEQ ID NO: 8 | SEQ ID NO: 9 | SEQ ID NO: 4 | SEQ ID NO: 5 | |
| 39 | | SEQ ID NO: 8 | SEQ ID NO: 9 | SEQ ID NO: 4 | SEQ ID NO: 5 | SEQ ID NO: 6 |
| 40 | | SEQ ID NO: 8 | SEQ ID NO: 9 | | SEQ ID NO: 5 | |
| 41 | | SEQ ID NO: 8 | SEQ ID NO: 9 | | SEQ ID NO: 5 | SEQ ID NO: 6 |
| 42 | | SEQ ID NO: 8 | SEQ ID NO: 9 | | | SEQ ID NO: 6 |
| 43 | | | SEQ ID NO: 9 | SEQ ID NO: 4 | | |
| 44 | | | SEQ ID NO: 9 | SEQ ID NO: 4 | SEQ ID NO: 5 | |
| 45 | | | SEQ ID NO: 9 | SEQ ID NO: 4 | SEQ ID NO: 5 | SEQ ID NO: 6 |
| 46 | | | SEQ ID NO: 9 | | SEQ ID NO: 5 | |
| 47 | | | SEQ ID NO: 9 | | SEQ ID NO: 5 | SEQ ID NO: 6 |
| 48 | | | SEQ ID NO: 9 | | | SEQ ID NO: 6 |
| 49 | SEQ ID NO: 7 | SEQ ID NO: 8 | SEQ ID NO: 10 | | | |
| 50 | | SEQ ID NO: 8 | SEQ ID NO: 10 | | | |

TABLE A-continued

| | Light Chain | | | Heavy Chain | | |
|---|---|---|---|---|---|---|
| Antibody | CDR1 | CDR2 | CDR3 | CDR1 | CDR2 | CDR3 |
| 51 | | | SEQ ID NO: 10 | | | |
| 52 | SEQ ID NO: 7 | SEQ ID NO: 8 | SEQ ID NO: 10 | SEQ ID NO: 4 | | |
| 53 | SEQ ID NO: 7 | SEQ ID NO: 8 | SEQ ID NO: 10 | SEQ ID NO: 4 | SEQ ID NO: 5 | |
| 54 | SEQ ID NO: 7 | SEQ ID NO: 8 | SEQ ID NO: 10 | SEQ ID NO: 4 | SEQ ID NO: 5 | SEQ ID NO: 6 |
| 55 | SEQ ID NO: 7 | SEQ ID NO: 8 | SEQ ID NO: 10 | | SEQ ID NO: 5 | |
| 56 | SEQ ID NO: 7 | SEQ ID NO: 8 | SEQ ID NO: 10 | | SEQ ID NO: 5 | SEQ ID NO: 6 |
| 57 | SEQ ID NO: 7 | SEQ ID NO: 8 | SEQ ID NO: 10 | | | SEQ ID NO: 6 |
| 58 | | SEQ ID NO: 8 | SEQ ID NO: 10 | SEQ ID NO: 4 | | |
| 59 | | SEQ ID NO: 8 | SEQ ID NO: 10 | SEQ ID NO: 4 | SEQ ID NO: 5 | |
| 60 | | SEQ ID NO: 8 | SEQ ID NO: 10 | SEQ ID NO: 4 | SEQ ID NO: 5 | SEQ ID NO: 6 |
| 61 | | SEQ ID NO: 8 | SEQ ID NO: 10 | | SEQ ID NO: 5 | |
| 62 | | SEQ ID NO: 8 | SEQ ID NO: 10 | | SEQ ID NO: 5 | SEQ ID NO: 6 |
| 63 | | SEQ ID NO: 8 | SEQ ID NO: 10 | | | SEQ ID NO: 6 |
| 64 | | | SEQ ID NO: 10 | SEQ ID NO: 4 | | |
| 65 | | | SEQ ID NO: 10 | SEQ ID NO: 4 | SEQ ID NO: 5 | |
| 66 | | | SEQ ID NO: 10 | SEQ ID NO: 4 | SEQ ID NO: 5 | SEQ ID NO: 6 |
| 67 | | | SEQ ID NO: 10 | | SEQ ID NO: 5 | |
| 68 | | | SEQ ID NO: 10 | | SEQ ID NO: 5 | SEQ ID NO: 6 |
| 69 | | | SEQ ID NO: 10 | | | SEQ ID NO: 6 |
| 70 | SEQ ID NO: 17 | | | | | |
| 71 | SEQ ID NO: 17 | SEQ ID NO: 18 | | | | |
| 72 | SEQ ID NO: 17 | SEQ ID NO: 18 | SEQ ID NO: 19 | | | |
| 73 | | SEQ ID NO: 18 | | | | |
| 74 | | SEQ ID NO: 18 | SEQ ID NO: 19 | | | |
| 75 | | | SEQ ID NO: 19 | | | |
| 76 | | | | SEQ ID NO: 14 | | |
| 77 | | | | SEQ ID NO: 14 | SEQ ID NO: 15 | |
| 78 | | | | SEQ ID NO: 14 | SEQ ID NO: 15 | SEQ ID NO: 16 |
| 79 | | | | | SEQ ID NO: 15 | |
| 80 | | | | | SEQ ID NO: 15 | SEQ ID NO: 16 |
| 81 | | | | | | SEQ ID NO: 16 |
| 82 | SEQ ID NO: 17 | | | SEQ ID NO: 14 | | |
| 83 | SEQ ID NO: 17 | | | SEQ ID NO: 14 | SEQ ID NO: 15 | |
| 84 | SEQ ID NO: 17 | | | SEQ ID NO: 14 | SEQ ID NO: 15 | SEQ ID NO: 16 |
| 85 | SEQ ID NO: 17 | | | | SEQ ID NO: 15 | |
| 86 | SEQ ID NO: 17 | | | | SEQ ID NO: 15 | SEQ ID NO: 16 |
| 87 | SEQ ID NO: 17 | | | | | SEQ ID NO: 16 |
| 88 | SEQ ID NO: 17 | SEQ ID NO: 18 | | SEQ ID NO: 14 | | |
| 89 | SEQ ID NO: 17 | SEQ ID NO: 18 | | SEQ ID NO: 14 | SEQ ID NO: 15 | |
| 90 | SEQ ID NO: 17 | SEQ ID NO: 18 | | SEQ ID NO: 14 | SEQ ID NO: 15 | SEQ ID NO: 16 |
| 91 | SEQ ID NO: 17 | SEQ ID NO: 18 | | | SEQ ID NO: 15 | |
| 92 | SEQ ID NO: 17 | SEQ ID NO: 18 | | | SEQ ID NO: 15 | SEQ ID NO: 16 |
| 93 | SEQ ID NO: 17 | SEQ ID NO: 18 | | | | SEQ ID NO: 16 |
| 94 | SEQ ID NO: 17 | SEQ ID NO: 18 | SEQ ID NO: 19 | SEQ ID NO: 14 | | |
| 95 | SEQ ID NO: 17 | SEQ ID NO: 18 | SEQ ID NO: 19 | SEQ ID NO: 14 | SEQ ID NO: 15 | |
| 96 | SEQ ID NO: 17 | SEQ ID NO: 18 | SEQ ID NO: 19 | SEQ ID NO: 14 | SEQ ID NO: 15 | SEQ ID NO: 16 |
| 97 | SEQ ID NO: 17 | SEQ ID NO: 18 | SEQ ID NO: 19 | | SEQ ID NO: 15 | |
| 98 | SEQ ID NO: 17 | SEQ ID NO: 18 | SEQ ID NO: 19 | | SEQ ID NO: 15 | SEQ ID NO: 16 |
| 99 | SEQ ID NO: 17 | SEQ ID NO: 18 | SEQ ID NO: 19 | | | SEQ ID NO: 16 |
| 100 | | SEQ ID NO: 18 | | SEQ ID NO: 14 | | |
| 101 | | SEQ ID NO: 18 | | SEQ ID NO: 14 | SEQ ID NO: 15 | |
| 102 | | SEQ ID NO: 18 | | SEQ ID NO: 14 | SEQ ID NO: 15 | SEQ ID NO: 16 |
| 103 | | SEQ ID NO: 18 | | | SEQ ID NO: 15 | |
| 104 | | SEQ ID NO: 18 | | | SEQ ID NO: 15 | SEQ ID NO: 16 |
| 105 | | SEQ ID NO: 18 | | | | SEQ ID NO: 16 |
| 106 | | SEQ ID NO: 18 | SEQ ID NO: 19 | SEQ ID NO: 14 | | |
| 107 | | SEQ ID NO: 18 | SEQ ID NO: 19 | SEQ ID NO: 14 | SEQ ID NO: 15 | |
| 108 | | SEQ ID NO: 18 | SEQ ID NO: 19 | SEQ ID NO: 14 | SEQ ID NO: 15 | SEQ ID NO: 16 |
| 109 | | SEQ ID NO: 18 | SEQ ID NO: 19 | | SEQ ID NO: 15 | |
| 110 | | SEQ ID NO: 18 | SEQ ID NO: 19 | | SEQ ID NO: 15 | SEQ ID NO: 16 |
| 111 | | SEQ ID NO: 18 | SEQ ID NO: 19 | | | SEQ ID NO: 16 |
| 112 | | | SEQ ID NO: 19 | SEQ ID NO: 14 | | |
| 113 | | | SEQ ID NO: 19 | SEQ ID NO: 14 | SEQ ID NO: 15 | |
| 114 | | | SEQ ID NO: 19 | SEQ ID NO: 14 | SEQ ID NO: 15 | SEQ ID NO: 16 |
| 115 | | | SEQ ID NO: 19 | | SEQ ID NO: 15 | |
| 116 | | | SEQ ID NO: 19 | | SEQ ID NO: 15 | SEQ ID NO: 16 |
| 117 | | | SEQ ID NO: 19 | | | SEQ ID NO: 16 |
| 118 | SEQ ID NO: 27 | | | | | |
| 119 | SEQ ID NO: 27 | SEQ ID NO: 28 | | | | |
| 120 | SEQ ID NO: 27 | SEQ ID NO: 28 | SEQ ID NO: 29 | | | |
| 121 | | SEQ ID NO: 28 | | | | |
| 122 | | SEQ ID NO: 28 | SEQ ID NO: 29 | | | |
| 123 | | | SEQ ID NO: 29 | | | |
| 124 | | | | SEQ ID NO: 24 | | |
| 125 | | | | SEQ ID NO: 24 | SEQ ID NO: 25 | |
| 126 | | | | SEQ ID NO: 24 | SEQ ID NO: 25 | SEQ ID NO: 26 |

TABLE A-continued

| | Light Chain | | | Heavy Chain | | |
|---|---|---|---|---|---|---|
| Antibody | CDR1 | CDR2 | CDR3 | CDR1 | CDR2 | CDR3 |
| 127 | | | | | SEQ ID NO: 25 | |
| 128 | | | | | SEQ ID NO: 25 | SEQ ID NO: 26 |
| 129 | | | | | | SEQ ID NO: 26 |
| 130 | SEQ ID NO: 27 | | | SEQ ID NO: 24 | | |
| 131 | SEQ ID NO: 27 | | | SEQ ID NO: 24 | SEQ ID NO: 25 | |
| 132 | SEQ ID NO: 27 | | | SEQ ID NO: 24 | SEQ ID NO: 25 | SEQ ID NO: 26 |
| 133 | SEQ ID NO: 27 | | | | SEQ ID NO: 25 | |
| 134 | SEQ ID NO: 27 | | | | SEQ ID NO: 25 | SEQ ID NO: 26 |
| 135 | SEQ ID NO: 27 | | | | | SEQ ID NO: 26 |
| 136 | SEQ ID NO: 27 | SEQ ID NO: 28 | | SEQ ID NO: 24 | | |
| 137 | SEQ ID NO: 27 | SEQ ID NO: 28 | | SEQ ID NO: 24 | SEQ ID NO: 25 | |
| 138 | SEQ ID NO: 27 | SEQ ID NO: 28 | | SEQ ID NO: 24 | SEQ ID NO: 25 | SEQ ID NO: 26 |
| 139 | SEQ ID NO: 27 | SEQ ID NO: 28 | | | SEQ ID NO: 25 | |
| 140 | SEQ ID NO: 27 | SEQ ID NO: 28 | | | SEQ ID NO: 25 | SEQ ID NO: 26 |
| 141 | SEQ ID NO: 27 | SEQ ID NO: 28 | | | | SEQ ID NO: 26 |
| 142 | SEQ ID NO: 27 | SEQ ID NO: 28 | SEQ ID NO: 29 | SEQ ID NO: 24 | | |
| 143 | SEQ ID NO: 27 | SEQ ID NO: 28 | SEQ ID NO: 29 | SEQ ID NO: 24 | SEQ ID NO: 25 | |
| 144 | SEQ ID NO: 27 | SEQ ID NO: 28 | SEQ ID NO: 29 | SEQ ID NO: 24 | SEQ ID NO: 25 | SEQ ID NO: 26 |
| 145 | SEQ ID NO: 27 | SEQ ID NO: 28 | SEQ ID NO: 29 | | SEQ ID NO: 25 | |
| 146 | SEQ ID NO: 27 | SEQ ID NO: 28 | SEQ ID NO: 29 | | SEQ ID NO: 25 | SEQ ID NO: 26 |
| 147 | SEQ ID NO: 27 | SEQ ID NO: 28 | SEQ ID NO: 29 | | | SEQ ID NO: 26 |
| 148 | | SEQ ID NO: 28 | | SEQ ID NO: 24 | | |
| 149 | | SEQ ID NO: 28 | | SEQ ID NO: 24 | SEQ ID NO: 25 | |
| 150 | | SEQ ID NO: 28 | | SEQ ID NO: 24 | SEQ ID NO: 25 | SEQ ID NO: 26 |
| 151 | | SEQ ID NO: 28 | | | SEQ ID NO: 25 | |
| 152 | | SEQ ID NO: 28 | | | SEQ ID NO: 25 | SEQ ID NO: 26 |
| 153 | | SEQ ID NO: 28 | | | | SEQ ID NO: 26 |
| 154 | | SEQ ID NO: 28 | SEQ ID NO: 29 | SEQ ID NO: 24 | | |
| 155 | | SEQ ID NO: 28 | SEQ ID NO: 29 | SEQ ID NO: 24 | SEQ ID NO: 25 | |
| 156 | | SEQ ID NO: 28 | SEQ ID NO: 29 | SEQ ID NO: 24 | SEQ ID NO: 25 | SEQ ID NO: 26 |
| 157 | | SEQ ID NO: 28 | SEQ ID NO: 29 | | SEQ ID NO: 25 | |
| 158 | | SEQ ID NO: 28 | SEQ ID NO: 29 | | SEQ ID NO: 25 | SEQ ID NO: 26 |
| 159 | | SEQ ID NO: 28 | SEQ ID NO: 29 | | | SEQ ID NO: 26 |
| 160 | | | SEQ ID NO: 29 | SEQ ID NO: 24 | | |
| 161 | | | SEQ ID NO: 29 | SEQ ID NO: 24 | SEQ ID NO: 25 | |
| 162 | | | SEQ ID NO: 29 | SEQ ID NO: 24 | SEQ ID NO: 25 | SEQ ID NO: 26 |
| 163 | | | SEQ ID NO: 29 | | SEQ ID NO: 25 | |
| 164 | | | SEQ ID NO: 29 | | SEQ ID NO: 25 | SEQ ID NO: 26 |
| 165 | | | SEQ ID NO: 29 | | | SEQ ID NO: 26 |
| 166 | SEQ ID NO: 37 | | | | | |
| 167 | SEQ ID NO: 37 | SEQ ID NO: 38 | | | | |
| 168 | SEQ ID NO: 37 | SEQ ID NO: 38 | SEQ ID NO: 39 | | | |
| 169 | | SEQ ID NO: 38 | | | | |
| 170 | | SEQ ID NO: 38 | SEQ ID NO: 39 | | | |
| 171 | | | SEQ ID NO: 39 | | | |
| 172 | | | | SEQ ID NO: 34 | | |
| 173 | | | | SEQ ID NO: 34 | SEQ ID NO: 35 | |
| 174 | | | | SEQ ID NO: 34 | SEQ ID NO: 35 | SEQ ID NO: 36 |
| 175 | | | | | SEQ ID NO: 35 | |
| 176 | | | | | SEQ ID NO: 35 | SEQ ID NO: 36 |
| 177 | | | | | | SEQ ID NO: 36 |
| 178 | SEQ ID NO: 37 | | | SEQ ID NO: 34 | | |
| 179 | SEQ ID NO: 37 | | | SEQ ID NO: 34 | SEQ ID NO: 35 | |
| 180 | SEQ ID NO: 37 | | | SEQ ID NO: 34 | SEQ ID NO: 35 | SEQ ID NO: 36 |
| 181 | SEQ ID NO: 37 | | | | SEQ ID NO: 35 | |
| 182 | SEQ ID NO: 37 | | | | SEQ ID NO: 35 | SEQ ID NO: 36 |
| 183 | SEQ ID NO: 37 | | | | | SEQ ID NO: 36 |
| 184 | SEQ ID NO: 37 | SEQ ID NO: 38 | | SEQ ID NO: 34 | | |
| 185 | SEQ ID NO: 37 | SEQ ID NO: 38 | | SEQ ID NO: 34 | SEQ ID NO: 35 | |
| 186 | SEQ ID NO: 37 | SEQ ID NO: 38 | | SEQ ID NO: 34 | SEQ ID NO: 35 | SEQ ID NO: 36 |
| 187 | SEQ ID NO: 37 | SEQ ID NO: 38 | | | SEQ ID NO: 35 | |
| 188 | SEQ ID NO: 37 | SEQ ID NO: 38 | | | SEQ ID NO: 35 | SEQ ID NO: 36 |
| 189 | SEQ ID NO: 37 | SEQ ID NO: 38 | | | | SEQ ID NO: 36 |
| 190 | SEQ ID NO: 37 | SEQ ID NO: 38 | SEQ ID NO: 39 | SEQ ID NO: 34 | | |
| 191 | SEQ ID NO: 37 | SEQ ID NO: 38 | SEQ ID NO: 39 | SEQ ID NO: 34 | SEQ ID NO: 35 | |
| 192 | SEQ ID NO: 37 | SEQ ID NO: 38 | SEQ ID NO: 39 | SEQ ID NO: 34 | SEQ ID NO: 35 | SEQ ID NO: 36 |
| 193 | SEQ ID NO: 37 | SEQ ID NO: 38 | SEQ ID NO: 39 | | SEQ ID NO: 35 | |
| 194 | SEQ ID NO: 37 | SEQ ID NO: 38 | SEQ ID NO: 39 | | SEQ ID NO: 35 | SEQ ID NO: 36 |
| 195 | SEQ ID NO: 37 | SEQ ID NO: 38 | SEQ ID NO: 39 | | | SEQ ID NO: 36 |
| 196 | | SEQ ID NO: 38 | | SEQ ID NO: 34 | | |
| 197 | | SEQ ID NO: 38 | | SEQ ID NO: 34 | SEQ ID NO: 35 | |
| 198 | | SEQ ID NO: 38 | | SEQ ID NO: 34 | SEQ ID NO: 35 | SEQ ID NO: 36 |
| 199 | | SEQ ID NO: 38 | | | SEQ ID NO: 35 | |
| 200 | | SEQ ID NO: 38 | | | SEQ ID NO: 35 | SEQ ID NO: 36 |
| 201 | | SEQ ID NO: 38 | | | | SEQ ID NO: 36 |
| 202 | | SEQ ID NO: 38 | SEQ ID NO: 39 | SEQ ID NO: 34 | | |

TABLE A-continued

| | Light Chain | | | Heavy Chain | | |
|---|---|---|---|---|---|---|
| Antibody | CDR1 | CDR2 | CDR3 | CDR1 | CDR2 | CDR3 |
| 203 | | SEQ ID NO: 38 | SEQ ID NO: 39 | SEQ ID NO: 34 | SEQ ID NO: 35 | |
| 204 | | SEQ ID NO: 38 | SEQ ID NO: 39 | SEQ ID NO: 34 | SEQ ID NO: 35 | SEQ ID NO: 36 |
| 205 | | SEQ ID NO: 38 | SEQ ID NO: 39 | | SEQ ID NO: 35 | |
| 206 | | SEQ ID NO: 38 | SEQ ID NO: 39 | | SEQ ID NO: 35 | SEQ ID NO: 36 |
| 207 | | SEQ ID NO: 38 | SEQ ID NO: 39 | | | SEQ ID NO: 36 |
| 208 | | | SEQ ID NO: 39 | SEQ ID NO: 34 | | |
| 209 | | | SEQ ID NO: 39 | SEQ ID NO: 34 | SEQ ID NO: 35 | |
| 210 | | | SEQ ID NO: 39 | SEQ ID NO: 34 | SEQ ID NO: 35 | SEQ ID NO: 36 |
| 211 | | | SEQ ID NO: 39 | SEQ ID NO: 35 | SEQ ID NO: 35 | |
| 212 | | | SEQ ID NO: 39 | | SEQ ID NO: 35 | SEQ ID NO: 36 |
| 213 | | | SEQ ID NO: 39 | | | SEQ ID NO: 36 |
| 214 | SEQ ID NO: 47 | | | | | |
| 215 | SEQ ID NO: 47 | SEQ ID NO: 48 | | | | |
| 216 | SEQ ID NO: 47 | SEQ ID NO: 48 | SEQ ID NO: 49 | | | |
| 217 | | SEQ ID NO: 48 | | | | |
| 218 | | SEQ ID NO: 48 | SEQ ID NO: 49 | | | |
| 219 | | | SEQ ID NO: 49 | | | |
| 220 | | | | SEQ ID NO: 44 | | |
| 221 | | | | SEQ ID NO: 44 | SEQ ID NO: 45 | |
| 222 | | | | SEQ ID NO: 44 | SEQ ID NO: 45 | SEQ ID NO: 46 |
| 223 | | | | | SEQ ID NO: 45 | |
| 224 | | | | | SEQ ID NO: 45 | SEQ ID NO: 46 |
| 225 | | | | | | SEQ ID NO: 46 |
| 226 | SEQ ID NO: 47 | | | SEQ ID NO: 44 | | |
| 227 | SEQ ID NO: 47 | | | SEQ ID NO: 44 | SEQ ID NO: 45 | |
| 228 | SEQ ID NO: 47 | | | SEQ ID NO: 44 | SEQ ID NO: 45 | SEQ ID NO: 46 |
| 229 | SEQ ID NO: 47 | | | | SEQ ID NO: 45 | |
| 230 | SEQ ID NO: 47 | | | | SEQ ID NO: 45 | SEQ ID NO: 46 |
| 231 | SEQ ID NO: 47 | | | | | SEQ ID NO: 46 |
| 232 | SEQ ID NO: 47 | SEQ ID NO: 48 | | SEQ ID NO: 44 | | |
| 233 | SEQ ID NO: 47 | SEQ ID NO: 48 | | SEQ ID NO: 44 | SEQ ID NO: 45 | |
| 234 | SEQ ID NO: 47 | SEQ ID NO: 48 | | SEQ ID NO: 44 | SEQ ID NO: 45 | SEQ ID NO: 46 |
| 235 | SEQ ID NO: 47 | SEQ ID NO: 48 | | | SEQ ID NO: 45 | |
| 236 | SEQ ID NO: 47 | SEQ ID NO: 48 | | | SEQ ID NO: 45 | SEQ ID NO: 46 |
| 237 | SEQ ID NO: 47 | SEQ ID NO: 48 | | | | SEQ ID NO: 46 |
| 238 | SEQ ID NO: 47 | SEQ ID NO: 48 | SEQ ID NO: 49 | SEQ ID NO: 44 | | |
| 239 | SEQ ID NO: 47 | SEQ ID NO: 48 | SEQ ID NO: 49 | SEQ ID NO: 44 | SEQ ID NO: 45 | |
| 240 | SEQ ID NO: 47 | SEQ ID NO: 48 | SEQ ID NO: 49 | SEQ ID NO: 44 | SEQ ID NO: 45 | SEQ ID NO: 46 |
| 241 | SEQ ID NO: 47 | SEQ ID NO: 48 | SEQ ID NO: 49 | | SEQ ID NO: 45 | |
| 242 | SEQ ID NO: 47 | SEQ ID NO: 48 | SEQ ID NO: 49 | | SEQ ID NO: 45 | SEQ ID NO: 46 |
| 243 | SEQ ID NO: 47 | SEQ ID NO: 48 | SEQ ID NO: 49 | | | SEQ ID NO: 46 |
| 244 | | SEQ ID NO: 48 | | SEQ ID NO: 44 | | |
| 245 | | SEQ ID NO: 48 | | SEQ ID NO: 44 | SEQ ID NO: 45 | |
| 246 | | SEQ ID NO: 48 | | SEQ ID NO: 44 | SEQ ID NO: 45 | SEQ ID NO: 46 |
| 247 | | SEQ ID NO: 48 | | | SEQ ID NO: 45 | |
| 248 | | SEQ ID NO: 48 | | | SEQ ID NO: 45 | SEQ ID NO: 46 |
| 249 | | SEQ ID NO: 48 | | | | SEQ ID NO: 46 |
| 250 | | SEQ ID NO: 48 | SEQ ID NO: 49 | SEQ ID NO: 44 | | |
| 251 | | SEQ ID NO: 48 | SEQ ID NO: 49 | SEQ ID NO: 44 | SEQ ID NO: 45 | |
| 252 | | SEQ ID NO: 48 | SEQ ID NO: 49 | SEQ ID NO: 44 | SEQ ID NO: 45 | SEQ ID NO: 46 |
| 253 | | SEQ ID NO: 48 | SEQ ID NO: 49 | | SEQ ID NO: 45 | |
| 254 | | SEQ ID NO: 48 | SEQ ID NO: 49 | | SEQ ID NO: 45 | SEQ ID NO: 46 |
| 255 | | SEQ ID NO: 48 | SEQ ID NO: 49 | | | SEQ ID NO: 46 |
| 256 | | | SEQ ID NO: 49 | SEQ ID NO: 44 | | |
| 257 | | | SEQ ID NO: 49 | SEQ ID NO: 44 | SEQ ID NO: 45 | |
| 258 | | | SEQ ID NO: 49 | SEQ ID NO: 44 | SEQ ID NO: 45 | SEQ ID NO: 46 |
| 259 | | | SEQ ID NO: 49 | | SEQ ID NO: 45 | |
| 260 | | | SEQ ID NO: 49 | | SEQ ID NO: 45 | SEQ ID NO: 46 |
| 261 | | | SEQ ID NO: 49 | | | SEQ ID NO: 46 |

In various embodiments, an antigen binding protein of the disclosure is humanized. For instance, in one embodiment, a humanized antigen binding protein of the disclosure may comprise a light chain variable region comprising SEQ ID NO:7 with zero to two amino acid substitutions, SEQ ID NO:8 with zero to two amino acid substitutions, and SEQ ID NO:9 or SEQ ID NO:10 with zero to two amino acid substitutions, and/or may comprise a heavy chain variable region comprising SEQ ID NO:4 with zero to two amino acid substitutions, SEQ ID NO:5 with zero to two amino acid substitutions, and SEQ ID NO:6 with zero to two amino acid substitutions. In a preferred embodiment, a humanized antigen binding protein of the disclosure may comprise a light chain variable region SEQ ID NO:7 with zero to two amino acid substitutions, SEQ ID NO:8 with zero to two amino acid substitutions, SEQ ID NO:9 or SEQ ID NO:10 with zero to two amino acid substitutions, a heavy chain variable region comprising SEQ ID NO:4 with zero to two amino acid substitutions, SEQ ID NO:5 with zero to two amino acid substitutions, and SEQ ID NO:6 with zero to two amino acid substitutions. In an exemplary embodiment, a humanized antigen binding protein of the disclosure may comprise a light chain variable region comprising SEQ ID NO:7, SEQ ID NO:8, SEQ ID NO:9 or SEQ ID NO:10, and a heavy chain variable region comprising SEQ ID NO:4, SEQ ID NO:5, and SEQ ID NO:6. The disclosure also encompasses the corresponding nucleic acid sequences of SEQ ID NO:4, SEQ ID NO:5, SEQ ID NO:6, SEQ ID NO:7, SEQ ID NO:8, SEQ ID NO:9 and SEQ ID NO:10, which can readily be determined by one of skill in the art, and may be incorporated into a vector or other large DNA molecule, such as a chromosome, in order to express an antigen binding protein of the disclosure.

In various embodiments, an antigen binding protein of the disclosure is humanized. For instance, in one embodiment, a humanized antigen binding protein of the disclosure may comprise a light chain variable region comprising SEQ ID NO:17 with zero to two amino acid substitutions, SEQ ID NO:18 with zero to two amino acid substitutions, and SEQ ID NO:19 with zero to two amino acid substitutions, and/or may comprise a heavy chain variable region comprising SEQ ID NO:14 with zero to two amino acid substitutions, SEQ ID NO:15 with zero to two amino acid substitutions, and SEQ ID NO:16 with zero to two amino acid substitutions. In a preferred embodiment, a humanized antigen binding protein of the disclosure may comprise a light chain variable region SEQ ID NO:17 with zero to two amino acid substitutions, SEQ ID NO:18 with zero to two amino acid substitutions, SEQ ID NO:19 with zero to two amino acid substitutions, a heavy chain variable region comprising SEQ ID NO:14 with zero to two amino acid substitutions, SEQ ID NO:15 with zero to two amino acid substitutions, and SEQ ID NO:16 with zero to two amino acid substitutions. In an exemplary embodiment, a humanized antigen binding protein of the disclosure may comprise a light chain variable region comprising SEQ ID NO:17, SEQ ID NO:18, and SEQ ID NO:19, and a heavy chain variable region comprising SEQ ID NO:14, SEQ ID NO:15, and SEQ ID NO:16. The disclosure also encompasses the corresponding nucleic acid sequences of SEQ ID NO:14, SEQ ID NO:15, SEQ ID NO:16, SEQ ID NO:17, SEQ ID NO:18, and SEQ ID NO:19, which can readily be determined by one of skill in the art. In one embodiment, the disclosure encompasses a light chain nucleotide sequence of SEQ ID NO:23 and/or comprise a heavy chain nucleotide sequence of SEQ ID NO:22 and may be incorporated into a vector or other large DNA molecule, such as a chromosome, in order to express an antigen binding protein of the disclosure.

In various embodiments, an antigen binding protein of the disclosure is humanized. For instance, in one embodiment, a humanized antigen binding protein of the disclosure may comprise a light chain variable region comprising SEQ ID NO:27 with zero to two amino acid substitutions, SEQ ID NO:28 with zero to two amino acid substitutions, and SEQ ID NO:29 with zero to two amino acid substitutions, and/or may comprise a heavy chain variable region comprising SEQ ID NO:24 with zero to two amino acid substitutions, SEQ ID NO:25 with zero to two amino acid substitutions, and SEQ ID NO:26 with zero to two amino acid substitutions. In a preferred embodiment, a humanized antigen binding protein of the disclosure may comprise a light chain variable region SEQ ID NO:27 with zero to two amino acid substitutions, SEQ ID NO:28 with zero to two amino acid substitutions, SEQ ID NO:29 with zero to two amino acid substitutions, a heavy chain variable region comprising SEQ ID NO:24 with zero to two amino acid substitutions, SEQ ID NO:25 with zero to two amino acid substitutions, and SEQ ID NO:26 with zero to two amino acid substitutions. In an exemplary embodiment, a humanized antigen binding protein of the disclosure may comprise a light chain variable region comprising SEQ ID NO:27, SEQ ID NO:28, and SEQ ID NO:29, and a heavy chain variable region comprising SEQ ID NO:24, SEQ ID NO:25, and SEQ ID NO:26. The disclosure also encompasses the corresponding nucleic acid sequences of SEQ ID NO:24, SEQ ID NO:25, SEQ ID NO:26, SEQ ID NO:27, SEQ ID NO:28, and SEQ ID NO:29, which can readily be determined by one of skill in the art. In one embodiment, the disclosure encompasses a light chain nucleotide sequence of SEQ ID NO:33 and/or comprise a heavy chain nucleotide sequence of SEQ ID NO:32 and may be incorporated into a vector or other large DNA molecule, such as a chromosome, in order to express an antigen binding protein of the disclosure.

In various embodiments, an antigen binding protein of the disclosure is humanized. For instance, in one embodiment, a humanized antigen binding protein of the disclosure may comprise a light chain variable region comprising SEQ ID NO:37 with zero to two amino acid substitutions, SEQ ID NO:38 with zero to two amino acid substitutions, and SEQ ID NO:39 with zero to two amino acid substitutions, and/or may comprise a heavy chain variable region comprising SEQ ID NO:34 with zero to two amino acid substitutions, SEQ ID NO:35 with zero to two amino acid substitutions, and SEQ ID NO:36 with zero to two amino acid substitutions. In a preferred embodiment, a humanized antigen binding protein of the disclosure may comprise a light chain variable region SEQ ID NO:37 with zero to two amino acid substitutions, SEQ ID NO:38 with zero to two amino acid substitutions, SEQ ID NO:39 with zero to two amino acid substitutions, a heavy chain variable region comprising SEQ ID NO:34 with zero to two amino acid substitutions, SEQ ID NO:35 with zero to two amino acid substitutions, and SEQ ID NO:36 with zero to two amino acid substitutions. In an exemplary embodiment, a humanized antigen binding protein of the disclosure may comprise a light chain variable region comprising SEQ ID NO:37, SEQ ID NO:38, and SEQ ID NO:39, and a heavy chain variable region comprising SEQ ID NO:34, SEQ ID NO:35, and SEQ ID NO:36. The disclosure also encompasses the corresponding nucleic acid sequences of SEQ ID NO:34, SEQ ID NO:35, SEQ ID NO:36, SEQ ID NO:37, SEQ ID NO:38, and SEQ ID NO:39, which can readily be determined by one of skill in the art. In one embodiment, the disclosure encompasses a light chain nucleotide sequence of SEQ ID NO:43 and/or comprise a heavy chain nucleotide sequence of SEQ ID NO:42 and may be incorporated into a vector or other large DNA molecule, such as a chromosome, in order to express an antigen binding protein of the disclosure.

In various embodiments, an antigen binding protein of the disclosure is humanized. For instance, in one embodiment, a humanized antigen binding protein of the disclosure may comprise a light chain variable region comprising SEQ ID NO:47 with zero to two amino acid substitutions, SEQ ID NO:48 with zero to two amino acid substitutions, and SEQ ID NO:49 with zero to two amino acid substitutions, and/or may comprise a heavy chain variable region comprising SEQ ID NO:44 with zero to two amino acid substitutions, SEQ ID NO:45 with zero to two amino acid substitutions, and SEQ ID NO:46 with zero to two amino acid substitutions. In a preferred embodiment, a humanized antigen binding protein of the disclosure may comprise a light chain variable region SEQ ID NO:47 with zero to two amino acid substitutions, SEQ ID NO:48 with zero to two amino acid substitutions, SEQ ID NO:49 with zero to two amino acid substitutions, a heavy chain variable region comprising SEQ ID NO:44 with zero to two amino acid substitutions, SEQ ID NO:45 with zero to two amino acid substitutions, and SEQ ID NO:46 with zero to two amino acid substitutions. In an exemplary embodiment, a humanized antigen binding protein of the disclosure may comprise a light chain variable region comprising SEQ ID NO:47, SEQ ID NO:48, and SEQ ID NO:49, and a heavy chain variable region comprising SEQ ID NO:44, SEQ ID NO:45, and SEQ ID NO:46. The disclosure also encompasses the corresponding nucleic acid sequences of SEQ ID NO:44, SEQ ID NO:45, SEQ ID NO:46, SEQ ID NO:47, SEQ ID NO:48, and SEQ ID NO:49, which can readily be determined by one of skill in the art. In one embodiment, the disclosure encompasses a light chain nucleotide sequence of SEQ ID NO:53 and/or comprise a heavy chain nucleotide sequence of SEQ ID NO:22 and may be incorporated into a vector or other large DNA molecule, such as a chromosome, in order to express an antigen binding protein of the disclosure.

The disclosure also encompasses a vector comprising a nucleic acid sequence capable of encoding an antigen binding protein of the disclosure. As used herein, a "vector" is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors. An expression vector encoding an antigen binding protein of the disclosure may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding an antigen binding protein of the disclosure that is introduced to the cell may be linear or circular, may be single-stranded or double-stranded, and may be DNA, RNA, or any modification or combination thereof. The disclosure also encompasses a cell line comprising a vector comprising a nucleic acid sequence capable of encoding an antigen binding protein of the disclosure. In some embodiments, the cell line is an immortalized cell line. In preferred embodiments, the cell line is a hybridoma. Methods of generating hybridomas capable of producing antibodies are known in the art.

(a) Detectable Label

In an aspect, an antigen binding protein of the disclosure may be conjugated to a detectable label. A detectable label may be directly conjugated to an antigen binding protein of the disclosure or may be indirectly conjugated to an antigen binding protein of the disclosure. In an embodiment, a detectable label may be complexed with a chelating agent that is conjugated to an antigen binding protein of the disclosure. In another embodiment, a detectable label may be complexed with a chelating agent that is conjugated to a linker that is conjugated to an antigen binding protein of the disclosure. In still another embodiment, a detectable label may be conjugated to a linker that is conjugated to an antigen binding protein of the disclosure. In still yet another embodiment, a detectable label may be indirectly attached to an antigen binding protein of the disclosure by the ability of the label to be specifically bound by a second molecule. One example of this type of an indirectly attached label is a biotin label that can be specifically bound by the second molecule, streptavidin or other biotin binding protein. Single, dual or multiple labeling may be advantageous. An isolated antigen binding protein of the disclosure may be conjugated to one, two, three, four, or five types of detectable labels.

As used herein, a "detectable label" is any type of label which, when attached to an antigen binding protein of the disclosure renders the antigen binding protein detectable. A detectable label may also be toxic to cells or cytotoxic. Accordingly, a detectable label may also be a therapeutic agent or cytotoxic agent. In general, detectable labels may include luminescent molecules, chemiluminescent molecules, fluorochromes, fluorophores, fluorescent quenching agents, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present disclosure.

A detectable label emits a signal that can be detected by a signal transducing machine. In some cases, the detectable label can emit a signal spontaneously, such as when the detectable label is a radionuclide. In other cases the detectable label emits a signal as a result of being stimulated by an external field such as when the detectable label is a relaxivity metal. Examples of signals include, without limitation, gamma rays, X-rays, visible light, infrared energy, and radiowaves. Examples of signal transducing machines include, without limitation, gamma cameras including SPECT/CT devices, PET scanners, fluorimeters, and Magnetic Resonance Imaging (MRI) machines. As such, the detectable label comprises a label that can be detected using magnetic resonance imaging, scintigraphic imaging, ultrasound, or fluorescence. In a specific embodiment, the detectable label comprises a label that can be detected using positron emission tomography, single photon emission computed tomography, gamma camera imaging, or rectilinear scanning.

Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes. $B_{12}$ or an analog thereof can be labeled for fluorescence detection by labeling the agent with a fluorophore using techniques well known in the art (see, e.g., Lohse et al., Bioconj Chem 8:503-509 (1997)). For example, many known dyes are capable of being coupled to $NH_2$-terminal groups. Alternatively, a fluorochrome such as fluorescein may be bound to a lysine residue of a peptide linker. In a specific embodiment, an alkyne modified dye, such an Alexa Fluor dye, may be clicked to an azido modified $B_{12}$ using, for example, Sharpless click chemistry (Kolb et al., *Angew Chem Int Ed* 2001; 40: 2004-2021, which incorporated by reference in its entirety).

A radionuclide may be a γ-emitting radionuclide, Auger-emitting radionuclide, β-emitting radionuclide, an α-emitting radionuclide, or a positron-emitting radionuclide. A radionuclide may be a detectable label and/or a therapeutic agent. Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 77 and 80m, rubidium-82, strontium-89, zirconium-89, yttrium-86 and 90, ruthenium-95, 97, 103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-211, bismuth-212 and 213, lead-212, radium-223, actinium-225, and nitride or oxide forms derived there from. In a specific embodiment, a radionuclide is selected from the group consisting of copper-64, zirconium-89, yttrium-86, yttrium-90, technetium-99m, iodine-125, iodine-131, lutetium-177, rhenium-186 and rhenium-188.

A variety of metal atoms may be used as a detectable label. The metal atom may generally be selected from the group of metal atoms comprised of metals with an atomic number of twenty or greater. For instance, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e. iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine.

The metal atoms may be metal ions in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide. For instance, non-limiting examples of metal oxides may include iron oxide, manganese oxide, or gadolinium oxide. Additional examples may include magnetite, maghemite, or a combination thereof.

In an embodiment where an antigen binding protein of the disclosure is conjugated to a non-radioactive isotope, it may be used in neutron capture therapy (NCT). Neutron capture therapy (NCT) is a noninvasive therapeutic modality for treating locally invasive malignant tumors. NCT is a two-step procedure: first, the subject is injected with a tumor localizing drug containing a non-radioactive isotope that has a high propensity or cross section (σ) to capture slow neutrons. The cross section of the capture agent is many times greater than that of the other elements present in tissues such as hydrogen, oxygen, and nitrogen. In the second step, the subject is radiated with epithermal neutrons, which after losing energy as they penetrate tissue, are absorbed by the capture agent, which subsequently emits high-energy charged particles, thereby resulting in a biologically destructive nuclear reaction. In certain embodiments, the non-radioactive isotope may be boron-10 or gadolinium.

(b) Therapeutic Agent

In an aspect, an antigen binding protein of the disclosure may be conjugated to a therapeutic agent, such that the therapeutic agent can be selectively targeted to a cell expressing TIP1. In a specific embodiment, the therapeutic agent can be selectively targeted to an irradiated tumor cell expressing TIP1. The therapeutic agent may be directly conjugated to an antigen binding protein of the disclosure or may be indirectly conjugated to an antigen binding protein of the disclosure. In an embodiment, the therapeutic agent may be complexed with a chelating agent that is conjugated to an antigen binding protein of the disclosure. In another embodiment, the therapeutic agent may be complexed with a chelating agent that is conjugated to a linker that is conjugated to an antigen binding protein of the disclosure. In still another embodiment, the therapeutic agent may be conjugated to a linker that is conjugated to an antigen binding protein of the disclosure. In still yet another embodiment, the therapeutic agent may be conjugated to a linker that is conjugated to a chelating agent that is complexed with a detectable label and conjugated to an antigen binding protein of the disclosure.

A "therapeutic agent" is any compound known in the art that is used in the detection, diagnosis, or treatment of a condition or disease. Such compounds may be naturally-occurring, modified, or synthetic. Non-limiting examples of therapeutic agents may include drugs, therapeutic compounds, toxins, genetic materials, metals (such as radioactive isotopes), proteins, peptides, carbohydrates, lipids, steroids, nucleic acid based materials, or derivatives, analogues, or combinations thereof in their native form or derivatized with hydrophobic or charged moieties to enhance incorporation or adsorption into a cell. Such therapeutic agents may be water soluble or may be hydrophobic.

Non-limiting examples of therapeutic agents may include immune-related agents, thyroid agents, respiratory products, antineoplastic agents, anti-helmintics, anti-malarials, mitotic inhibitors, hormones, toxins, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Non-limiting examples of therapeutic agents are described below. In a specific embodiment, a therapeutic agent may be a compound used in the detection diagnosis or treatment of cancer. The therapeutic agent preferably reduces or interferes with tumor growth or otherwise reduces the effect of the tumor within the body or organism. A therapeutic agent that reduces the symptoms produced by the tumor or reduces tumor growth is suitable for the present disclosure. Additionally, any therapeutic agent that reduces the symptoms associated with tumor cell growth will work for purposes of the present disclosure.

An antigen binding protein of the disclosure may be conjugated to one, two, three, four, or five therapeutic agents. A linker may or may not be used to conjugate a therapeutic agent to an antigen binding protein of the disclosure. Generally speaking, the conjugation should not interfere with the antigen binding protein binding to TIP1. In some instances, an antigen binding protein of the disclosure may be generated with a cleavable linkage between the antigen binding protein and therapeutic agent. Such a linker may allow release of the therapeutic agent at a specific cellular location. In other instances, an antigen binding protein of the disclosure may be generated with an enzyme linked to it to create a prodrug. For example, cytidine deaminase may be linked to an antigen binding protein of the disclosure. The cytidine deaminase then cleaves the prodrug to create a cytotoxic drug.

A therapeutic agent of the disclosure may be a toxin. The terra "toxin" means the toxic material or product of plants, animals, microorganisms (including, but not limited to, bacteria, viruses, fungi, rickettsiae or protozoa), or infectious substances, or a recombinant or synthesized molecule, whatever their origin and method of production. A toxin may be a small molecule, peptide, or protein that is capable of causing disease on contact with or absorption by body tissues interacting with biological macromolecules such as enzymes or cellular receptors. A toxin may be a "biotoxin" which is used to explicitly identify the toxin as from biological origin. Biotoxins may be further classified into fungal biotoxins, or short mycotoxins, microbial biotoxins, plant biotoxins, short phytotoxins and animal biotoxins. Non-limiting examples of biotoxins include: endotoxins produced by bacteria, such as *Pseudomonas* endotoxin; cyanotoxins produced by cyanobacteria, such as microcystins, nodularins, anatoxin-a, cylindrospermopsins, lyngbyatoxin-a, saxitoxin, lipopolysaccharides, aplysiatoxins, BMAA; dinotoxins produced by dinoflagellates, such as saxitoxins and gonyautoxins; necrotoxins produced by, for example, the brown recluse or "fiddle back" spider, most rattlesnakes and vipers, the puff adder, *Streptococcus pyogenes*; neurotoxins produced by, for example, the black widow spider, most scorpions, the box jellyfish, elapid snakes, the cone snail, the Blue-ringed octopus, venomous fish, frogs, palythoa coral, various different types of algae, cyanobacteria and dinoflagellates, such as botulinum toxin (e.g. Botox), tetanus toxin, tetrodotoxin, chlorotoxin, conotoxin, anatoxin-a, bungarotoxin, caramboxin, curare; myotoxins, found in, for example, snake and lizard venoms; and cytotoxins such as ricin, from castor beans, apitoxin, from honey bees, and T-2 mycotoxin, from certain toxic mushrooms. In certain embodiments, a toxin is a cytotoxin. In an embodiment, a cytotoxin is an endotoxin from *Pseudomonas*.

A therapeutic agent of the disclosure may be a small molecule therapeutic, a therapeutic antibody, a therapeutic nucleic acid, or a chemotherapeutic agent. Non-limiting examples of therapeutic antibodies may include muromomab, abciximab, rituximab, daclizumab, basiliximab, palivizumab, infliximab, trastuzumab, etanercept, gemtuzumab, alemtuzumab, ibritomomab, adalimumab, alefacept, omalizumab, tositumomab, efalizumab, cetuximab, bevacizumab, natalizumab, ranibizumab, panitumumab, eculizumab, and certolizumab. A representative therapeutic nucleic acid may encode a polypeptide having an ability to induce an immune response and/or an anti-angiogenic response in vivo. Representative therapeutic proteins with immunostimulatory effects include but are not limited to cytokines (e.g., an interleukin (IL) such as IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein. Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (lngber et al., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991). Representative proteins with both immunostimulatory and anti-angiogenic activities may include ID 2, interferon-γ, or a chemokine. Other therapeutic nucleic acids that may be useful for cancer therapy include but are not limited to nucleic acid sequences encoding tumor suppressor gene products/antigens, antimetabolites, suicide gene products, and combinations thereof.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. A cytotoxic agent is any naturally-occurring, modified, or synthetic compound that is toxic to tumor cells. Such agents are useful in the treatment of neoplasms, and in the treatment of other symptoms or diseases characterized by cell proliferation or a hyperactive cell population. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof. In an exemplary embodiment, the chemotherapeutic agent is selected from the group consisting of liposomal doxorubicin and nanoparticle albumin docetaxel.

Non-limiting examples of suitable alkylating agents may include altretamine, benzodopa, busulfan, carboplatin, carboquone, carmustine (BCNU), chlorambucil, chlornaphazine, cholophosphamide, chlorozotocin, cisplatin, cyclophosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites may include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcitabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics may include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents may include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors may include, but are not limited to, amsacrine, etoposide (VP-16), irinotecan, mitoxantrone, RFS 2000, teniposide, and topotecan.

Non-limiting examples of suitable anti-hormonal agents may include aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents may include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Non limiting examples of angiogeneisis inhibitors may include angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide.

Non limiting examples of growth inhibitory polypeptides may include bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1 BB ligand, and Apo-1 ligand.

Non-limiting examples of photodynamic therapeutic agents may include aminolevulinic acid, methyl aminolevulinate, retinoids (alitretinon, tamibarotene, tretinoin), and temoporfin.

Other antineoplastic agents may include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Also included are pharmaceutically acceptable salts, acids, or derivatives of any of the above listed agents. The dose of the chemotherapeutic agent can and will vary depending upon the agent and the type of tumor or neoplasm. A skilled practitioner will be able to determine the appropriate dose of the chemotherapeutic agent.

Other therapeutic agents may comprise a virus or a viral genome such as an oncolytic virus. An oncolytic virus comprises a naturally occurring virus that is capable of killing a cell in the target tissue (for example, by lysis) when it enters such a cell.

(c) Delivery Vehicle

An antigen binding protein of the disclosure may be conjugated to a vehicle for cellular delivery. In these embodiments, typically an antibody of the disclosure, which may or may not be conjugated to a detectable label and/or therapeutic agent, is encapsulated in a suitable vehicle to either aid in the delivery of the compound to target cells, to increase the stability of the antibody, or to minimize potential toxicity of the antigen binding protein. As will be appreciated by a skilled artisan, a variety of vehicles are suitable for delivering an antigen binding protein of the disclosure. Non-limiting examples of suitable structured fluid delivery systems may include nanoparticles, liposomes, microemulsions, micelles, dendrimers and other phospholipid-containing systems. Methods of incorporating antibodies into delivery vehicles are known in the art. Although various embodiments are presented below, it will be appreciate that other methods known in the art to incorporate an antigen binding protein of the disclosure into a delivery vehicle are contemplated.

In one alternative embodiment, a liposome delivery vehicle may be utilized. Liposomes, depending upon the embodiment, are suitable for delivery of the antigen binding protein of the disclosure in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the antigen binding protein of the disclosure may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the antigen binding protein of the disclosure may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, an antigen binding protein of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The antigen binding protein of the disclosure may be encapsulated in a microemulsion by any method generally known in the art.

In yet another embodiment, an antigen binding protein of the disclosure may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate antigen binding protein of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

TABLE B

| SEQ ID NO: | Description | SEQUENCE |
|---|---|---|
| 1 | TIP1 | MSYIPGQPVT AVVQRVEIHK LRQGENLILG FSIGGGIDQD PSQNPFSEDK TDKGIYVTRV SEGGPAEIAG LQIGDKIMQV NGWDMTMVTH DQARKRLTKR SEEVVRLLVT RQSLQKAVQQ SMLS |
| 2 | PDZ domain of TIP1 | VQRVEIHK LRQGENLILG FSIGGGIDQD PSQNPFSEDK TDKGIYVTRV SEGGPAEIAG LQIGDKIMQV NGWDMTMVTH DQARKRLTKR SEEVVRLLVT RQ |
| 3 | PDZ domain epitope | IDQD PSQNPFSEDK TDKG |
| 4 | G14/H2: CDR1-HC | GFTFSNYA |
| 5 | G14/H2: CDR2-HC | VSGSGAST |
| 6 | G14/H2: CDR3-HC | AKHGTRFDYWGQRTLVTVS |
| 7 | G14/H2: CDR1-LC | QSVSSY |
| 8 | G14/H2: CDR2-LC | GAS |
| 9 | G14: CDR3-LC | QQT |
| 10 | H2: CDR3-LC | QQTYPLTFGRWKIK |
| 11 | PDZ domain epitope | IDQD PSQNPF |
| 12 | sgRNA1 | CCAGGGTATTTATGTCACAC |
| 13 | sgRNA2 | CATTGGAGGTGGAATCGACC |
| 14 | 2F10: CDR1-HC | SSGIS |
| 15 | 2F10: CDR2-HC | EIYPRSGNTYYNEKFKA |
| 16 | 2F10: CDR3-HC | SKTYYSKYGGFFDY |
| 17 | 2F10: CDR1-LC | RSSQSIVHGNGNTYLE |
| 18 | 2F10: CDR2-LC | VSNRFS |
| 19 | 2F10: CDR3-LC | FQGSHVPPT |
| 20 | 2F10-HC aa with leader sequence | MEWIWIFLFILSGTAGVQSQVQLQQSGAELARPGASVKLSCKASGYTFTSSGISWVIQKTGQ GLEWIGEIYPRSGNTYYNEKFKAKAALTADKSSSTAHMELRSLTSEDSAVYFCARSKTYYSK YGGFFDYWGQGTPLTVSS |
| 21 | 2F10-LC aa with leader sequence | MKLPVRLLVLMFWIPASSSDVLMTQTPLSLPVSLGDQASISCRSSQSIVHGNGNTYLEWYLQ KPGQSPKLLIHKVSNRFSGVPDRFSGSGSGTDFTLKISRVEAEDLGVYYCFQGSHVPPTFG GGTKLEIK |
| 22 | 2F10-HC DNA with leader sequence | ATGGAATGGATCTGGATCTTTCTCTTCATCCTGTCAGGAACTGCAGGTGTCCAATCCCAG GTTCAGCTGCAGCAGTCTGGAGCTGAGCTGGCGAGGCCTGGGGCTTCAGTGAAGCTGT CCTGCAAGGCTTCTGGCTACACCTTCACAAGCTCTGGTATAAGCTGGGTGATTCAAAAA ACTGGACAGGGCCTTGAGTGGATTGGAGAGATTTATCCTAGAAGTGGTAATACTTACTA CAATGAGAAGTTCAAGGCCAAGGCCGCACTGACTGCAGACAAATCCTCCAGCACAGCG CACATGGAGCTCCGCAGCCTGACATCTGAGGACTCTGCGGTCTATTTCTGTGCAAGATC GAAGACCTACTATAGTAAATACGGAGGGTTTTTTGACTACTGGGGCCAAGGCACCCCTC TCACAGTCTCCTCA |
| 23 | 2F10-LC DNA | ATGAAGTTGCCTGTTAGGCTGTTGGTGCTGATGTTCTGGATTCCTGCTTCCAGCAGTGAT GTTTTGATGACCCAAACTCCACTCTCCCTGCCTGTCAGTCTTGGAGATCAAGCCTCCATC TCTTGCAGATCTAGTCAGAGCATTGTACATGGTAATGGAAACACCTATTTAGAATGGTAC |

TABLE B-continued

| SEQ ID NO: | Description | SEQUENCE |
|---|---|---|
| | | CTGCAGAAACCAGGCCAGTCTCCAAAGCTCCTGATCCACAAAGTTTCCAACCGATTTTCT GGGGTCCCAGACAGGTTCAGTGGCAGTGGATCAGGGACAGATTTCACACTCAAGATCA GCAGAGTGGAGGCTGAGGATCTGGGAGTTTATTACTGCTTTCAAGGTTCACATGTTCCT CCCACGTTCGGAGGGGGGACCAAGCTGGAAATAAAA |
| 24 | 3D6: CDR1-HC | NSGIS |
| 25 | 3D6: CDR2-HC | EIYPGSGNIYYNEKFKV |
| 26 | 3D6: CDR3-HC | SRTYYSKYGGLFDY |
| 27 | 3D6: CDR1-LC | RSSGSLLHNNGNTYLE |
| 28 | 3D6: CDR2-LC | KVSSRFS |
| 29 | 3D6: CDR3-LC | FQGSHIPPT |
| 30 | 3D6-HC aa with leader sequence | MEWIWIFLFILSGTAGVQSQVQLHQSGAELARPGAAVKLTCKASGYTLTNSGISWVKQRSG QGLEWIGEIYPGSGNIYYNEKFKVKATLTADKSSSTTYMELRSLTSEDSAVYFCARSRTYYSK YGGLFDYWGQGATLTVSS |
| 31 | 3D6-LC aa with leader sequence | MKLPVRLLVLMFWIPGSNSDVLMTQTPLSLPVRLGDQASISCRSSQSLLHNNGNTYLEWYL QKPGQSPKLLIYKVSSRFSGVPDRFSGSGSGTDFTLKISRVEAKDLGVYYCFQGSHIPPTFG GGTKLEIK |
| 32 | 3D6-HC DNA with leader sequence | ATGGAATGGATCTGGATCTTTCTCTTCATCCTGTCAGGAACTGCAGGTGTCCAATCCCAG GTTCAGTTGCACCAGTCAGGAGCTGAGCTGGCGGAGGCCTGGGGCTGCAGTGAAGCTGA CCTGCAAGGCTTCTGGCTACACCCTCACAAACTCCGGTATAAGCTGGGTGAAGCAGAGA TCTGGACAGGGCCTTGAGTGGATTGGAGAGATTTATCCTGGAAGTGGTAATATTTACTAT AATGAGAAGTTCAAGGTCAAGGCCACACTGACTGCAGACAAATCCTCCAGTACAACGTA CATGGAGCTCCGCAGCCTGACATCTGAGGACTCTGCGGTCTATTTCTGTGCAAGATCGA GGACCTACTATAGTAAATATGGAGGGCTTTTTGACTACTGGGGCCAGGGCGCCACTCTC ACTGTCTCCTCA |
| 33 | 3D6-LC DNA with leader sequence | ATGAAGTTGCCTGTTAGGCTGTTGGTGCTGATGTTCTGGATTCCTGGTTCCAACAGTGAT GTTTTGATGACCCAAACTCCACTCTCCCTGCCTGTCGTCTTGGAGATCAAGCCTCCATC TCTTGCAGATCTAGTCAGAGCCTTCTACATAATAATGGAAACACCTATTTAGAATGGTAC CTGCAGAAACCAGGCCAGTCTCCAAAGCTCCTGATCTACAAAGTTTCCAGCCGATTTTCT GGGGTCCCAGACAGGTTCAGTGGCAGTGGATCAGGGACAGATTTCACACTCAAGATCA GCAGAGTGGAGGCTAAGGATCTGGGAGTTTATTACTGCTTTCAAGGTTCACATATTCCTC CCACGTTCGGAGGGGGGACCAAGCTGGAAATAAAA |
| 34 | 7H5: CDR1-HC | SSGIS |
| 35 | 7H5: CDR2-HC | EIYPRSGNTYYNEKFKG |
| 36 | 7H5: CDR3-HC | SKTFYSKYGGVFDYW |
| 37 | 7H5: CDR1-LC | AGATCTAGTCAGAACATTGTACATAATAATGGAAACACCTATTTAGAT |
| 38 | 7H5: CDR2-LC | AAAGTTTCCAACCGATTTTCG |
| 39 | 7H5: CDR3-LC | TTTCAAGGTTCACATGTTCCTCCCACG |
| 40 | 7H5-HC aa with leader sequence | MERIWIFLFILSGTAGVQSQAQLQQSGAELARPGASVRLSCKASGYILTSSGISWVKQRTGQ GLEWIGEIYPRSGNTYYNEKFKGKATLTADKSSSIAYMDLRTLTSEDSAVYFCARSKTFYSKY GGVFDYWGQGTTLTVSS |
| 41 | 7H5-LC aa with leader sequence | MKLPVRLLVLMFWIPASSSDVLMTQTPLSLPVSLGDQASISCRSSQNIVHNNGNTYLDWYLQ KPGQSPKLLIYKVSNRFSGVPDRFSGSGSGADFTLKISRVEAEDLGVYYCFQGSHVPPTFG GGTKLEIK |
| 42 | 7H5-HC DNA with | ATGGAAAGGATCTGGATCTTTCTCTTCATCCTGTCAGGAACTGCAGGTGTCCAATCCCA GGCTCAGCTGCAGCAGTCTGGAGCTGAACTGGCGAGGCCTGGGGCTTCAGTGAGGCT |

TABLE B-continued

| SEQ ID NO: | Description | SEQUENCE |
|---|---|---|
| | leader sequence | GTCCTGCAAGGCTTCTGGCTACATCCTCACAAGTTCTGGTATAAGCTGGGTGAAGCAGA GAACTGGACAGGGCCTTGAGTGGATTGGAGAGATTTATCCTAGAAGTGGCAATACTTAC TACAATGAGAAGTTCAAGGGCAAGGCCACACTGACTGCAGACAAATCCTCCAGTATAGC GTACATGGACCTCCGCACCCTGACATCTGAGGACTCTGCGGTCTATTTCTGCGCAAGAT CGAAGACGTTCTATAGTAAATACGGAGGGGTTTTTGACTACTGGGGCCAAGGCACCACT CTCACAGTCTCCTCA |
| 43 | 7H5-LC DNA with leader sequence | ATGAAGTTGCCTGTTAGGCTGTTGGTGCTGATGTTCTGGATTCCTGCTTCCAGCAGTGAT GTTTTGATGACCCAAACTCCACTCTCCCTGCCTGTCAGTCTTGGAGATCAAGCCTCCATC TCTTGCAGATCTAGTCAGAACATTGTACATAATAATGGAAACACCTATTTAGATTGGTACC TGCAGAAACCAGGCCAGTCTCCAAAGCTCCTGATCTACAAAGTTTCCAACCGATTTTCG GGGGTCCCAGACAGGTTCAGTGGCAGTGGATCAGGGGCAGATTTCACACTCAAGATCA GCAGAGTGGAGGCTGAGGATCTGGGAGTTTATTACTGCTTTCAAGGTTCACATGTTCCT CCCACGTTCGGAGGGGGGACCAAGCTGGAAATAAAA |
| 44 | 4612: CDR1-HC | SYGIS |
| 45 | 4612: CDR2-HC | EIYFRSGNIYYNEKFKG |
| 46 | 4612: CDR3-HC | SKTFYSNYGGVFDY |
| 47 | 4612: CDR1-LC | AGATCTAGTCGGAGCATTGTTCATAATAATGGAAACACCTATTTAGAA |
| 48 | 4612: CDR2-LC | AAAGTTTCCAACCGATTTTCT |
| 49 | 4612: CDR3-LC | TTTCAAGGTTCACATGTTCCTCCCACG |
| 50 | 4612-HC aa with leader sequence | MEWIWIFLFILSGTAGVHSQFQLQQSGAELARPGASVKLSCKASGYTFTSYGISWVKQRTG QGLEWIGEIYFRSGNIYYNEKFKGKATLTADKSSSTAYMELRSLTSEDSAVYFCARSKTFYSN YGGVFDYWGQGTTLTVSS |
| 51 | 4612-LC aa with leader sequence | MKLPVRLLVLMFWIPVSTCDVLVTQTPLSLPVSLGDQASISCRSSRSIVHNNGNTYLEWYLQ KPGQSPKLLIYKVSNRFSGVPDRFSGSGSGTDFTLKISRVEAEDLGVYYCFQGSHVPPTFGG GTRLEIK |
| 52 | 4612-HC DNA with leader sequence | ATGGAATGGATCTGGATCTTTCTCTTCATCCTGTCAGGAACTGCAGGTGTCCACTCCCA GTTTCAACTACAGCAGTCTGGAGCTGAGCTGGCGAGGCCTGGGGCTTCAGTGAAGCTG TCCTGCAAGGCTTCTGGCTACACCTTCACAAGCTATGGTATAAGCTGGGTGAAGCAGAG AACTGGACAGGGCCTTGAGTGGATTGGAGAGATTTATTTTAGAAGTGGTAATATTTACTA CAATGAGAAATTTAAGGGCAAGGCCACACTGACTGCAGACAAATCCTCCAGCACAGCGT ACATGGAGCTCCGCAGCCTGACATCTGAGGACTCTGCGGTCTATTTCTGTGCAAGATCG AAGACCTTCTATAGTAACTACGGAGGGGTTTTTGACTACTGGGGCCAAGGCACCACTCT CACAGTCTCCTCA |
| 53 | 4B12-LC DNA with leader sequence | ATGAAGTTGCCTGTTAGGCTGTTGGTGCTGATGTTCTGGATTCCTGTTTCCACCTGTGAT GTTTTGGTGACCCAAACTCCACTCTCCCTGCCTGTCAGTCTTGGAGATCAAGCCTCCAT CTCTTGCAGATCTAGTCGGAGCATTGTTCATAATAATGGAAACACCTATTTAGAATGGTA CCTGCAGAAACCAGGCCAGTCTCCAAAGCTCCTGATCTACAAAGTTTCCAACCGATTTTC TGGGGTCCCAGACAGGTTCAGTGGCAGTGGATCAGGGACAGATTTCACACTCAAGATCA GCAGAGTGGAGGCTGAGGATCTGGGAGTTTATTACTGCTTTCAAGGTTCACATGTTCCT CCCACGTTCGGAGGGGGGACCAGGCTGGAAATAAAA |

II. Methods

In an aspect, the present disclosure provides anti-TIP1 antigen binding proteins to detect TIP1 in vitro and/or in vivo. For example, anti-TIP1 antigen binding proteins may be used to detect and measure the amount of TIP1 in a biological sample. Alternatively, anti-TIP1 antigen binding proteins may be used to detect and measure the amount of TIP1 in a subject. In another aspect, the present disclosure provides anti-TIP1 antigen binding proteins that can be used to provide tumor specific delivery, for instance, of drugs, therapeutic agents or imaging agents as well as enhancing the efficacy of radiotherapy. In still another aspect, the present disclosure provides anti-TIP1 antigen binding proteins that can be used to detect a tumor in a subject.

(a) Methods to Detect and Measure TIP1 in a Biological Sample

In an aspect, the disclosure provides means to detect TIP1 in a sample. In another aspect, the disclosure provides means to measure the amount of TIP1 in a sample. The method generally comprises (i) obtaining a sample from, and (ii) detecting and/or measuring the amount of TIP1 in the sample using an antigen binding protein that specifically binds the PDZ domain of TIP1. Suitable antigen binding proteins are described above in Section I. The sample may be obtained from a subject (i.e. biological sample) or may be an immortalized cell line.

As used herein, the term "biological sample" refers to a sample obtained from a subject. Any biological sample containing TIP1 is suitable. Numerous types of biological samples are known in the art. Suitable biological sample may include, but are not limited to, tissue samples or bodily fluids. In some embodiments, the sample may be a bodily fluid comprising a cell expressing TIP on the cell surface. Non-limiting examples of suitable bodily fluids include blood, plasma, serum, lung aspirate, pleural fluid, and sputum. The fluid may be used "as is", the cellular components may be isolated from the fluid, or a protein fraction may be isolated from the fluid using standard techniques. In preferred embodiments, the biological sample is a tissue sample such as a tissue biopsy. The tissue biopsy may be a biopsy of tumor. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. The sample may also be primary and/or transformed cell cultures derived from tissue from the subject.

Suitable subjects include, but are not limited to, a human, a livestock animal, a companion animal, a lab animal, and a zoological animal. A subject may or may not be known to have a tumor comprising a cell expressing TIP1 on the cell surface. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that TIP1 can be accurately detected and the amount measured according to the disclosure.

Once a sample is obtained, it is processed in vitro to detect and measure the amount of TIP using an anti-TIP1 antigen binding protein of the disclosure. All suitable methods for detecting and measuring an amount of protein using an antigen binding protein (i.e. antibody) known to one of skill in the art are contemplated within the scope of the disclosure. Methods for detecting and measuring an amount of protein using an antigen binding protein (i.e. "antibody-based methods") are well known in the art. Non-limiting examples include an ELISA, a sandwich immunoassay, a radioimmunoassay, an immunoblot or Western blot, flow cytometry, immunohistochemistry, and an array.

In general, an antibody-based method of detecting and measuring an amount of TIP1 comprises contacting some of the sample, or all of the sample, comprising TIP1 with an anti-TIP1 antigen binding protein of the disclosure under conditions effective to allow for formation of a complex between the antigen binding protein and the TIP1 protein. Typically, the entire sample is not needed, allowing one skilled in the art to repeatedly detect and measure the amount of TIP1 in the sample. The method may occur in solution, or the antigen binding protein or TIP1 protein comprising the sample may be immobilized on a solid surface. Non-limiting examples of suitable surfaces may include microtitre plates, test tubes, slides, beads, resins, and other polymers. Attachment to the substrate may occur in a wide variety of ways, as will be appreciated by those in the art. For example, the substrate and the antigen binding protein may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antigen binding protein may be attached directly using the functional groups or indirectly using linkers. An anti-TIP1 antigen binding protein of the disclosure may also be attached to the substrate non-covalently. For example, a biotinylated anti-TIP1 antigen binding protein of the disclosure may be prepared, which may bind to surfaces covalently coated with streptavidin, resulting in attachment. Alternatively, an antigen binding protein may be synthesized on the surface using techniques such as photopolymerization and photolithography.

Contacting the sample with an antigen binding protein under effective conditions for a period of time sufficient to allow formation of a complex generally involves adding the anti-TIP1 antigen binding protein of the disclosure to the sample and incubating the mixture for a period of time long enough for the anti-TIP1 antigen binding protein to bind to any antigen present. After this time, the complex will be washed and the complex may be detected and the amount measured by any method well known in the art. Methods of detecting and measuring an amount of an antigen binding protein—polypeptide complex are generally based on the detection of a label or marker. The term "label", as used herein, refers to any substance attached to an antigen binding protein, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase, and luciferase). Methods of detecting and measuring an amount of an antigen binding protein-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antigen binding protein. Unbound analyte is washed away and the bound analyte is measured. In a non-competitive immunoassay, the antigen binding protein is labeled, not the analyte. Non-competitive immunoassays may use one antigen binding protein (e.g. the capture antibody is labeled) or more than one antigen binding protein (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antigen binding protein to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

(b) Tumor Specific Delivery

In another aspect, the present disclosure provides a method of delivering a therapeutic agent to a cell expressing TIP1. Accordingly, an antigen binding protein of the present disclosure, as described in Section I, may be used in treating, stabilizing and preventing cancer and associated diseases in a subject. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. The inventors have shown that an antigen binding protein of the disclosure activates phagocytosis of cells bound by the antigen binding protein thereby reducing the amount of cancer cells expressing TIP1. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of an antibody of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

An antigen binding protein of the present disclosure may be indirectly or directly coupled to radionuclides or chemotherapeutic agents as described above in order to provide specific delivery of radiation and chemotherapy to the site of a tumor. Further, the composition of the present disclosure may be part of a combination therapy. Preferably, a combination therapy would include the use of the antigen binding protein of the present disclosure along with a radiation therapy or chemotherapy course of treatment. It has also been suggested that antigen binding proteins, such as those described herein, may increase the susceptibility of tumor cells to the effects of chemotherapy or radiation. In preferred embodiments, the composition of the disclosure may be used to enhance the efficacy of cancer radiotherapy.

In yet another aspect, the present disclosure provides a method of detecting a tumor in a subject. The method comprises exposing a target area of the subject where the presence of a tumor is suspected to ionizing radiation, administering to the subject a composition to detect the presence of TIP1 in the target area, wherein the composition comprises an antigen binding protein that specifically binds to the PDZ domain of TIP1 exposed on an irradiated cell and is conjugated to a detectable label, and detecting the detectable label to detect the presence of TIP1, wherein the presence of TIP1 indicates the presence of a tumor in the target area of the subject. In preferred embodiments, the method may be used to diagnose or image a cancer in a subject. In some embodiments, a method for detecting a tumor can comprise (a) exposing a suspected tumor to ionizing radiation; (b) biopsying a suspected tumor; (c) contacting an antigen binding protein of the disclosure with the suspected tumor in vitro; and (d) detecting the detectable label, whereby a tumor is diagnosed.

Binding may be detected using microscopy (fluorescent microscopy, confocal microscopy, or electron microscopy), magnetic resonance imaging (including MTI, MRS, DWI and fMRI), scintigraphic imaging (SPECT (Single Photon Emission Computed Tomography), PET (Positron Emission Tomography), gamma camera imaging, and rectilinear scanning), radiography, or ultrasound. The detectable label may be detectable in situ, in vivo, ex vivo, and in vitro.

The antigen binding proteins are as described in Section I above. The subject is described in Section II(a) above. The cancer and the administration of the antigen binding proteins are described below.

i. Tumor

An antigen binding protein of the disclosure may be used to treat or recognize tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a specific embodiment, the neoplasm or cancer is non-small cell lung carcinoma or glioblastoma.

ii. Administration

In an aspect, the method comprises exposing a target area of a subject where the presence of a tumor is suspected to ionizing radiation. Low doses of radiation can be used for selective targeting using the antigen binding protein compositions disclosed herein. In some embodiments, the dose of radiation comprises up to about 2 Gy ionizing radiation. Higher radiation doses can also be used, especially in the case of local radiation treatment as described herein below.

Radiation can be localized to a tumor using conformal irradiation, brachytherapy, or stereotactic irradiation. The threshold dose for inductive changes can thereby be exceeded in the target tissue but avoided in surrounding normal tissues. A "target tissue" as used herein refers to an intended site for accumulation of an antigen binding protein following administration to a subject. For example, the methods disclosed herein can employ a target tissue comprising an irradiated tumor. A "control tissue" as used herein refers to a site suspected to substantially lack binding and/or accumulation of an administered antigen binding protein. For example, in accordance with the methods of the presently disclosed subject matter, a non-irradiated tumor and a non-cancerous tissue are control tissues. In some embodiments, doses of at least about 2 Gy ionizing radiation can be used, and in some embodiments a dose of about 10 Gy to about 20 Gy ionizing radiation can be used. For treatment of a subject having two or more tumors, local irradiation enables differential drug administration and/or dose at each of the two or more tumors. Alternatively, whole body irradiation can be used, as permitted by the low doses of radiation required for targeting of antibodies disclosed herein. Radiotherapy methods suitable for use in the practice of the presently disclosed subject matter can be found in Leibel & Phillips, 1998, among other sources.

In an embodiment, the radiation treatment comprises administration of less than about 2 Gy ionizing radiation. In another embodiment, the radiation treatment comprises at least about 2 Gy ionizing radiation, in some embodiments about 2 Gy to about 3 Gy ionizing radiation, and in some embodiments about 2 Gy to about 6 Gy ionizing radiation. In other embodiments, radiation treatment comprises about 10 Gy to about 20 Gy ionizing radiation.

Administration of a composition to a subject can be performed by irradiating the tumor prior to, concurrent with, or subsequent to administration of a composition of the disclosure. Accordingly, the tumor is irradiated in some embodiments 0 hours to about 24 hours before administration of the composition, and in some embodiments about 4 hours to about 24 hours before administration of the composition.

In certain aspects, a pharmacologically effective amount of an antigen binding protein of the disclosure, including immunologically reactive fragments, may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antigen binding proteins useful in this disclosure, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

The concentration of antigen binding protein in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living patient could be made up to contain 1 mL sterile buffered water of phosphate buffered saline and about 1-1000 mg of any one of or a combination of the humanized antigen binding protein of the present disclosure. In a specific embodiment, the antigen binding protein composition may have 100-300 mg of antigen binding protein per administration. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-TIP1 antigen binding protein concentration. Therapeutic agents of the discovery can be frozen or lyophilized for storage and reconstituted in a suitable sterile carrier prior to use. Lyophilization and reconstitution may lead to varying degrees of antigen binding protein activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antigen binding protein stability (chemical and physical) and comfort to the patient when administered. Generally, a pH between 4 and 8 is tolerated. Doses will vary from individual to individual based on size, weight, and other physiobiological characteristics of the individual receiving the successful administration.

For therapeutic applications, a therapeutically effective amount of a composition of the disclosure is administered to a subject. The term "therapeutically effective amount" as used herein refers to an amount, which has a therapeutic effect or is the amount required to produce a therapeutic effect in a subject. For example, a therapeutically or pharmaceutically effective amount of a composition of the disclosure is the amount of antigen binding protein required to produce a desired therapeutic effect as may be judged by clinical trial results, model animal studies, and/or in vitro studies (e.g. cell lines). The effective or pharmaceutically effective amount depends on several factors, including but not limited to, the cancer, characteristics of the subject (for example height, weight, sex, age and medical history), severity of cancer, and the composition used. For prophylactic treatments, a therapeutically or prophylactically effective amount is that amount which would be effective to prevent cancer or prevent cancer recurrence. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In an aspect, a typical dose contains from about 0.01 mg/kg to about 100 mg/kg of an anti-TIP1 antigen binding protein described herein. Doses can range from about 0.05 mg/kg to about 50 mg/kg, more preferably from about 0.1 mg/kg to about 25 mg/kg.

For diagnostic applications, a detectable amount of a composition of the disclosure is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled antigen binding protein prior to imaging, the route of drug administration, the physical condition and prior medical history of the subject, and the size and longevity of the tumor or suspected tumor. Thus, a detectable amount can vary and can be tailored to a particular application. After study of the present disclosure, and in particular the Examples, it is within the skill of one in the art to determine such a detectable amount.

In some embodiments, when the antigen binding protein is an anti-TIP1 antibody labeled with $^{64}$Cu, the dose administered may be about 0.01, 0.02, 0.03, 0.04, 0.05 0.06, 0.07, 0.08, 0.09, 0.1, 0.011, 0.012, 0.013, 0.013, 0.014, 0.015, 0.016, 0.017, 0.018, 0.019, 0.02, 0.021, 0.022, 0.023, 0.023, 0.024, 0.025, 0.026, 0.027, 0.028, 0.029, 0.03, 0.031, 0.032, 0.033, 0.033, 0.034, 0.035, 0.036, 0.037, 0.038, 0.039, 0.04, 0.041, 0.042, 0.043, 0.043, 0.044, 0.045, 0.046, 0.047, 0.048, 0.049, 0.05, 0.051, 0.052, 0.053, 0.053, 0.054, 0.055, 0.056, 0.057, 0.058, 0.059, 0.06, 0.061, 0.062, 0.063, 0.063, 0.064, 0.065, 0.066, 0.067, 0.068, 0.069, 0.07, 0.071, 0.072, 0.073, 0.073, 0.074, 0.075, 0.076, 0.077, 0.078, 0.079, 0.08, 0.081, 0.082, 0.083, 0.083, 0.084, 0.085, 0.086, 0.087, 0.088, 0.089, 0.09, 0.091, 0.092, 0.093, 0.093, 0.094, 0.095, 0.096, 0.097, 0.098, 0.099, or about 0.1 rem/mCi.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as humanized antigen binding proteins, by suitable adaptation, other effective techniques for administration, such as intraventricular administration, transdermal administration and oral administration may be employed provided proper formulation is utilized herein. In addition, it may be desirable to employ controlled release formulations using biodegradable films and matrices, or osmotic mini-pumps, or delivery systems based on dextran beads, alginate, or collagen.

Additionally, the antigen binding proteins disclosed herein may be used in combination with standard treatment for cancer or standard treatment for symptoms associated with cancer. Suitable therapeutic agents for neoplasms and cancers are known in the art, and will depend upon the type and stage of cancer. Suitable therapeutic agents are described in Section I. Summaries of cancer drugs, including information regarding approved indications, may be found via the National Cancer Institute at the National Institutes of Health (www.cancer.gov/cancertopics/druginfo/alphalist) and the FDA Approved Drug Product database (www.accessdata.fda.gov/scripts/cder/drugsatfda/). In a specific embodiment, the cancer is non-small cell lung carcinoma. Suitable therapeutics agents for the treatment of non-small cell lung carcinoma include, but are not limited to, EGFR inhibitors, VEGF inhibitors, tyrosine kinase inhibitors, and chemotherapeutics. Non-limiting examples of drugs approved for the treatment of NSCLC include methotrexate, Abraxane, Afatinib, Alimta, Avastin, Bevacizumab, Carboplatin, Cisplatin, Crizotinib, Erlotinib hydrochloride, Folex, Folex PFS, gefitinib, Gilotrif, Gemcitabine hydrochloride, Gemzar, Iressa, Methotrexate, Mexate, Mexate-AQ, Paclitaxel, Paclitaxel-albumin stabilized nanoparticle formulation, Paraplat, Paraplatin, Platinol, Tarceva, Taxol, and Xalkori.

III. Kits

In a another aspect, a kit is provided for use in diagnostic or therapeutic embodiments of the invention. The kit includes an antigen binding protein to the invention, and a detectable label, therapeutic agent, chelating agent, and/or a linker, as described in Section I. In an embodiment, each component of the kit (an antigen binding protein and a detectable label, therapeutic agent, chelating agent, and/or linker) is separately packaged in the kit.

In another preferred embodiment, the kit includes a predetermined amount of the antibody and the detectable label, therapeutic agent, chelating agent, and/or linker (e.g., an amount sufficient for diagnosing or treating cancer in a subject). The antigen binding protein and the detectable label, therapeutic agent, chelating agent, and/or linker can be lyophilized to enable long-term storage. The antigen binding protein and detectable label, therapeutic agent, chelating agent, and/or linker may be sealed in a sterilized container. The kit preferably includes instructions for using the kit and its contents.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples 1-6

Glioblastoma multiforme (GBM) and non-small-cell lung cancer (NSCLC) are cancers that are difficult and challenging to treat. Despite advancements in diagnosis and treatment, the 5-year overall survival rate in NSCLC is 15% and in GBM is 5%. Lung cancer is the most common type of malignancy and is one of the leading causes of cancer-related deaths worldwide. According to 2016 cancer statistics, an estimated total of 221,200 new lung cancer cases and 158,040 lung cancer deaths occurred in the United States in 2015. Of all lung cancer cases, 85% are NSCLC. GBM is a highly malignant form of brain tumor with an annual incidence of approximately 12,000 in the United States.

Targeted therapies are gaining importance for cancer treatment since they usually cause less harm to normal cells than chemotherapy or radiation therapy. Monoclonal antibodies and tyrosine kinase inhibitors are the two main types of targeted therapy being used to treat advanced, metastatic, or recurrent NSCLC and GBM. Epidermal growth factor receptor (EGFR) blockers erlotinib, afatinib, and gefitinib; angiogenesis blocker bevacizumab and recently approved PD-1 checkpoint inhibitors nivolumab and pembrolizumab are examples of targeted therapies currently approved for NSCLC. In 2009, bevacizumab was approved for the treatment of GBM patients whose cancers had recurred. Although 26% of patients who received bevacizumab had partial responses, most lasted less than six months, and there was no evidence of improvement in overall survival. Thus, there have been limited improvements in therapeutic efficacy with these targets. For this reason, identifying additional molecular targets in NSCLC and GBM is an important issue.

Tax interacting protein 1 (TIP1) is highly expressed in several different cancers. TIP1 functions in a variety of biological processes through selective interaction with proteins such as β-catenin, FAS, rhotekin, Kir 2.3 and Rho. TIP1 modulates trafficking of intracellular proteins. It is required for the HPV16 E6 oncoprotein-induced cell transformation. It is also important for tumor cell adhesion, migration, and metastasis. TIP1 levels correlated with progression and poor prognosis in several cancers. Furthermore, TIP1 was found to contribute to radio resistance. These data indicate that TIP1 is a plausible molecular target for developing interventions for cancer therapy.

The functional domain of TIP1 involved in protein-protein interactions is the PSD-95/DIgA/ZO-1 (PDZ) domain. The PDZ-domain-containing proteins are involved in cell signaling events as well as membrane protein trafficking in cancer. The PDZ domains normally span 80-100 amino acid residues and are comprised of six β-sheets and two α-helices. PDZ domains recognize a specific C-terminal sequence motif present in their target proteins. TIP1 consists of a single PDZ domain encompassing residues 13-112 of the 124-amino acid protein. It recognizes proteins containing an X-S/T-X-I/L/V-COOH C-terminal recognition motif and a recently identified -S/T-X-L/V-D- internal motif.

Specific short-hairpin RNAs (shRNAs) against TIP1 inhibit tumor growth in vivo. However, RNA-mediated knockdown of TIP1 cannot be efficiently translated for cancer therapy. Therefore, the PDZ domain of TIP1 was targeted using antibodies for the treatment of NSCLC and GBM. The efficacy of the anti-PDZ antibodies on cancer cell proliferation and survival in vitro and in vivo was investigated. The following examples demonstrate for the first time that cancer-specific targeting and direct cytotoxicity can be achieved using antibodies against the PDZ domain of TIP1.

Example 1. Treatment with an Antibody Targeting TIP-1 and Knockout of TIP-1 Attenuates Cell Proliferation TIP1 is a 14 kDa protein that is important for tumor cell adhesion, migration and pulmonary metastasis. Elevated TIP1 levels have been reported to correlate with progression and poor prognosis of human cancers. TIP1 was targeted using an antibody that is specific to the PDZ binding groove (anti-PDZ Ab). Pharmacodynamics of the anti-PDZ antibody on GBM (U251 and D54) and NSCLC (A549 and H460) cell lines was determined. The U251, D54, A549 and H460 cells were treated with various concentration of anti-PDZ antibody ranging from 0.25 µg/ml to 5 µg/ml and cell proliferation at 96 h was measured. A dose-dependent reduction in proliferation in all cell lines with an optimum concentration of 1 µg/ml was observed. The time-dependent effect of this concentration (1 µg/ml) of anti-PDZ antibody on A549, D54, H460, and U251, at 24, 48, 72 and 96 h (FIG. 1A, FIG. 1B, FIG. 1C and FIG. 1D) was determined next. It was observed that treatment with anti-PDZ antibody reduced cell proliferation in a time-dependent manner in all cell lines (FIG. 1). Anti-PDZ antibody treatment reduced proliferation by 1.7-fold in A549 ($P<0.0001$), 2.9-fold in H460 ($P<0.0001$), 1.54-fold in U251 ($P<0.001$) and by 2-fold in D54 ($P<0.001$) when compared to isotype antibody treatment at 72 h. Furthermore, anti-PDZ antibody treatment reduced proliferation by 3.3-fold in A549 ($P<0.0001$), 11.2 fold in H460 ($P<0.0001$), 5-fold in U251 ($P<0.001$) and by 3.4-fold inD54 ($P<0.001$) when compared to isotype antibody treatment at 96 h (FIG. 1). These results indicate that the anti-PDZ antibody treatment attenuates cell proliferation in GBM and NSCLC cells in a time-dependent manner.

Figure 1E:
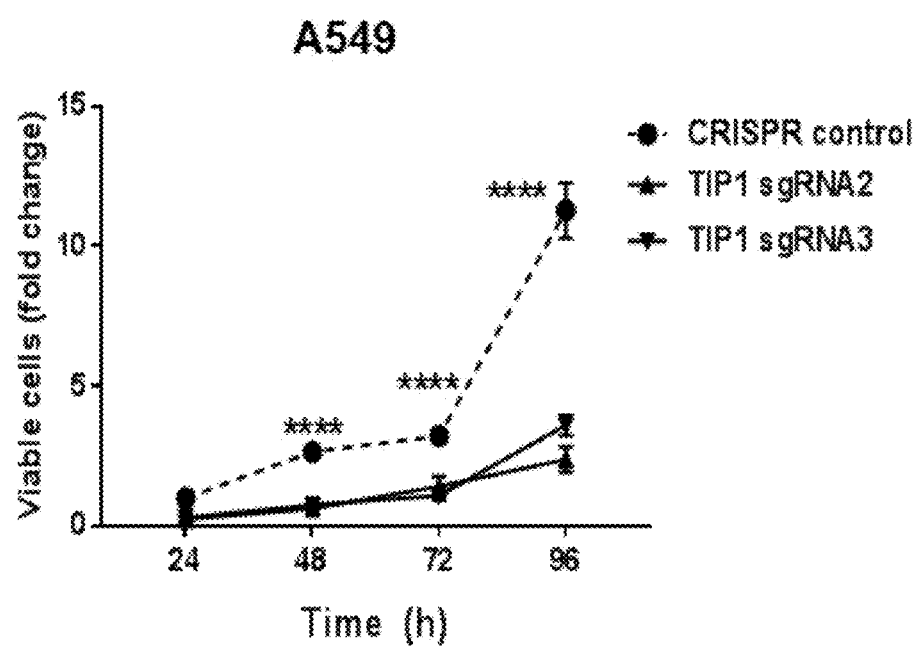
Figure 1F:
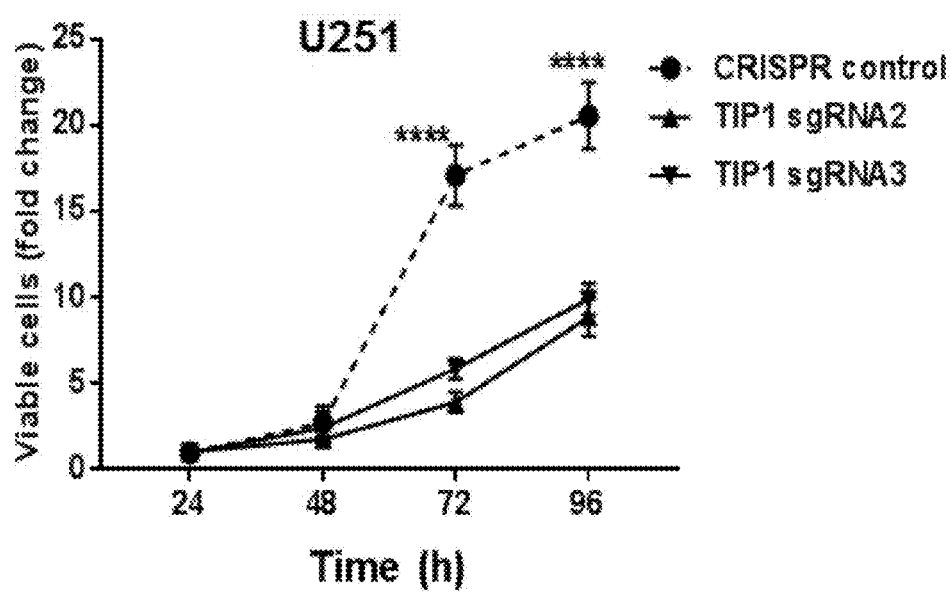

Next, CRISPR/Cas9 mediated knockout of TIP1 in A549 and U251 cells were generated. Protein analysis of A549 and U251 using western immunoblots showed knockout of TIP1 by both the sgRNAs. The proliferation of this TIP1-knockout (TIP1 KO) A549 and U251 cells at 24, 48, 72 and 96 h were examined. The A549 and U251 cells having TIP1 KO showed significantly reduced proliferation compared to cells transduced with CRISPR control vector in a time-dependent manner (FIG. 1E and FIG. 1F). The reduction in proliferation in TIP1 KO A549 and U251 was similar to A549 and U251 cells treated with the anti-PDZ/TIP1 antibody.

Example 2. PDZ Domain of TIP1 Plays a Role in Cell Proliferation

Figure 2A:
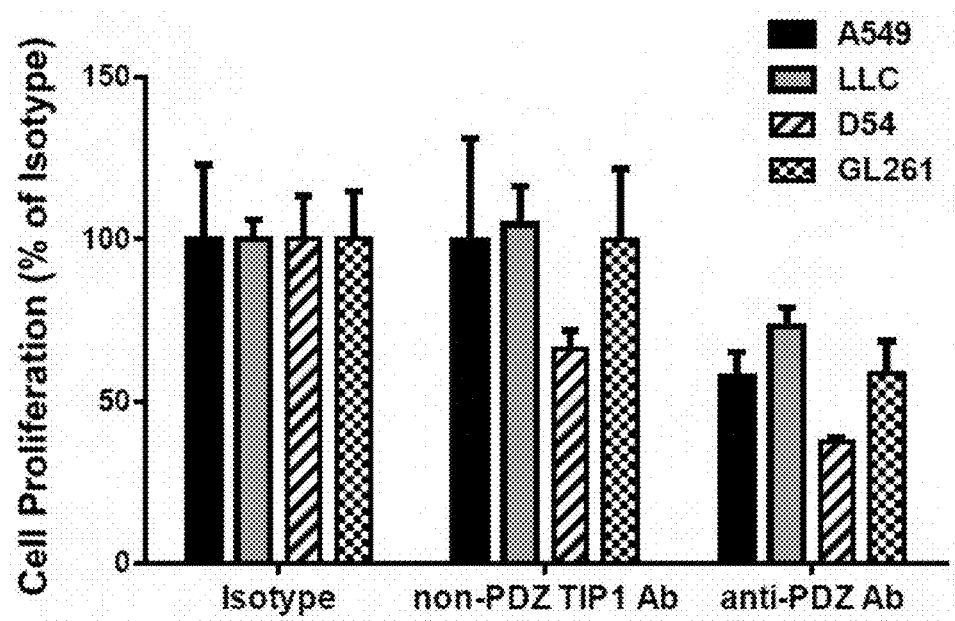
FIG. 2A, FIG. 2B, FIG. 2C and FIG. 2D depict graphs showing that the PDZ domain of TIP1 is important for cell proliferation.
Figure 2B:
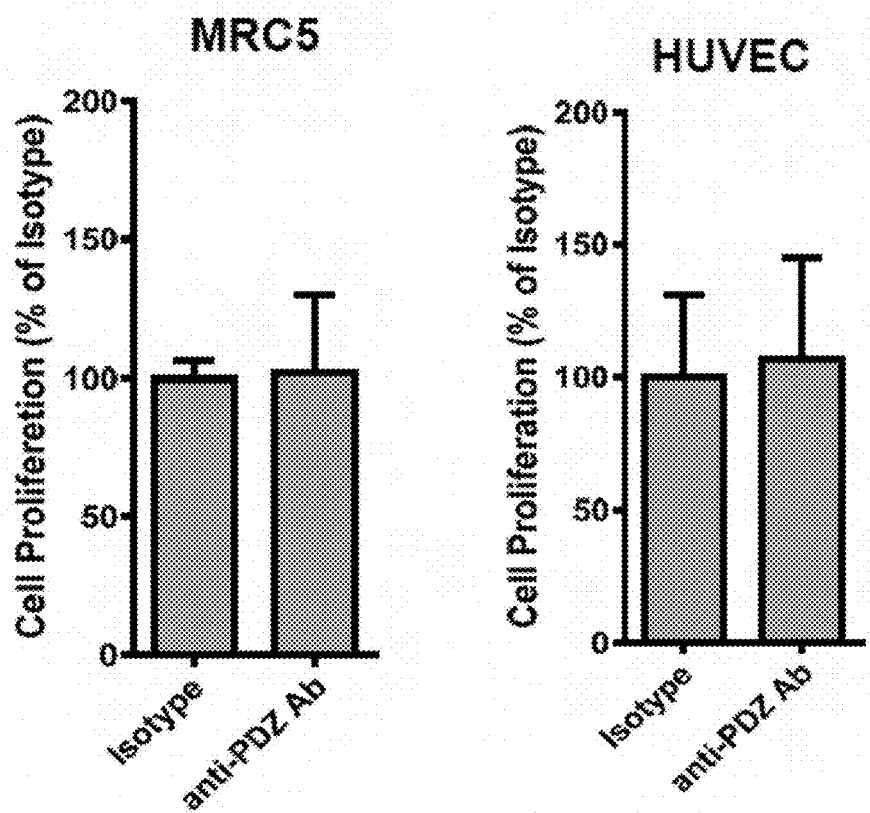

TIP1 functions in a wide variety of biological events through selective interaction with cellular proteins such as β-catenin, FAS, rhotekin, Kir 2.3 and Rho. These interactions are facilitated through the PDZ domain of TIP1. To determine if the PDZ domain played a vital role in cancer cell toxicity, the NSCLC and GBM cells were treated with 1 µg/ml anti-PDZ antibody, or 1 µg/ml anti-non PDZ antibody (2C6F3) or isotype control (FIG. 2A). Anti-PDZ antibody was able to significantly reduce proliferation of A549, LLC, D54 and GL261 cell lines when compared to the non-PDZ antibody or isotype control (FIG. 2A). The anti-PDZ antibody did not alter the cell viability of normal lung (MRC-5) and endothelial (HUVEC) cells (FIG. 2B). Due to its ability to reduce proliferation in cancer cells while sparing normal lung and endothelial cells, the anti-PDZ/TIP1 antibody was selected for all further experiments.

Figure 2C:
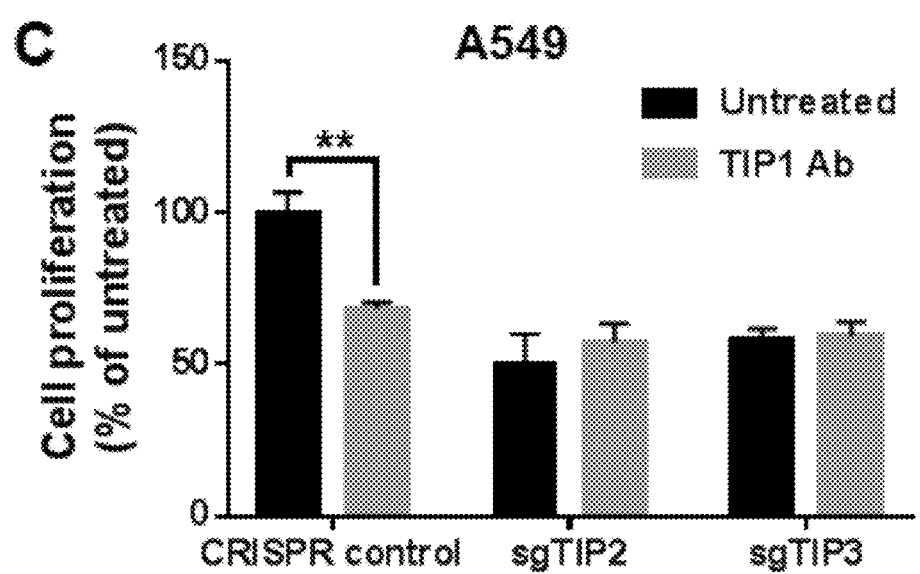
Figure 2D:
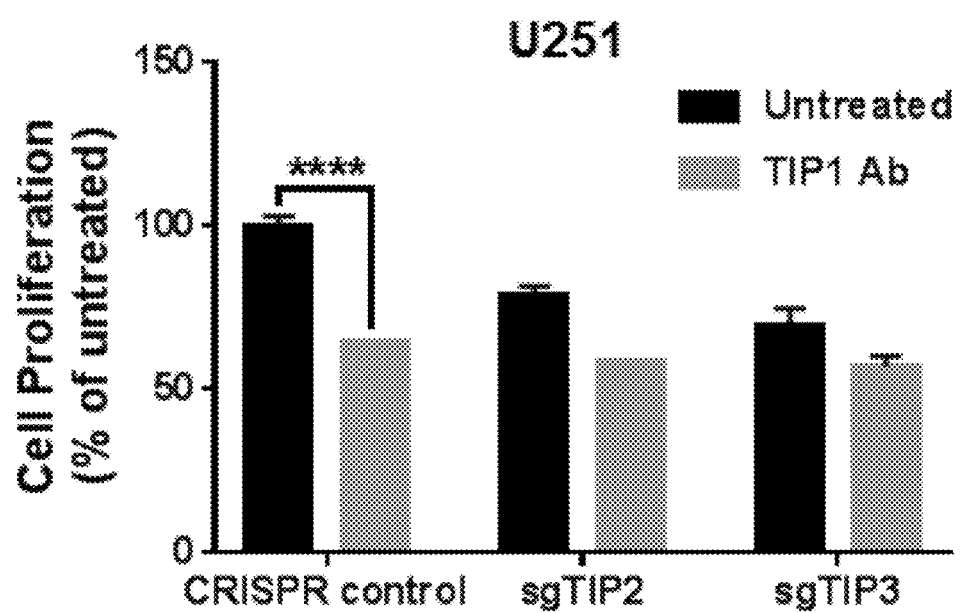

Cell proliferation in A549 and U251 cells lacking TIP1 by knockout with CRISPR was determined after they were treated with the anti-PDZ/TIP1 antibody for 96 h (FIG. 2C and FIG. 2 D). A549 and U251 cells with TIP1 (CRISPR control) showed a significant reduction ($p<0.001$) in proliferation after treatment with anti-PDZ/TIP1 antibody. Knockout of TIP1 using CRISPR/Cas9 led to a reduction of proliferation of A549 cells by 50% and U251 cells by 65% (FIG. 2C). The addition of the anti-PDZ/TIP1 antibody to TIP1 knockout A549 and U251 cells did not reduce proliferation further. When TIP1 was overexpressed in A549, and U251 cells, the effect of the anti-PDZ/TIP1 antibody was abrogated (data not shown). These results confirm the target specificity of the anti-PDZ/TIP1 antibody.

Example 3. Anti-PDZ Antibody Epitope Maps to the PDZ Binding Groove of TIP-1

Figure 3A:
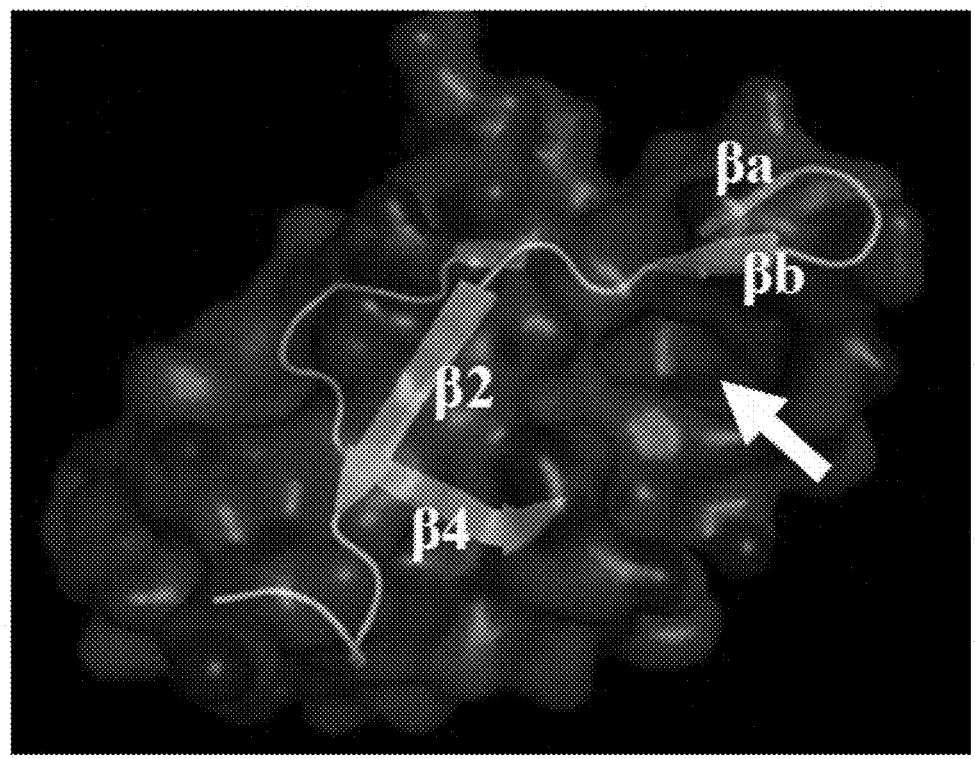
FIG. 3A, FIG. 3B, FIG. 3C and FIG. 3D depict images showing the structural depiction of the anti-PDZ and non-PDZ antibody epitopes. Surface representation of the TIP1 3D structure showing the anti-PDZ antibody epitopes as a (FIG. 3A) ribbon representation and (FIG. 3B) stick representation. The epitope of the non-PDZ antibody as a (FIG. 3C) ribbon and (FIG. 3D) stick representation. White arrows depict the PDZ binding pocket/groove involved in binding with interacting partners.
Figure 3B:
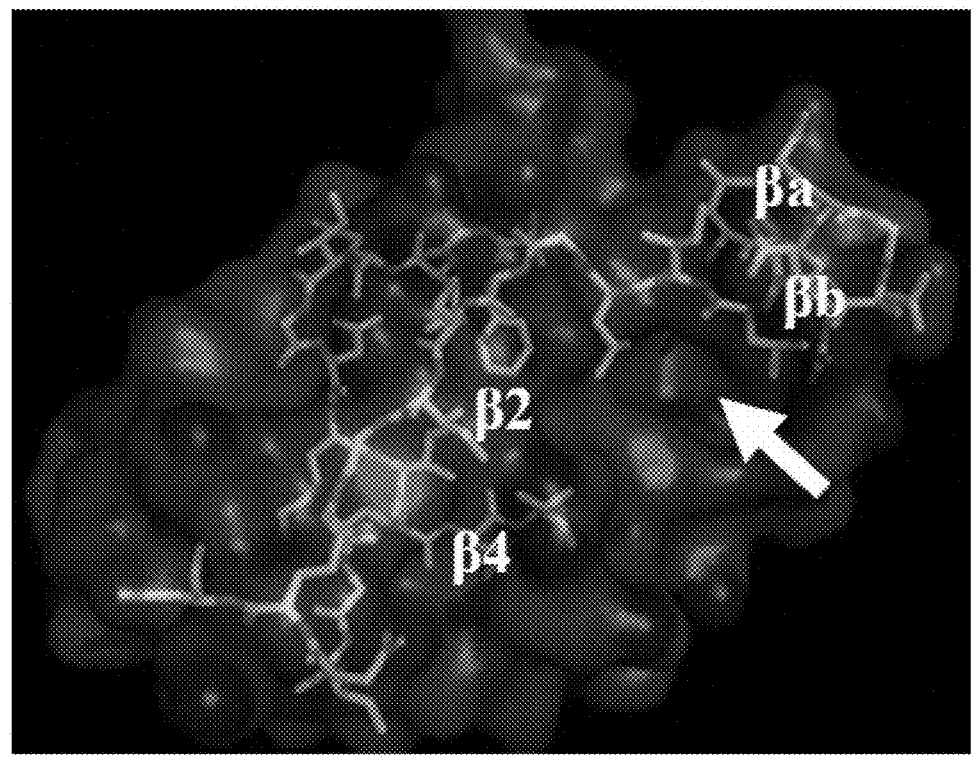
Figure 3C:
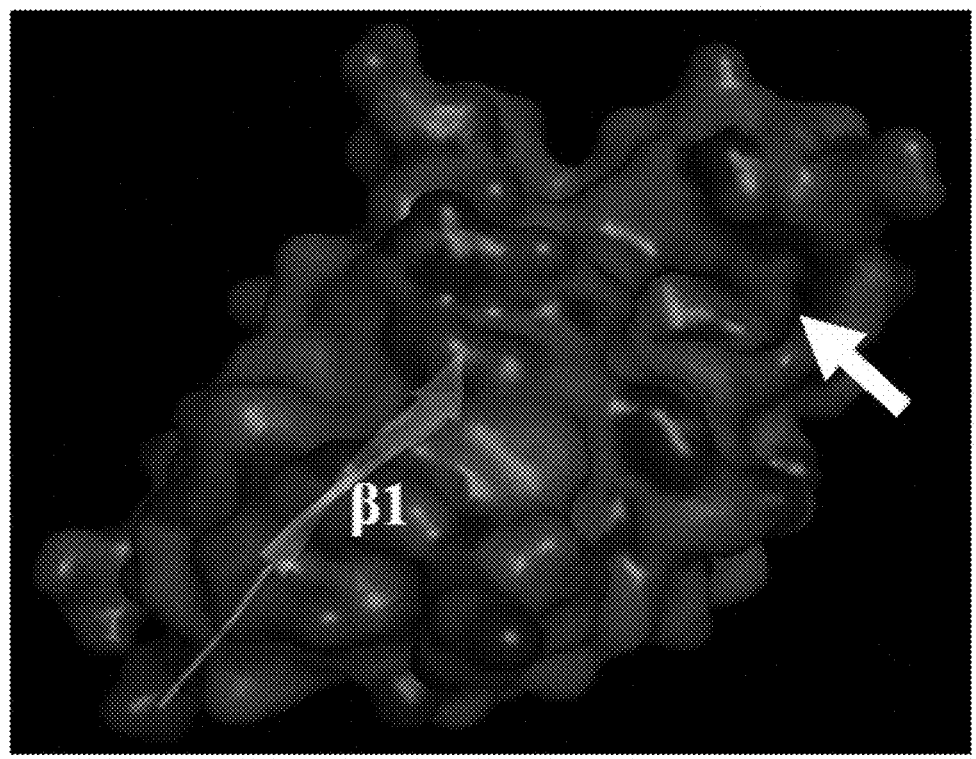
Figure 3D:
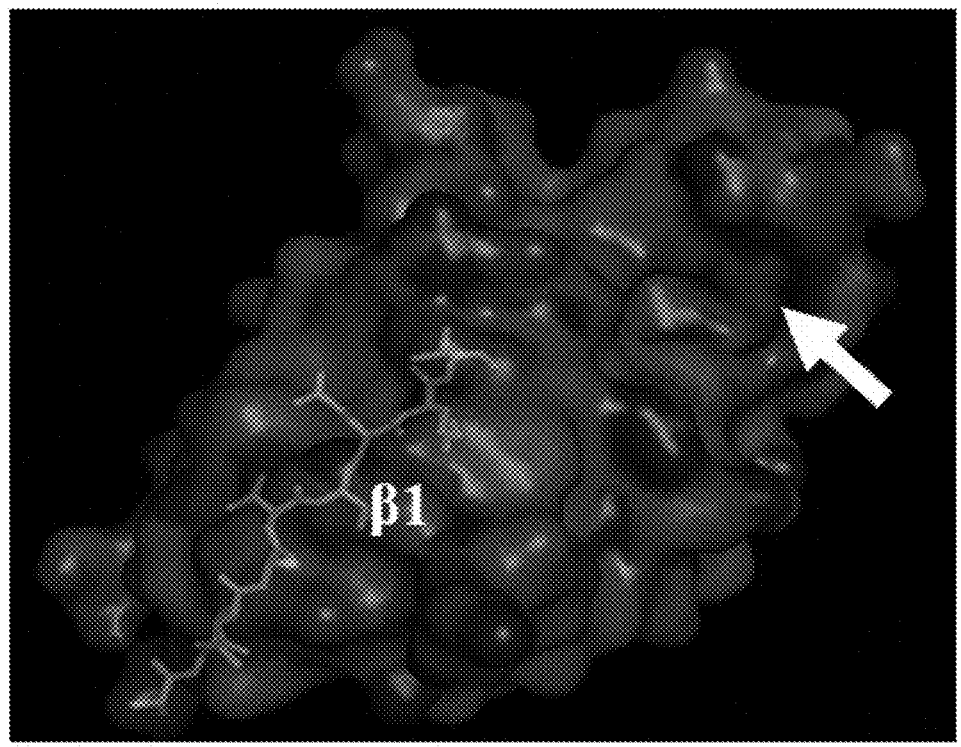

To determine if binding of the anti-PDZ antibody may be blocking the binding of TIP1 ligands, the PYMOL software was used to depict the 3D surface structure of the TIP1 protein and identify the positions of the anti-PDZ antibody and non-PDZ antibody epitopes. Interacting partners bind TIP1 in the PDZ binding groove lies between the β2-strand and α2-helix, as shown by the white arrows in FIG. 3A, FIG. 3B, FIG. 3C, and FIG. 3D. The PDZ binding groove in TIP1 contains a short β-hairpin composed of two anti-parallel β-strands (βa and βb) which are critical for the ligand binding and absent in other PDZ domains. The first epitopes of anti-PDZ antibody spanned the βa, βb, loop between βa and βb, ILGF motif, β2 and loop following β2 (FIG. 3A and FIG. 3B). The second epitope spanned the end of α1 containing the loop region followed by β4 (FIG. 3A and FIG. 3B) A similar representation of the non-PDZ antibody (the antibody that did not induce any cytotoxicity), showed that its epitope spanned the β1 sheet which has not been reported to be involved in any interactions (FIG. 3C and FIG. 3D).

Figure 4A:
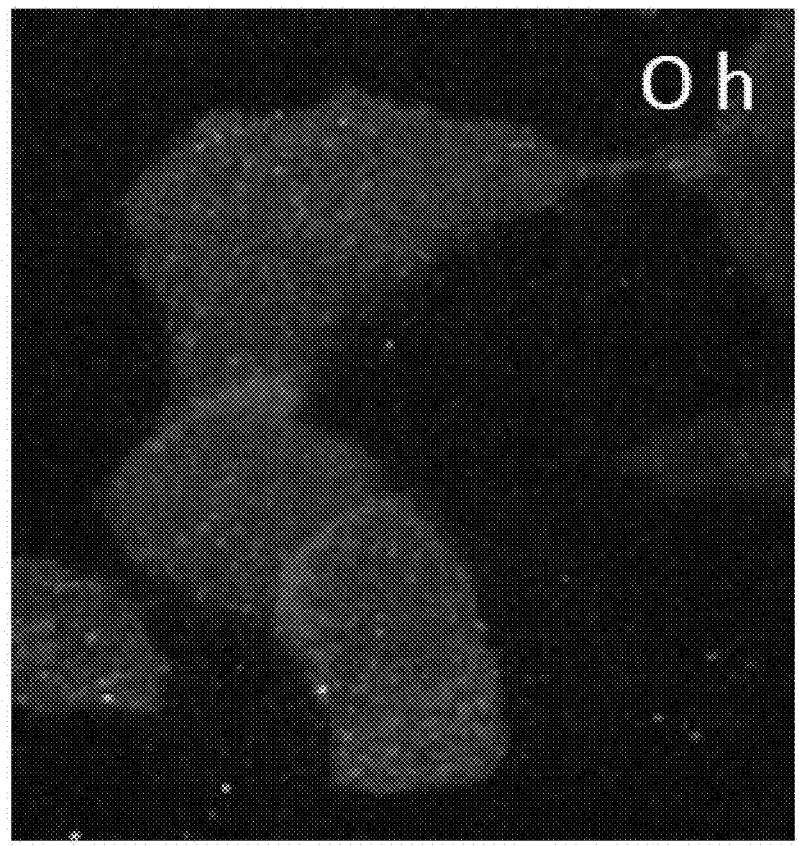
FIG. 4A, FIG. 4B, FIG. 4C, FIG. 4D, FIG. 4E, FIG. 4F, FIG. 4G and FIG. 4H depict images and graphs showing that anti-PDZ antibody treatment induces apoptosis following internalization in NSCLC and GBM cell lines.
Figure 4B:
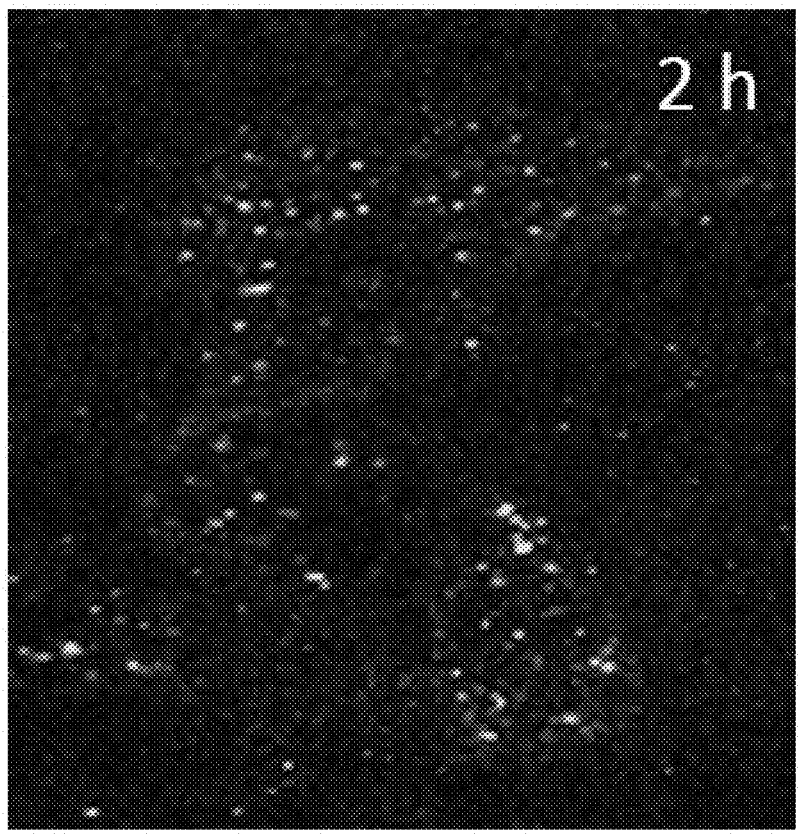
Figure 4C:
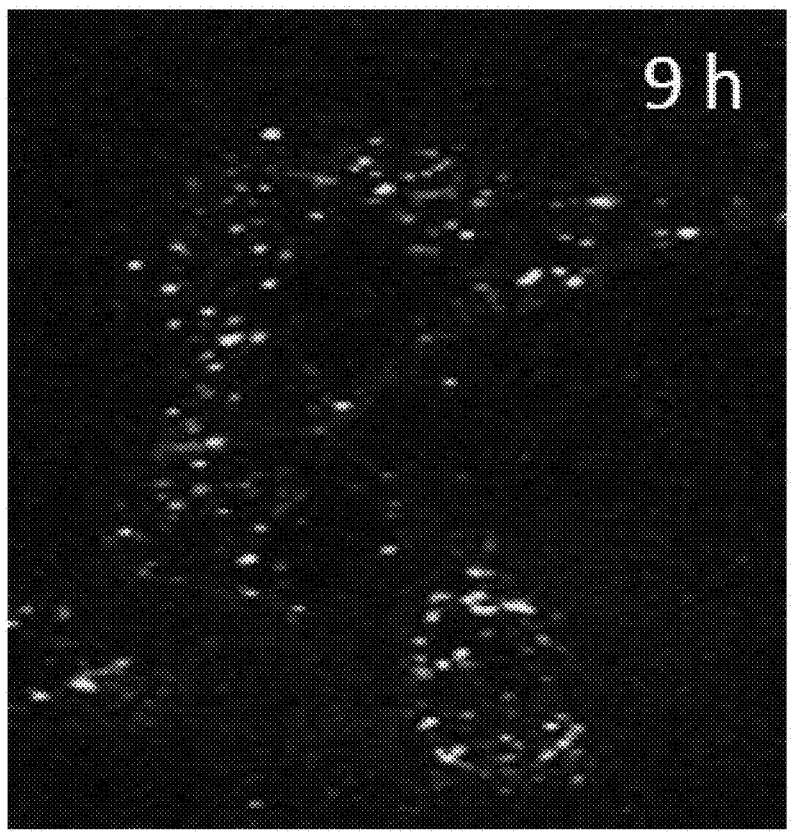
Figure 4D:
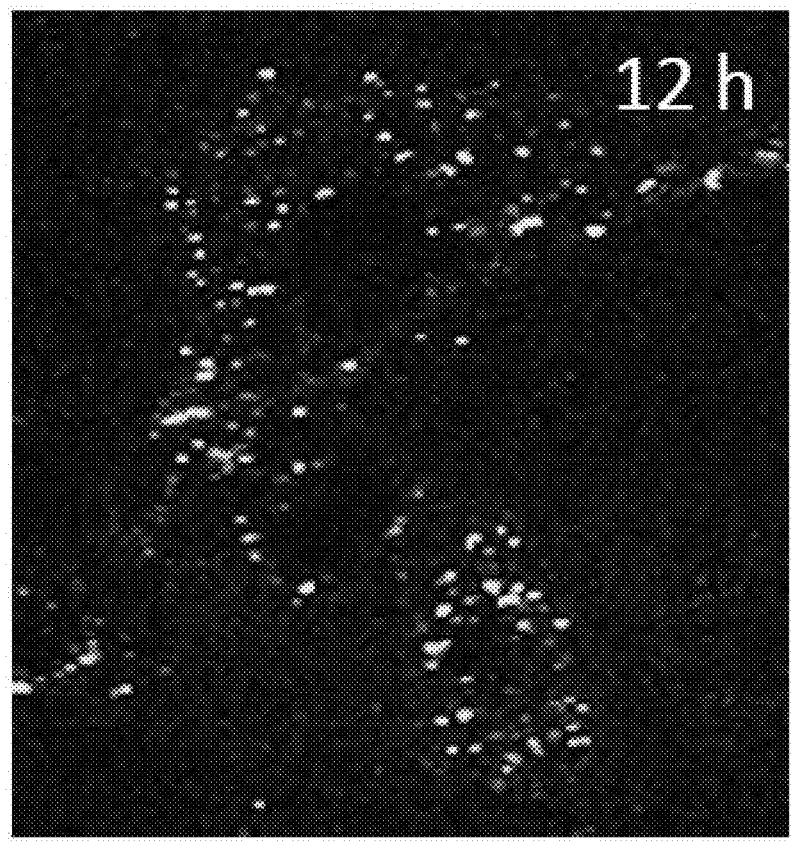
Figure 4E:
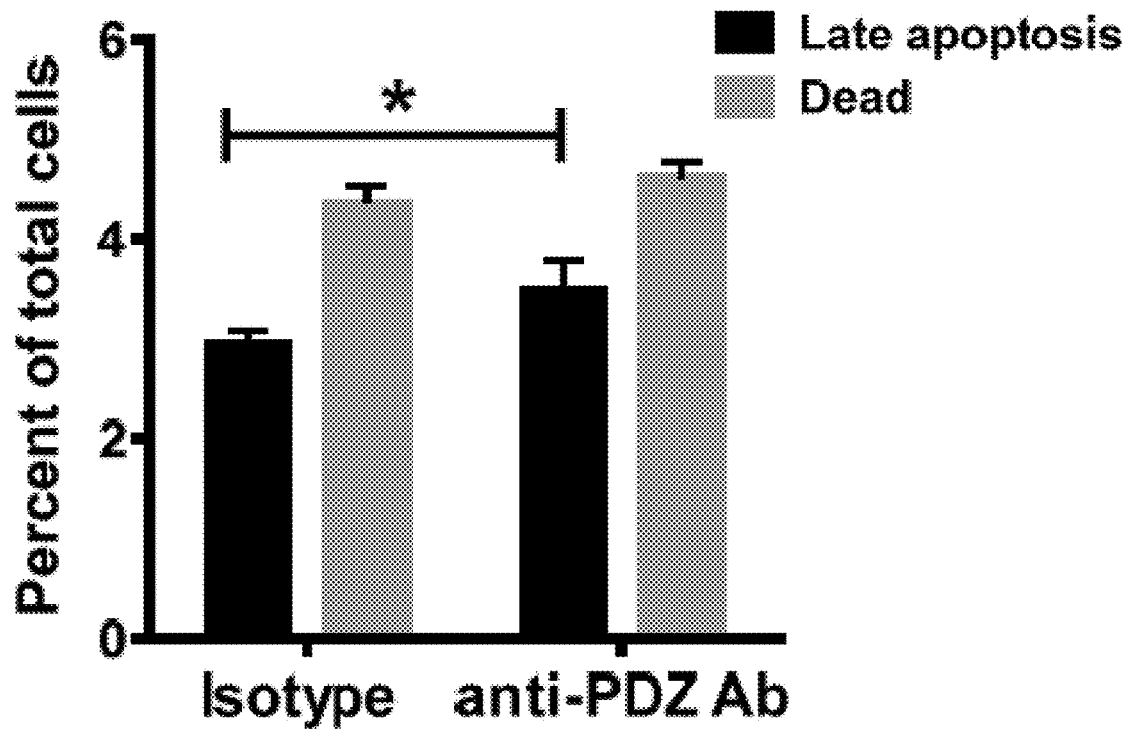
Figure 4F:
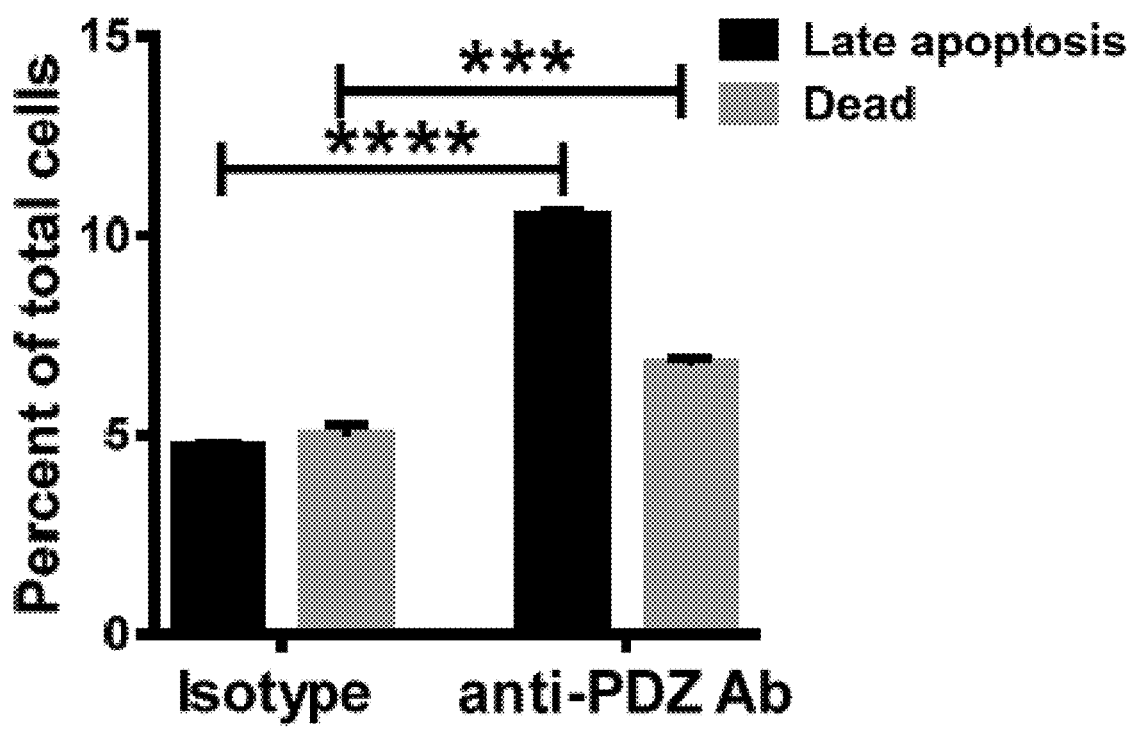
Figure 4G:
Figure 4H:
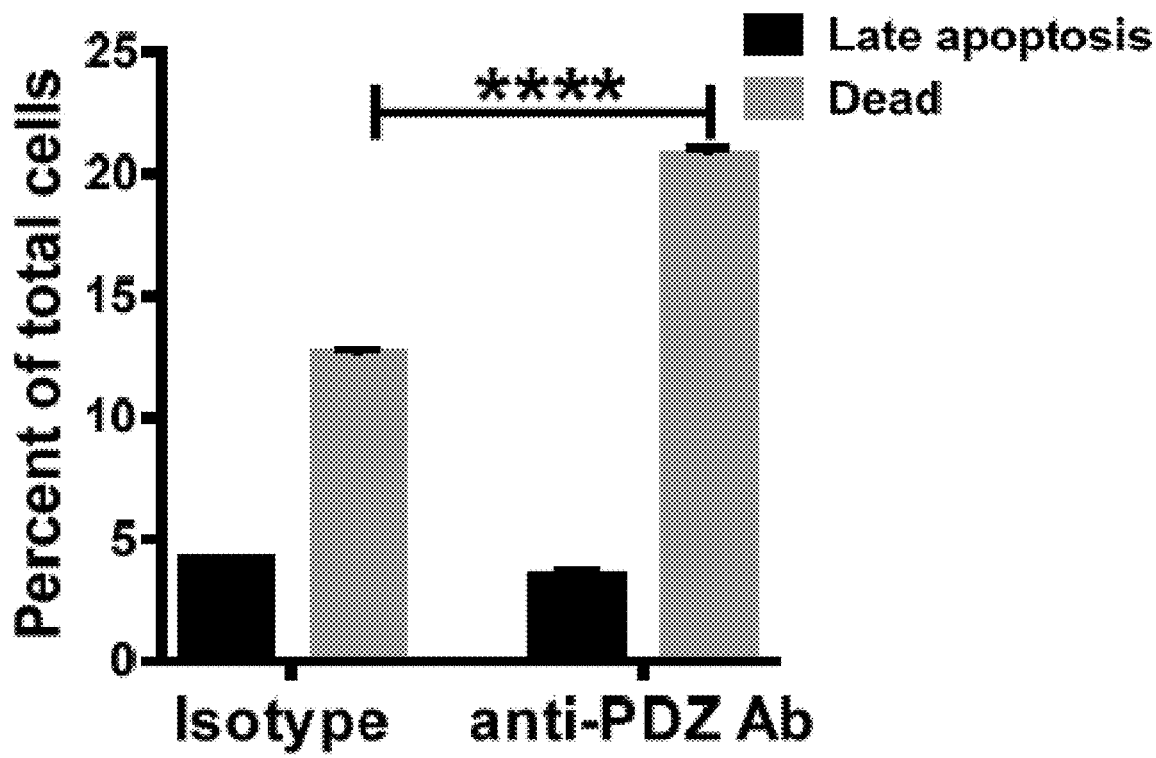

Example 4. Anti-PDZ Antibody is Internalized and Induces Cell Death by Apoptosis in Cancer Cells Live cell imaging to track anti-PDZ antibody after treatment of A549 cells was performed. The A549 cells were labeled with a lipophilic dye (Cell Mask Orange) to stain the cell membranes red. The anti-PDZ antibody was labeled with Alexa-Flour 488 fluorescent dye. FIG. 4A, FIG. 4B, FIG. 4C, and FIG. 4D show representative images at 0, 2, 9 and 12 h respectively, after the addition of Alexa-Flour 488 conjugated anti-PDZ antibody. The antibody accumulation within the cells was seen as early as 2 h and saturated at 9-12 h (FIG. 4B). The overlaid images show the internalization of the antibody (Yellow). The intracellular accumulation of the antibody was still saturated at 24 h.

It was evaluated if anti-PDZ antibody treatment would induce cell death by apoptosis using annexin-V/PI assay. NSCLC (A549, H460) and GBM (U251 and D54) cells were treated with 1 µg/ml anti-PDZ antibody for 96 h. The cells were then stained with Annexin V and PI and analyzed using a flow cytometer. Percentages of cells undergoing late apoptosis (Annexin-V positive, PI positive) and necrosis (PI positive) are shown in FIG. 4B. It was found that anti-PDZ antibody was able to significantly induce apoptosis in A549 (3.5%, $P<0.05$), D54 (10.5%, $P<0.0001$), H460 (37.3%, $P<0.0001$), and U251 (3.5%) (FIG. 4E, FIG. 4F, FIG. 4G, and FIG. 4H). The percentage of cells undergoing necrosis following anti-PDZ antibody treatment was A549 (4.6%), H460 (38.3%, $P<0.0001$), U251 (20.7%, $P<0.0001$) and D54 (6.7%, $P<0.0001$).

Cell cycle analysis was performed to determine the effect of the anti-PDZ antibody on A549, H460, D54 and U251 cells. All the cells tested showed an increase in the sub-G1 population confirming the induction of apoptosis after antibody treatment. However, significant differences were not observed in the percentage of cells in G1, S and G2 phase of the cell cycle after treatment with anti-PDZ/TIP1antibody compared to the isotype control.

Example 5. Antibody Targeting TIP-1 Suppresses AKT and mTOR Signaling

Figure 5A:
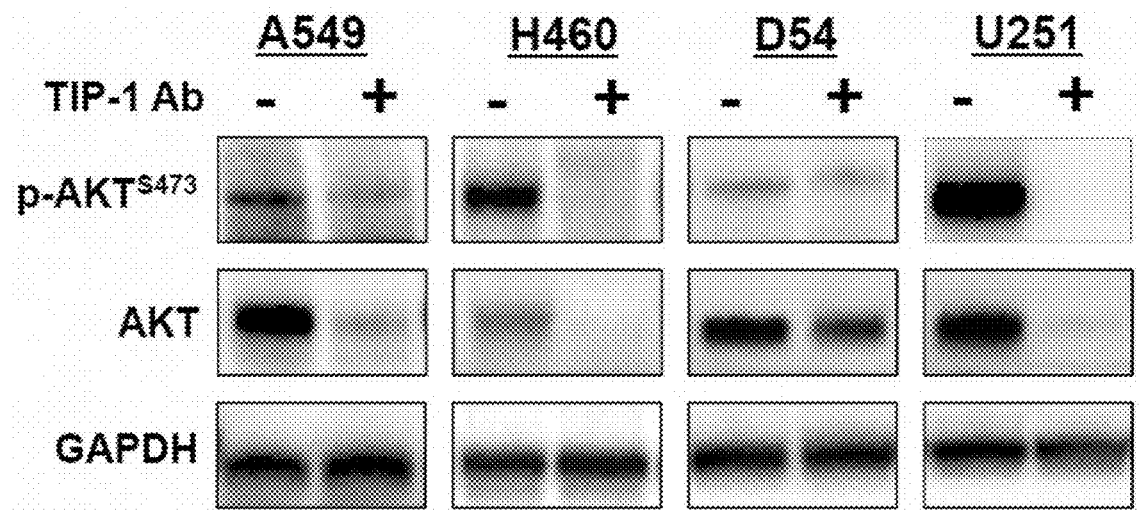
FIG. 5A and FIG. 5B depict antibodies against PDZ domain of TIP-1 suppress AKT/mTOR signaling in NSCLC and GBM cell lines. Immunoblot analysis of survival pathways. Lung cancer (A549 and H460) and glioblastoma (D54 and U251) cells were treated with 1 µg/ml of anti-PDZ antibody for 96 h.
Figure 5B:
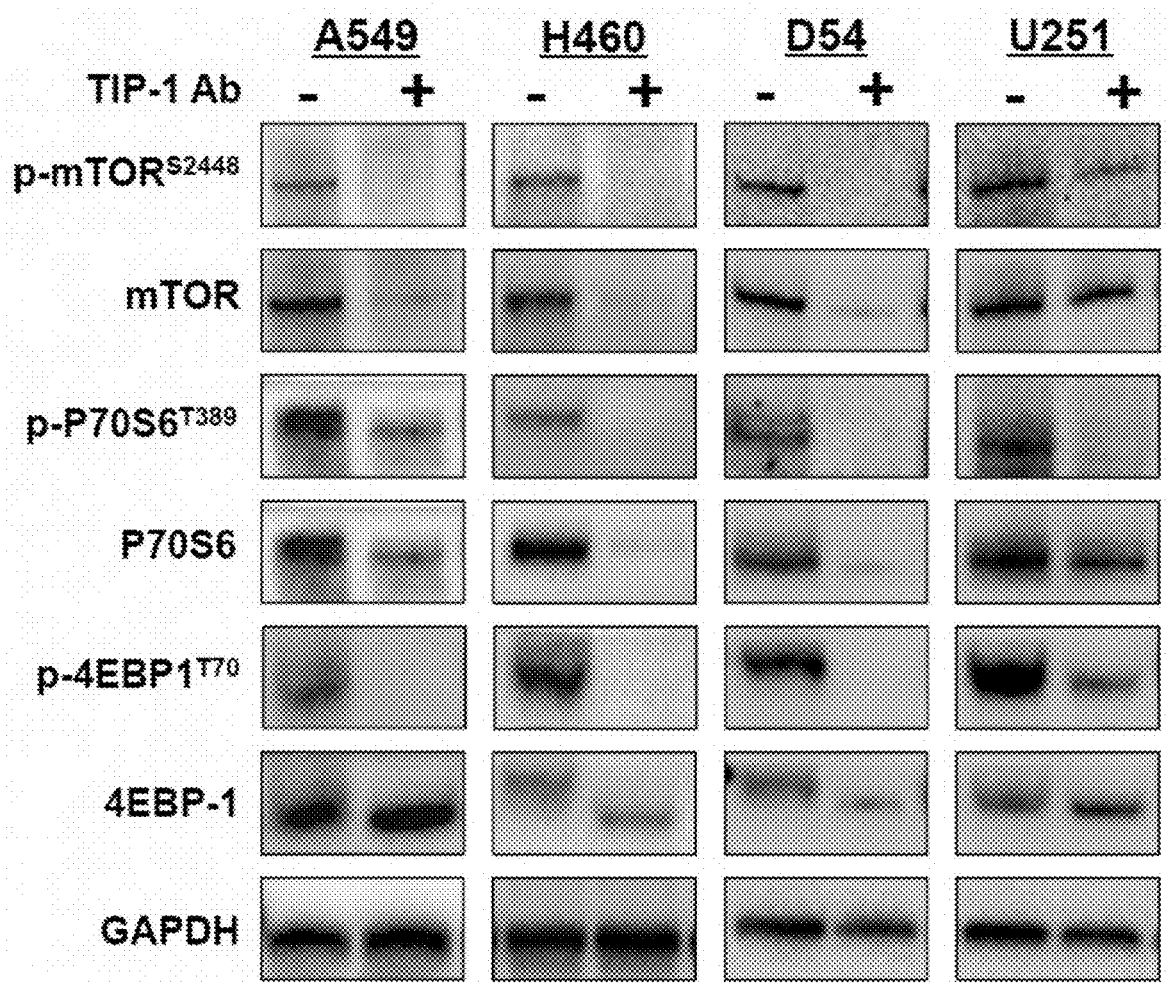

The PI3K/AKT pathway is a mediator of pro-survival signaling. As a major regulator of cell proliferation and survival, AKT has been implicated in modulating cell survival after insults with therapeutic agents. To identify the mechanisms by which anti-PDZ antibody is modulating cell survival in GBM and NSCLC, AKT and mTOR signaling that regulates cell proliferation were evaluated. GBM (U251 and D54) and NSCLC (A549 and H460) cells were treated with 1 µg/ml anti-PDZ antibody for 96 h, and soluble proteins were immunoblotted with antibodies against the AKT and mTOR signaling pathways. The A549, H460, U251 and D54 cells treated with anti-PDZ antibody showed reduced abundance of phospho-AKT and total AKT (FIG. 5A). Furthermore, attenuation of phosphorylated and total levels of mTOR, p70S6 kinase, and 4EBP1 were observed (FIG. 5B). Since p70S6 kinase and 4EBP1 are downstream targets of mTOR, these results indicate that AKT/mTOR and some of its downstream effectors are inhibited by targeting TIP1.

Example 6. Antibody Targeting the PDZ Domain of TIP-1 Enhances the Efficacy of Radiation and Delays Tumor Growth in Mouse Xenograft Models Radiation in combination with chemotherapy is the standard of care for GB and NSCLC. The efficacy of combining the anti-PDZ/TIP1 antibody with radiation on GB and NSCLC using proliferation and colony formation assays was evaluated. It was found that anti-PDZ antibody alone was able to significantly reduce proliferation in A549 cells (53%, P=0.0002), H460 cells (7.3%, P<0.0001), U251 cells (65%, P=0.0001) and D54 cells (41%) compared to isotype (FIG. 6K, FIG. 6L, FIG. 6M and FIG. 6N). Similarly, radiation alone reduced proliferation in A549 cells (40%), H460 cells (36%), U251 cells (73%) and D54 cells (38%) compared to isotype (FIG. 6K, FIG. 6L, FIG. 6M and FIG. 6N). Combining anti-PDZ antibody with radiation led to reduced proliferation in A549 (25%, P<0.05), H460 (18%, P<0.05), U251 (42%, P<0.05) and D54 cells (30%) when compared to either anti-PDZ antibody, or irradiation or isotype alone (FIG. 6K, FIG. 6L, FIG. 6M and FIG. 6N).

Colony formation assays with GBM (U251 and D54) and NSCLC (A549 and H460) cell lines were performed. A549, H460, U251 and D54 cells were treated with 1 µg/ml anti-PDZ antibody and irradiated with 3Gy and incubated for 96 h. The colony formation assays showed that anti-PDZ antibody attenuated the surviving fraction in A549 (0.25, P<0.0001), D54 (0.57, P<0.05), H460 (0, P<0.0001), and U251 (0, P<0.001). Radiation alone also reduced the surviving fraction in A549 (0.8), H460 (0.2), U251 (0.25) and D54 (0.11). The combination of radiation with anti-PDZ antibody showed a reduced surviving fraction in A549 (0.15, P<0.0001), H460 (0, P<0.0001), U251 (0, P<0.0001) and D54 (0.03) when compared to either antibody, radiation alone or isotype alone (FIG. 6A, FIG. 6B, FIG. 6C, FIG. 6D). These results demonstrate that the combination of the anti-PDZ antibody with radiation led to enhanced cell kill when compared to treatment with either anti-PDZ antibody or radiation alone in both GBM and NSCLC cells.

Figure 6A:
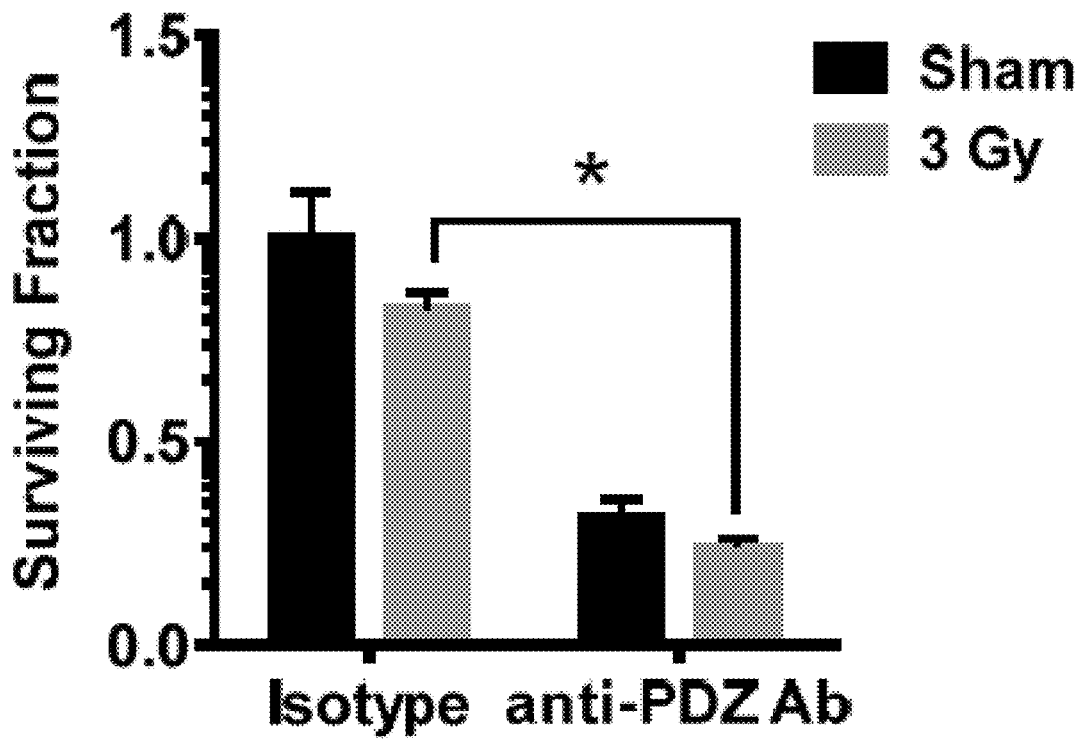
FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M and FIG. 6N depict graphs showing that the anti-PDZ antibody enhances the efficacy of XRT and delays growth of A549 and U251 tumor xenografts implanted into hind limbs of athymic nude mice.
Figure 6B:
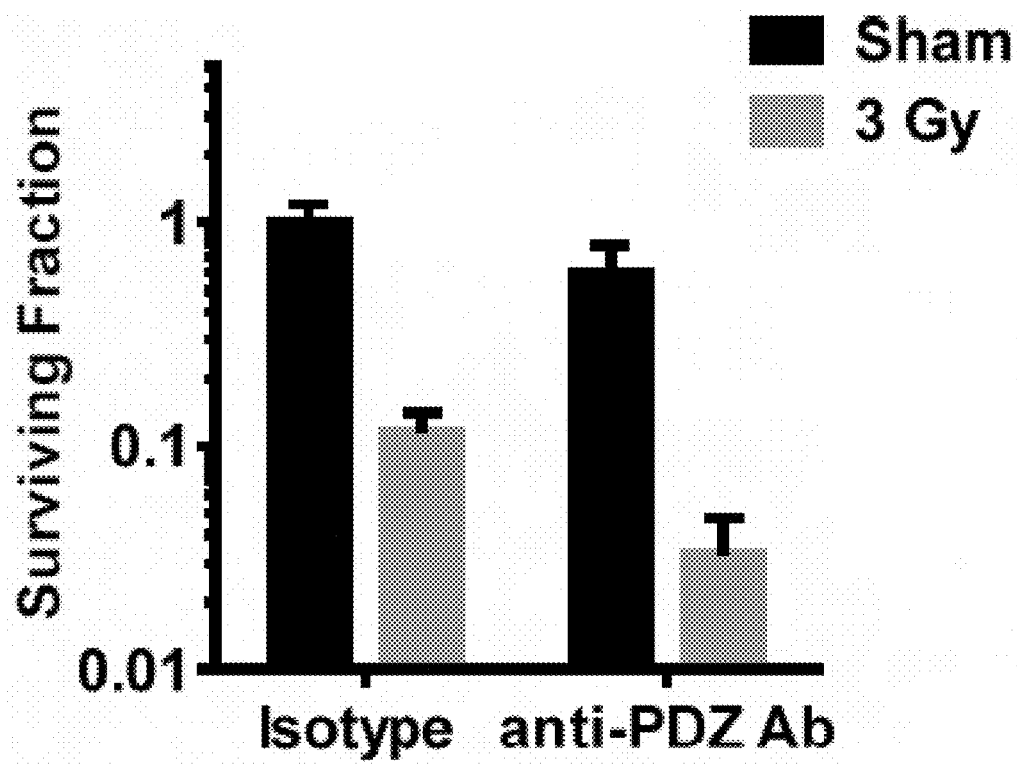
Figure 6C:
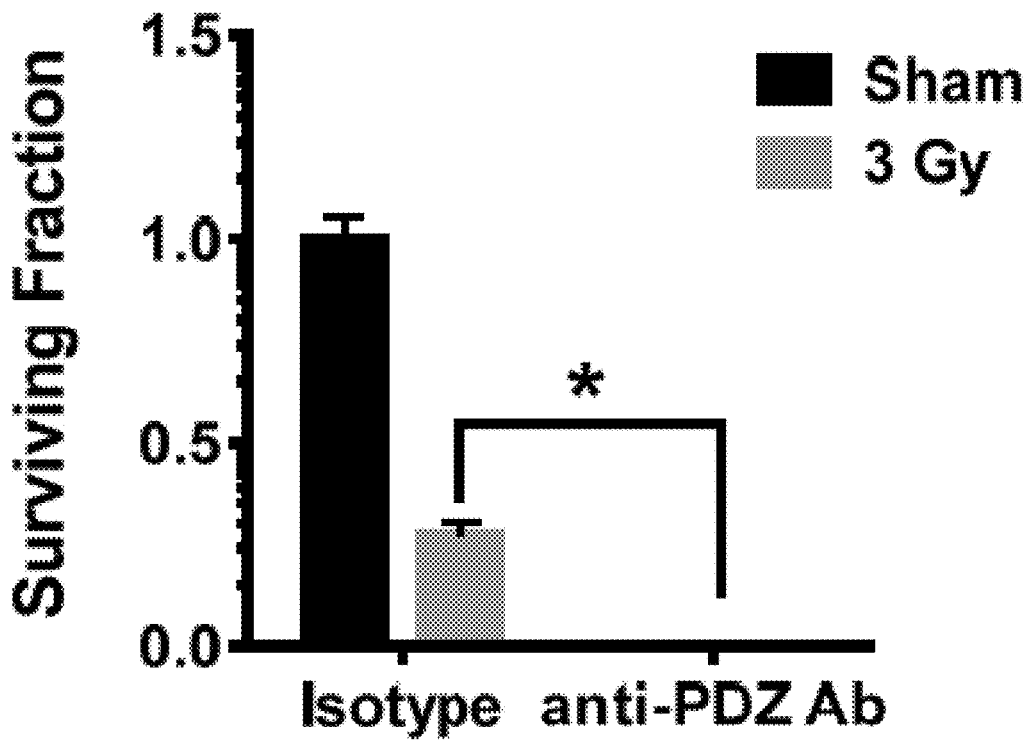
Figure 6D:
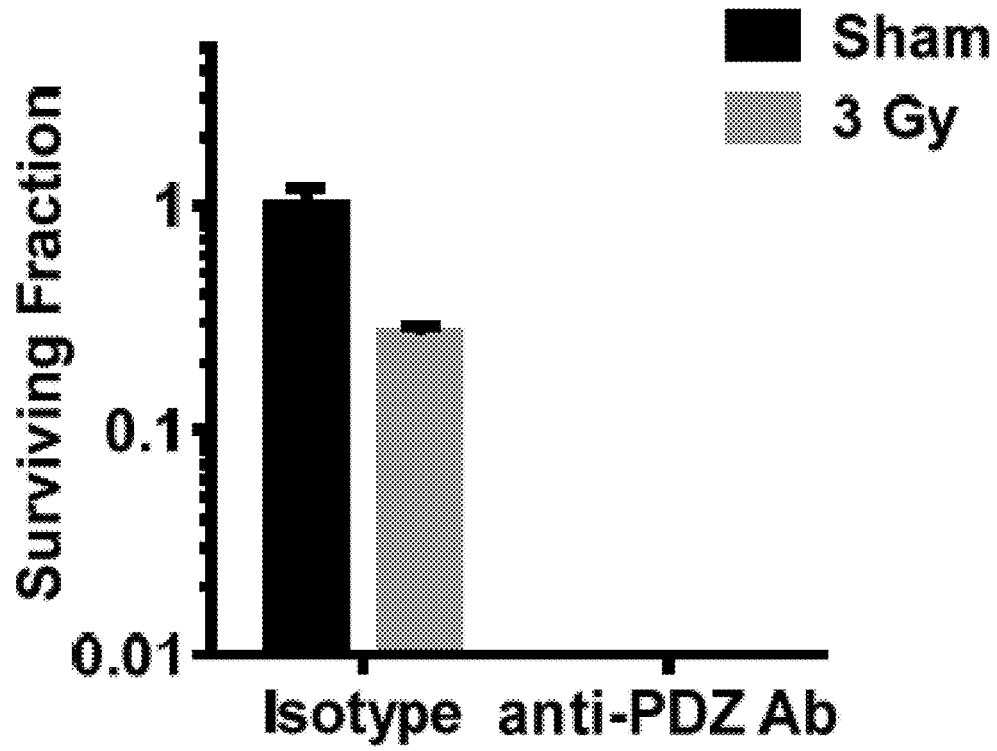
Figure 6E:
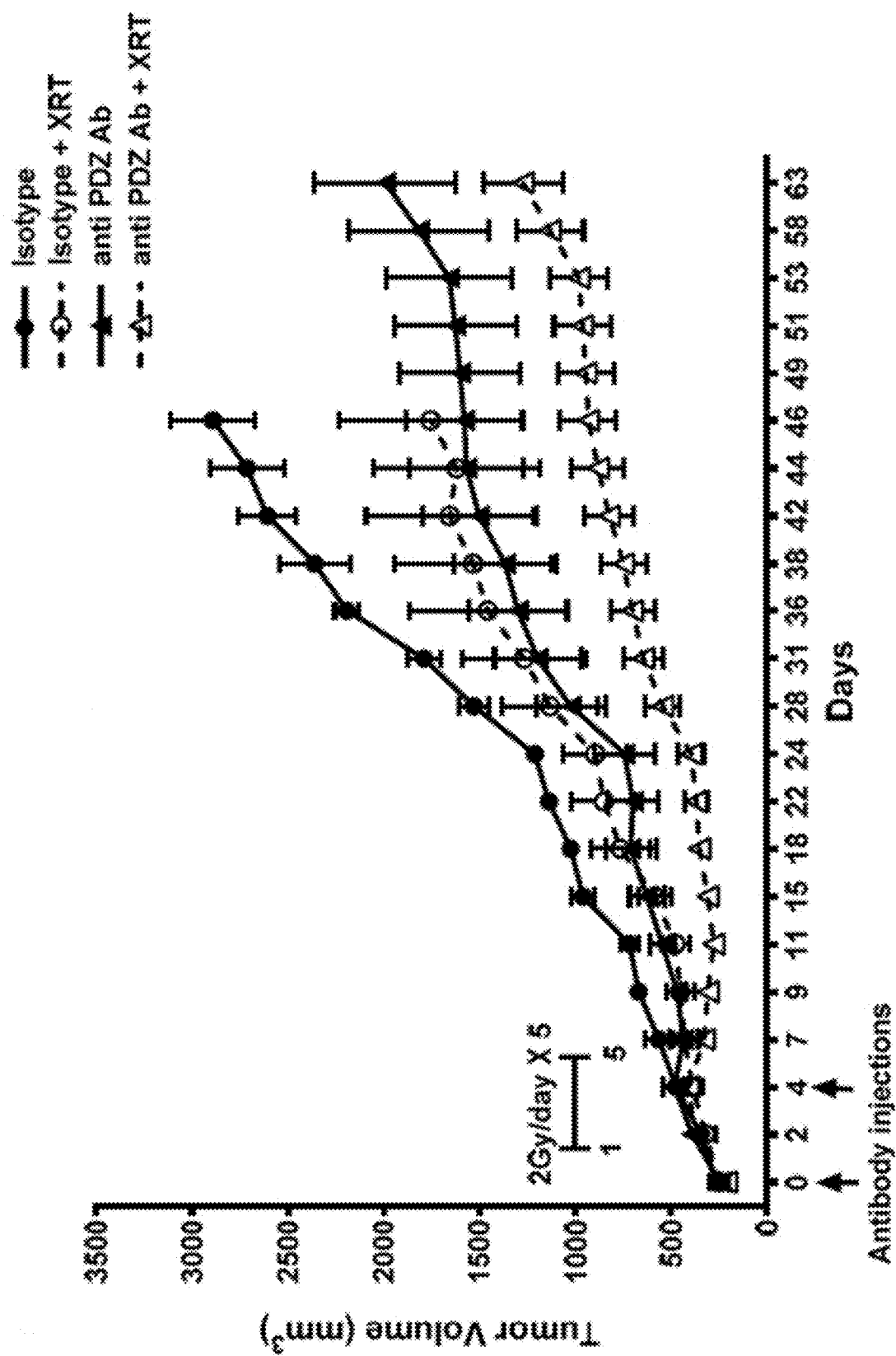

The effect of treatment with the anti-PDZ antibody on the growth of heterotopic tumors of NSCLC (A549) and glioblastoma (U251) was investigated. Tumor-bearing mice were treated with 300 µg of anti-PDZ or isotype antibody with or without irradiation (5 fractions of 2 Gy). The efficacy of the PDZ antibody treatment was determined by measuring the tumor growth on day 45 (A549) and day 35 (U251) shown in FIG. 6E, FIG. 6F, FIG. 6G, FIG. 6H. The mice treated with anti-PDZ antibody had an average tumor volume of 1590 mm3 which was significantly smaller than mice treated with the isotype control antibody which had an average tumor volume of 2890 mm3 (P<0.0001) on day 45. The mice treated with a combination of anti-PDZ and radiation resulted in an average tumor volume of 932 mm3 which was significantly smaller (P=0.0040) than the mice treated with a combination of isotype control antibody and radiation (1753 mm3) or PDZ antibody alone (1590 mm3). The mice treated with either anti-TIP-1 antibody, anti-TIP-1 antibody in combination with radiation or isotype control antibody in combination with radiation did not attain an average tumor volume of 2500 mm3 even at day 63 (FIG. 6E). The combination treatment of anti-PDZ antibody with radiation had the greatest effect in delaying tumor growth, followed by anti-PDZ antibody alone.

Figure 6F:
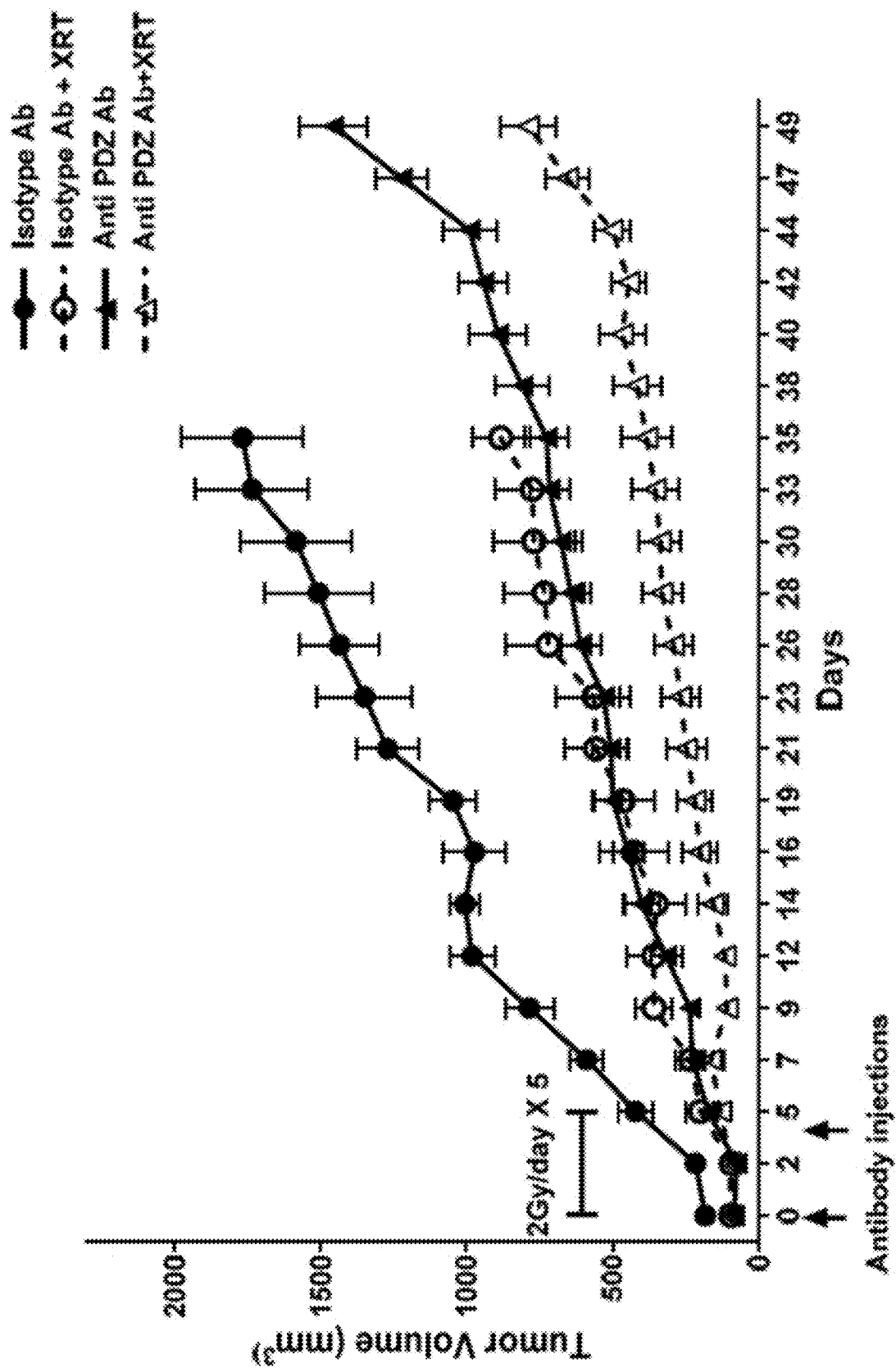
Figure 6G:
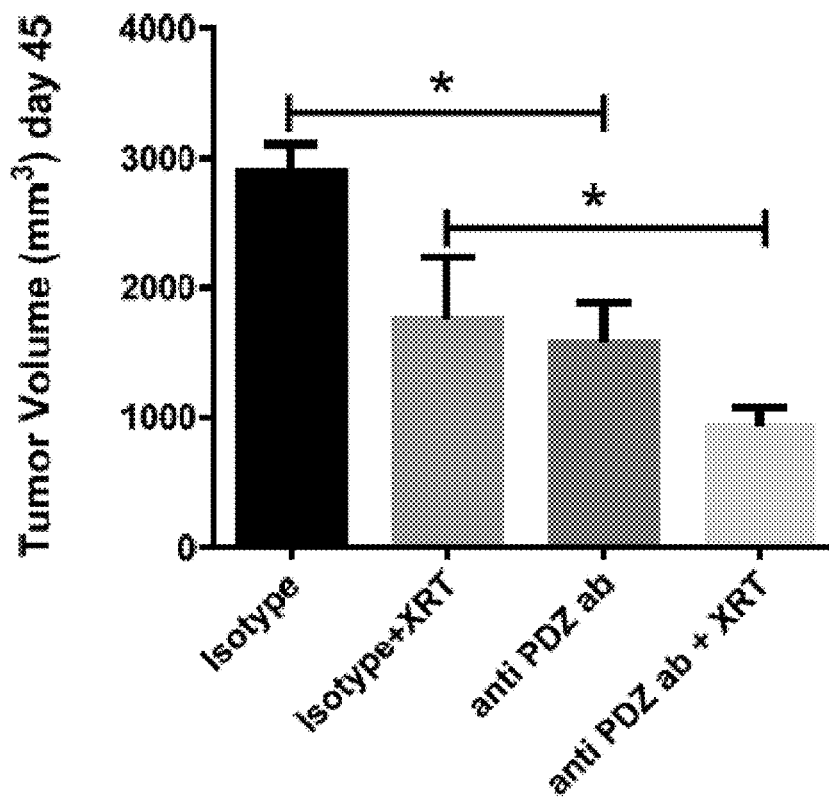
Figure 6H:
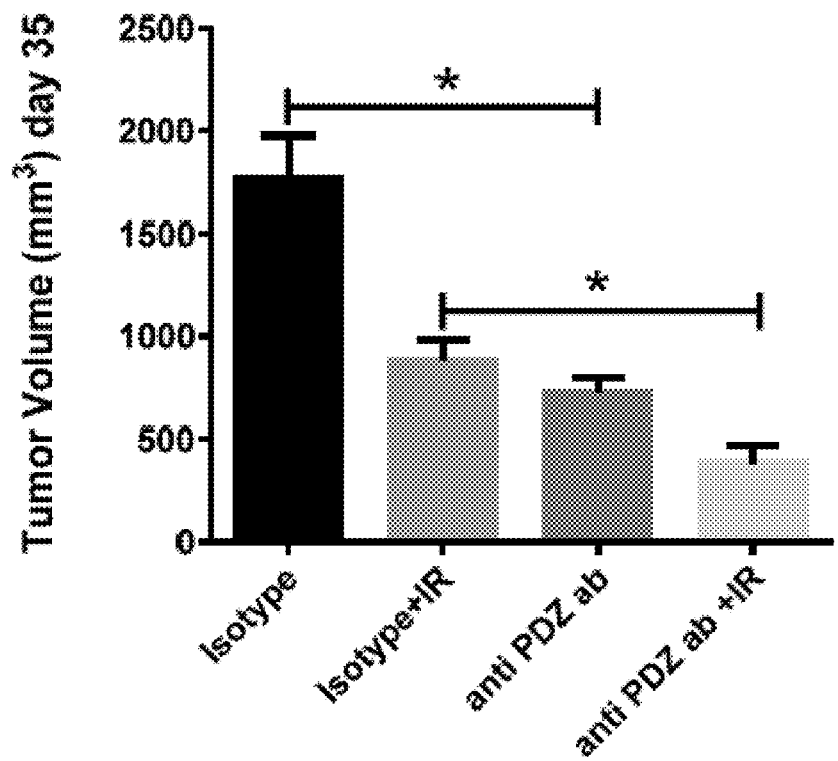

The mice bearing U251 tumor treated with anti-PDZ antibody had an average tumor volume of 725 mm3 (P<0.0001) which was significantly smaller when compared to mice treated with isotype control antibody which had an average tumor volume of 1768 mm3 on day 35. The mice treated with a combination of anti-PDZ and radiation had an average tumor volume of 381 mm3 which was significantly less than the tumors of the mice treated with isotype control antibody in combination with radiation (882 mm3; P<0.0001). The tumors of the mice treated with either anti-PDZ antibody, anti-PDlZ antibody in combination with radiation or isotype control antibody in combination with radiation did not reach a volume of 2000 mm3 even after 50 days (FIG. 6F).

Similar to the results obtained with the NSCLC tumor model, the combination of the anti-PDZ antibody with radiation had the greatest effect on delaying GBM tumor growth, followed by the anti-PDZ antibody alone.

Figure 6I:
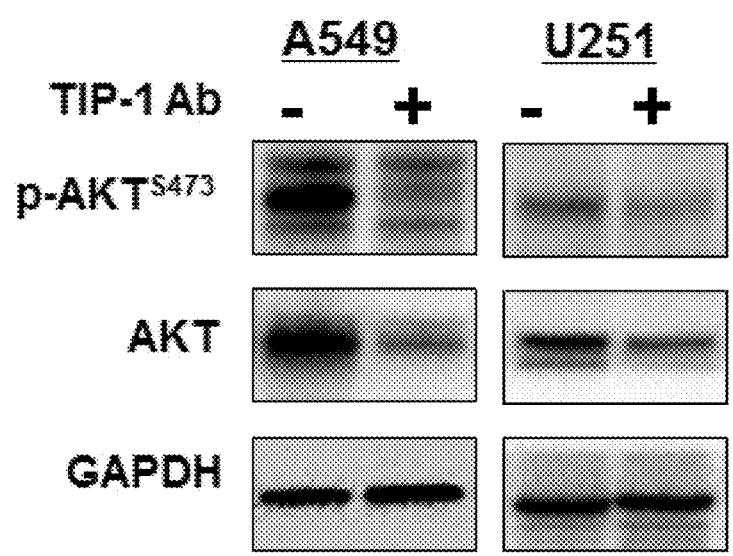
Figure 6J:
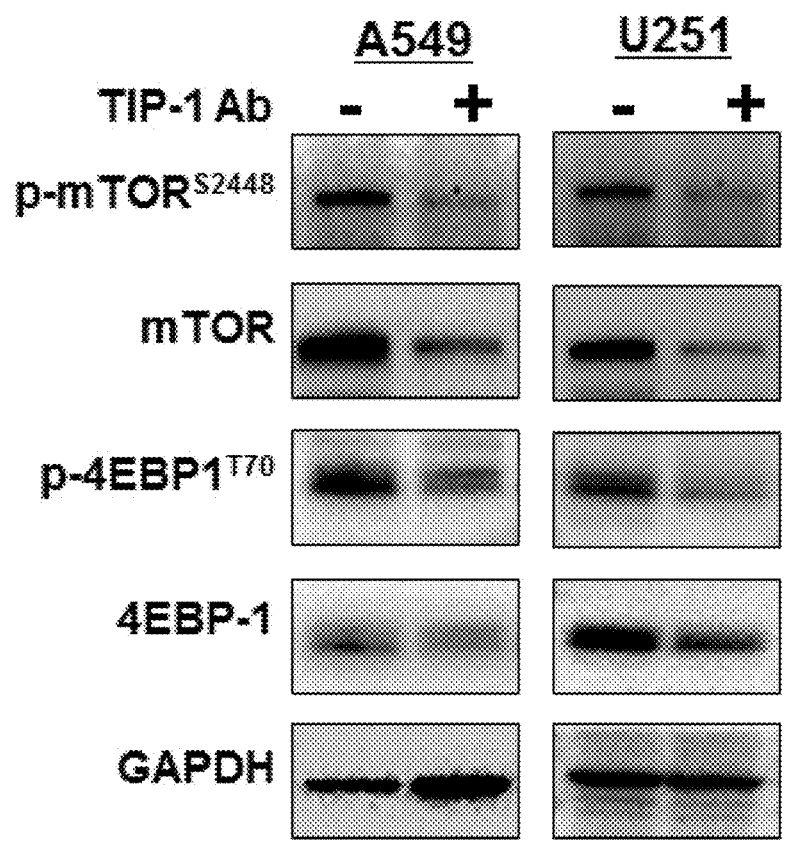
Figure 6K:
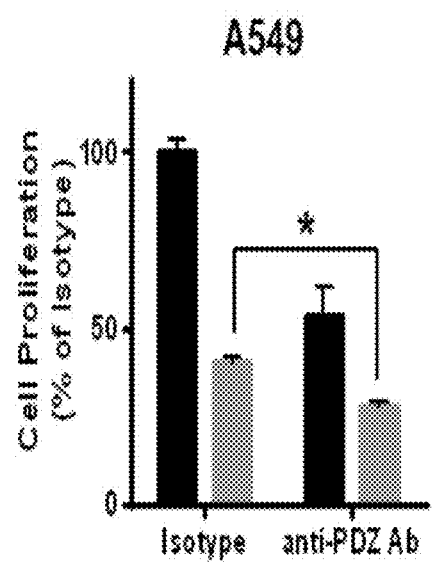
Figure 6L:
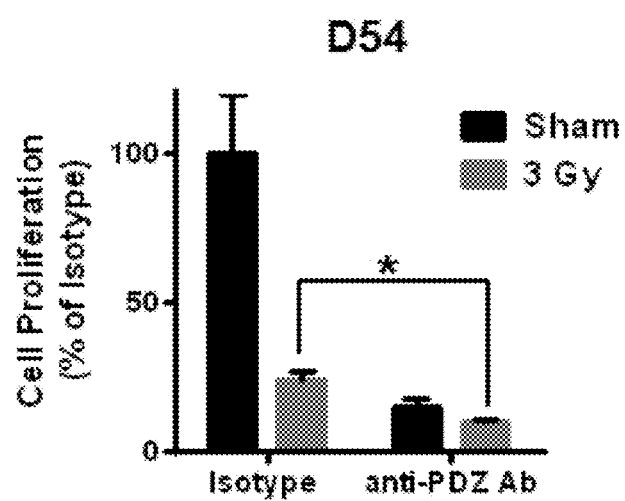
Figure 6M:
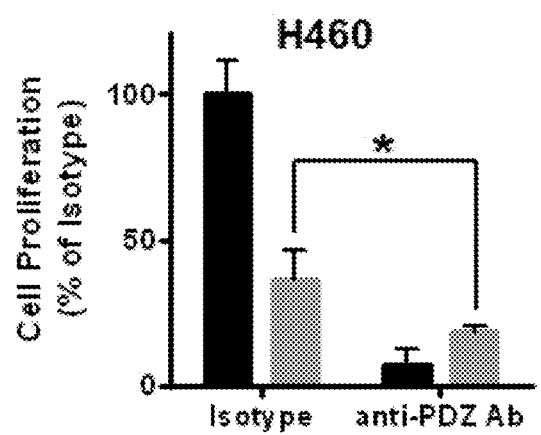
Figure 6N:
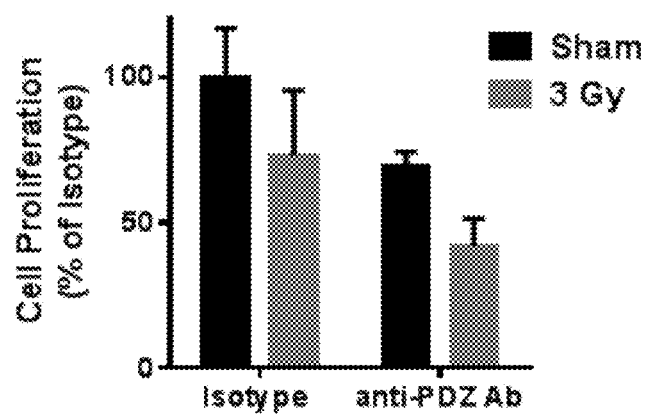
Figure 8A:
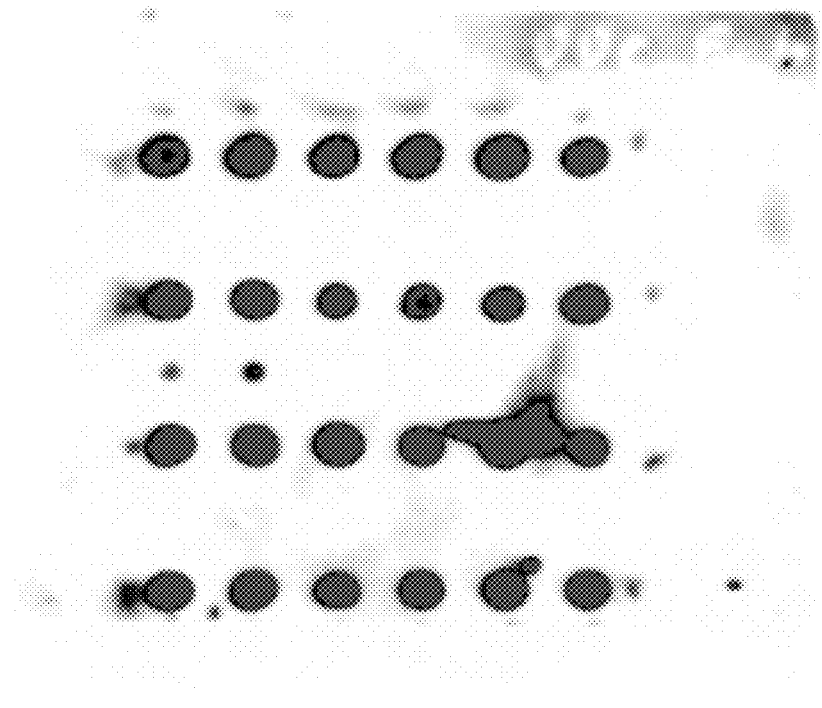
FIG. 8A and FIG. 8B depict images showing a dot blot assay of 24 positive clones out of 384 primary screened clones.
Figure 8B:
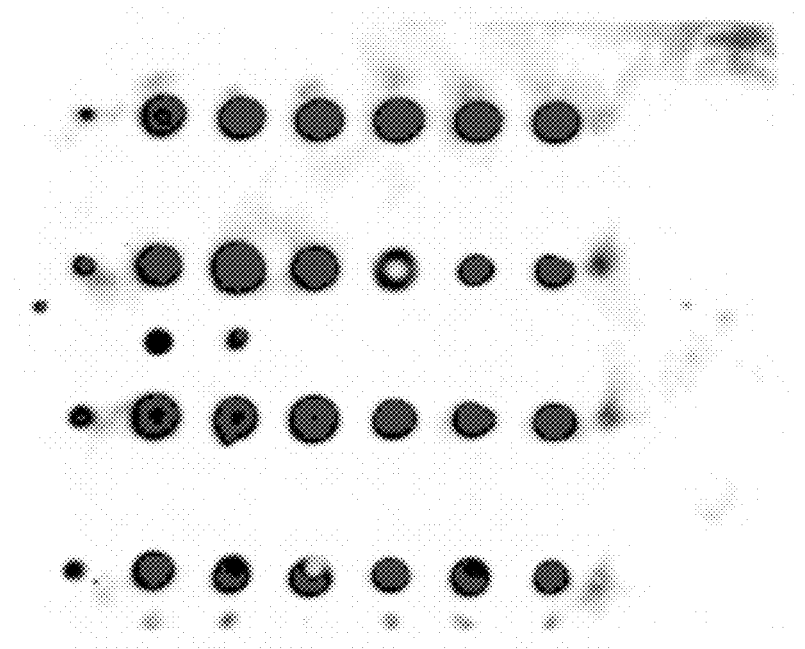

Tumors from mice were harvested after the completion of the tumor growth delay experiments and probed for AKT/mTOR signaling components (FIG. 6I and FIG. 6J). We observed downregulation of phospho-AKT and total AKT in tumors from mice treated with the anti-PDZ/TIP1 antibody compared to the tumors from mice treated with isotype control antibody (FIG. 6I). A similar reduction was also observed in the phospho-mTOR, total mTOR, and downstream targets of mTOR, phospho- and total 4EBP1 (FIG. 6J).

Discussion for Examples 1-6

TIP1 is a 14 kDa protein that is overexpressed in various cancer. It plays a vital role in tumor cell adhesion, migration and metastasis. TIP1 protein levels correlate with tumor progression and poor prognosis. TIP1 is composed of a single type I classic PDZ domain which selectively recognizes a C-terminal S/T-X-V/L-COOH motif of its interacting partners. TIP1 binding proteins include enzymes that participate in cell viability signaling pathways like PLC, PKC, GPCR, and Rho. Through these protein interactions, TIP1 demonstrates its versatility in biological functions, such as mediating the cellular response to serum starvation, inhibiting beta-catenin regulated gene transcription and cell proliferation, establishing polarity of epithelial cell, and protecting tumor cells from ionizing radiation-induced cell death. All these studies have indicated that TIP1 is a suitable molecular target for anti-cancer therapy.

The effect of anti-TIP1 antibody specifically binding to the PDZ domain on cell proliferation, colony formation, cell death, and tumor growth delay in vivo was evaluated. A dose and time-dependent reduction in the proliferation of U251, D54, A549 and H460 cell lines treated with the anti-PDZ antibody was observed (FIG. 1). Treatment of normal cells with the anti-PDZ antibody had no cytotoxic effect (FIG. 2). The site-specific cytotoxicity was observed with two antibodies, one of them specifically bound in the PDZ domain (anti-PDZ antibody) and the other that bound outside the PDZ domain (non-PDZ antibody) also referred as 2C6F3. Antibody-mediated cytotoxicity was observed only in treatments with the anti-PDZ Ab (FIG. 2). This indicated that the PDZ domain/binding groove in TIP1 plays a role in cancer cell proliferation.

TIP1 consists of six-stranded antiparallel β-barrel flanked by two α-helices. Crystal structures of TIP1 along with its interacting ligands show that the PDZ binding groove of TIP1 lies between the β2-strand and α2-helix. The ILGF motif is the important structural binding motif in this groove. The COOH group of the incoming ligand forms a hydrogen bond with the glycine (G) of this ILGF motif. Isoleucine (I), leucine (L) and phenylalanine (F) contribute hydrophobicity to the binding pocket. This hydrophobicity leads to the entry of the TIP1 ligand and stabilization of the interaction. The hairpin loop composed of the anti-parallel β-strands (βa and βb) is a unique structure present in TIP1, but absent in other PDZ domain containing proteins. Structural representation of the anti-PDZ antibody epitopes revealed that they spanned the entire hairpin loop, ILGF motif and the β2-strand of the PDZ binding groove, all of which are important for binding to TIP1 ligands (FIG. 3). This analysis suggests that the binding of the anti-PDZ antibody may be interfering with the interaction of TIP1 with its ligands, thereby inducing cytotoxicity. The non-PDZ antibody binds to the β1 strand that has not been reported to be involved in ligand interaction.

One mechanism of antibody-mediated tumor cell killing relies on antibody internalization. Cetuximab (chimeric IgG1), necitumumab (human IgG1) are examples of antibodies that target Epidermal Growth Factor Receptor (EGFR) which are internalized. Using spinning-disk live-cell microscopy we observed that anti-PDZ Ab was internalized as early as 2 h after treatment (FIG. 4A). The anti-PDZ Ab could be conjugated with cytotoxic drugs for delivery into intracellular compartments. It was observed that the GBM and NCSLC cells undergo apoptosis when treated with anti-PDZ antibodies (FIG. 4B). The mechanism of cell death by induction of apoptosis may involve p53 which are a well-known regulator of cell death. It has been reported that overexpression of TIP1 in glioma cells inhibits p53 activation and that depleting TIP1 resulted in the high accumulation of p53. This effect was mediated by LZAP (identified as a new binding partner of TIP1) which is involved in stabilization and nuclear translocation of p53. TIP1 has also been shown to bind the C-terminus of FAS which belongs to the TNF receptor family and involved in apoptosis. Blocking the PDZ domain of TIP1 with the anti-PDZ antibody may activate FAS-mediated apoptosis.

The AKT/mTOR pathway is an important regulator of cell proliferation, metabolism, and survival. GTPases are essential components of this pathway that act as molecular switches, cycling between a GTP-bound active form and a GDP-bound inactive form. Earlier we have reported that TIP1 was an essential protein for spatiotemporally coordinated activation of Rho GTPases (RhoA, Cdc42, and Rac1) in migrating GBM cells. In the present study, downregulation of the AKT/mTOR signaling following treatment with the anti-PDZ antibody was observed in both GBM and NSCLC cells (FIG. 5). AKT is downstream of Rac1, and its phosphorylation by Rac1 may be a feedback regulation mechanism. Since TIP1 knockdown resulted in decreased Rac1 activity, the anti-PDZ antibody could be downregulating AKT/mTOR pathway through Rac1 activity. TIP1 may also play a role directly or indirectly in the assembly of mTOR signaling protein complexes.

External beam radiotherapy (XRT) is a commonly used therapeutic modality for GBM and NSCLC. Meta-analysis of microarray datasets from GBM patients revealed that elevated TIP1 correlate with poor prognosis of human malignant gliomas after radiotherapy. Colony formation assays showed that the treatment with the combination of anti-PDZ Ab with XRT (4Gy) had an additive effect. TIP1 depletion in human GBM cell lines led to radiosensitization, whereas ectopic expression of TIP1 resulted in radioprotection. In the present study, treatment with anti-PDZ antibody alone resulted in significant reduction of colony formation in both GBM and NSCLC cells. Treatment of A549 and U251 tumor-bearing mice with the anti-PDZ Ab alone was able to significant delay tumor growth. Combination treatment of anti-PDZ Ab with radiation had an additive effect on tumor growth delay (FIG. 6). These results also indicate that radiation does not interfere with the cytotoxic effects of the anti-PDZ antibody. The persistent tumor growth delay by this antibody shows that antibody binding to the tumor may be blocking essential pathways required for tumor proliferation.

Overall, this study suggests that TIP1 is an effective molecular target for therapy of NSCLC and GBM. Blocking the PDZ binding groove with an anti-PDZ antibody is a strategy that has a direct cytotoxic effect on NSCLC and GBM and should be developed further for their therapy.

Methods for the Examples 1-5

Cell Lines, Chemicals, and Irradiation.

The human glioblastoma cell line D54 was a gift from Dr. Yancey Gillespie (University of Alabama at Birmingham). The human U251 glioblastoma cell line was obtained from the NCI. Human NSCLC cell lines A549 and H460 were obtained from ATCC. Mouse NSCLC cell line LLC and mouse glioblastoma cell line GL261 were obtained from ATCC. All of the cell lines were evaluated for *Mycoplasma* and tested negative. D54, LLC and A549 cells were cultured in DMEM/F-12; U251, GL261, and H460 were cultured in RPMI media containing 10% fetal bovine serum (FBS) and 1% penicillin-streptomycin (P/S). All cell cultures were grown in a humidified incubator at 37° C. with 5% CO2. Goat anti-TIP1 polyclonal antibody was obtained from Santa Cruz. The cells and the mice were irradiated with an RS2000 160 kV X-ray Irradiator using a 0.3 mm copper filter (Rad Source Technologies, Suwanee, Ga., USA).

Antibodies.

The TIP1 antibody that specifically bound to the PDZ domain (anti-PDZ antibody) was obtained from Santa Cruz. The antibody that bound outside the PDZ domain (anti-non-PDZ antibody) which we also refer as 2C6F3 was made and characterized by us earlier. The phospho-Akt (S473), total Akt, phospho-mTOR (S2448), total mTOR, phospo-P70S6 (T389) total-P70S6 phospo-4EBP1 (T70), 4EBP1 (T70) and GAPDH antibodies were purchased from cell signaling.

Trypan Blue Dye Exclusion Assays.

Cancer cells (A549, H460, U251, and D54) were seeded at a density of 10,000 cells/well in 12 well plates and treated with 1 µg/ml of anti-PDZ antibody or isotype antibody as control and allowed to incubate for 24 h, 48 h, 72 h and 96 h. The cells were then trypsinized and counted using a ViCell cell viability analyzer (Beckman Coulter). Cell proliferation was normalized as the percentage of isotype control. Three independent experiments having triplicates for each treatment were performed for each cell line.

Cancer cells (A549, LLC, D54 and GL261) and Normal cells (MRCS and HUVEC) were seeded at a density of 10,000 cells/well in 12 well plates and treated with either 1 µg/ml of anti-PDZ antibody or 1 µg/ml of anti-non-PDZ and allowed to incubate for 96 h. The cells were then trypsinized and counted using a ViCell cell viability analyzer (Beckman Coulter). Cell proliferation was normalized as the percentage of isotype control. Three independent experiments having triplicates for each treatment were performed for each cell line.

CRISPR/Cas9 Mediated Knockout of TIP1.

We performed CRISPR/Cas9 mediated knockout of TIP1 as previously described. Briefly, 2 different guide RNAs (sgRNA 1: CCAGGGTATTTATGTCACAC (SEQ ID NO: 16) and sgRNA 2: CATTGGAGGTGGAATCGACC (SEQ ID NO: 17)) were cloned into the pLentiCRISPRV2 vector. Unmodified vector was used as the CRISPR control in all experiments. After validation of the insertion by sequencing, lentivirus mediated transduction of cells was performed. Cells were selected with puromycin and stable clones were validated for knockout of TIP1 by western blots.

Structural Representation of Anti-PDZ Epitope on 3D Structure of TIP-1.

The location of the epitopes of anti-PDZ antibody and non-PDZ antibody was overlaid on the already published crystal structure of TIP1, 3DIW (22). PyMOL software was used overlay the epitopes of anti-PDZ antibody and non-PDZ antibody on the 3D structure of TIP1.

Antibody Internalization Assays by Live Cell Imaging.

A549 cells were seeded into glass bottom chamber slides (Mattek) in phenol red-free medium. The following day, cells were stained with a cell mask orange dye (Invitrogen) as per manufacturer's instructions. The cells were then treated with Alexa-Flour 488 labeled anti-PDZ antibody and visualized using a spinning disk fluorescent microscope (Nikon). Live cell images were captured every 5 minutes and acquisition was continued for 24 h.

Annexin V Apoptosis Assay.

Cancer cells (A549, H460, U251 and D54) were treated with 1 µg/ml anti-PDZ antibody or isotype control and irradiated with 3 Gy and incubated for 96 h. The cells were collected 96 h post irradiation and stained with Annexin V-FITC and PI (BD Biosciences) as per the manufacturer's protocol. The cells were analyzed for apoptosis by flow cytometry using an MACSQuant Analyzer (Miltenyi Biotech).

Cell Cycle Analysis.

Cell cycle analysis was performed after treatment of cells with the anti-PDZ/TIP1 antibody for 96 h. Briefly, 1×106 cells were fixed in 70% ethanol for 1 h. The samples were then treated with 1 mg/mL RNase A for 30 min at 37° C. and stained with Propidium iodide (50 p,g/mL). The samples were acquired in a flow cytometer (MACSQuant Analyzer, Miltenyi Biotec) after 10 min incubation. The distribution of cells in GO/G1, S and G2/M phases of cell cycle was estimated using the ModFit LT software.

Western Immunoblot Analysis.

Cancer cells (A549, H460, U251, and D54) were treated with 1 µg/ml anti-TIP-1 antibody or isotype control and allowed to incubate for 96 h and then lysed using M-PER mammalian protein extraction reagent (Thermo-Fisher Scientific). Protein extracts were immunoblotted and probed using antibodies against phospho-Akt (Ser 473), total-Akt, phospho-mTOR (Ser 2448), total-mTOR, phospho-p70S6 kinase, total-p70S6 kinase, phospho-4EBP1, total-4EBP1 (Cell Signaling Technology). The blots were probed with GAPDH for protein loading (Cell Signaling Technology). The blots were visualized using the ChemiDoc-MP Imaging System (Bio-Rad) and analyzed with Image Lab Software (Bio-Rad).

Colony Formation Assays.

Cancer cells (A549, H460, U251, and D54) were treated with 1 µg/ml anti-PDZ antibody and allowed to incubate for 96 h. Cells were then sub-cultured in six-well plates and irradiated with 0 or 3 Gy. The cells were incubated for 7-10 days and the colonies were stained with 0.5% crystal violet. Colonies comprising of 50 cells or more were counted under a StemiVD4 dissecting microscope (Zeiss). The survival fractions were calculated after normalizing to the plating efficiency and presented as surviving fractions relative to control.

Tumor Growth Delay.

All animal studies were performed in accordance with the guidelines of the IACUC and with protocols approved by the Washington University Division of Comparative Medicine. Heterotopic tumor models were established by injecting A549 ($3\times10^6$) and U251 ($1\times10^6$) cells subcutaneously into the hind limbs of 6-8 week-old female athymic nude mice (Envigo, USA). The tumor-bearing mice were serpentine sorted by tumor volume and distributed into four groups having 5 mice each with an average tumor volume of 200 $mm^3$. The treatment groups were as follows (a) 300 µg/kg isotype control antibody; (b) 300 µg/kg isotype control antibody combined with XRT; (c) 300 µg/kg anti-TIP-1 antibody; and (d) 300 µg/kg anti-TIP-1 antibody combined with XRT. The tumors in XRT groups were irradiated with 2Gy per day for five consecutive days after shielding the rest of the body with lead. The antibodies were injected via the tail vein on days 1 and 4 of the treatment. The tumor volumes were measured using a digital caliper on the indicated days.

Statistics.

Statistical analyses were performed using the Student's t-test and or one-way or two-way analysis of variance (ANOVA). Bonferroni's multiple comparisons test was applied where necessary. These analyses were performed using Prism 6 (GraphPad Software, La Jolla, Calif., USA), and statistical significance is indicated in each graph where appropriate.

Example 7. ELISA with 6 Purified Anti-PDZ ScFv Peptides

Figure 9A:
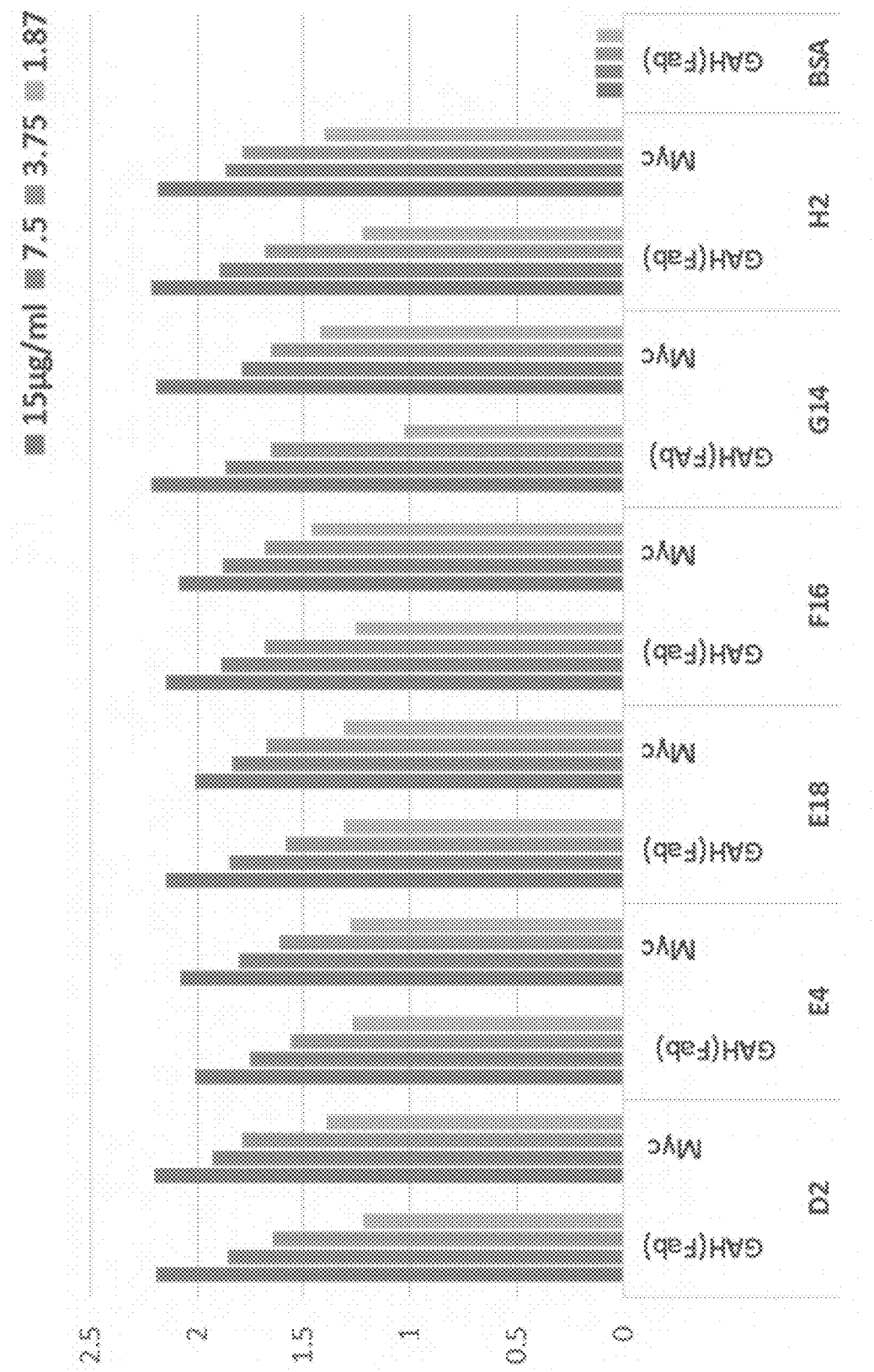
FIG. 9A and FIG. 9B depict graphs showing ELISA data of 6 purified anti-PDZ peptide scFvs.
Figure 9B:
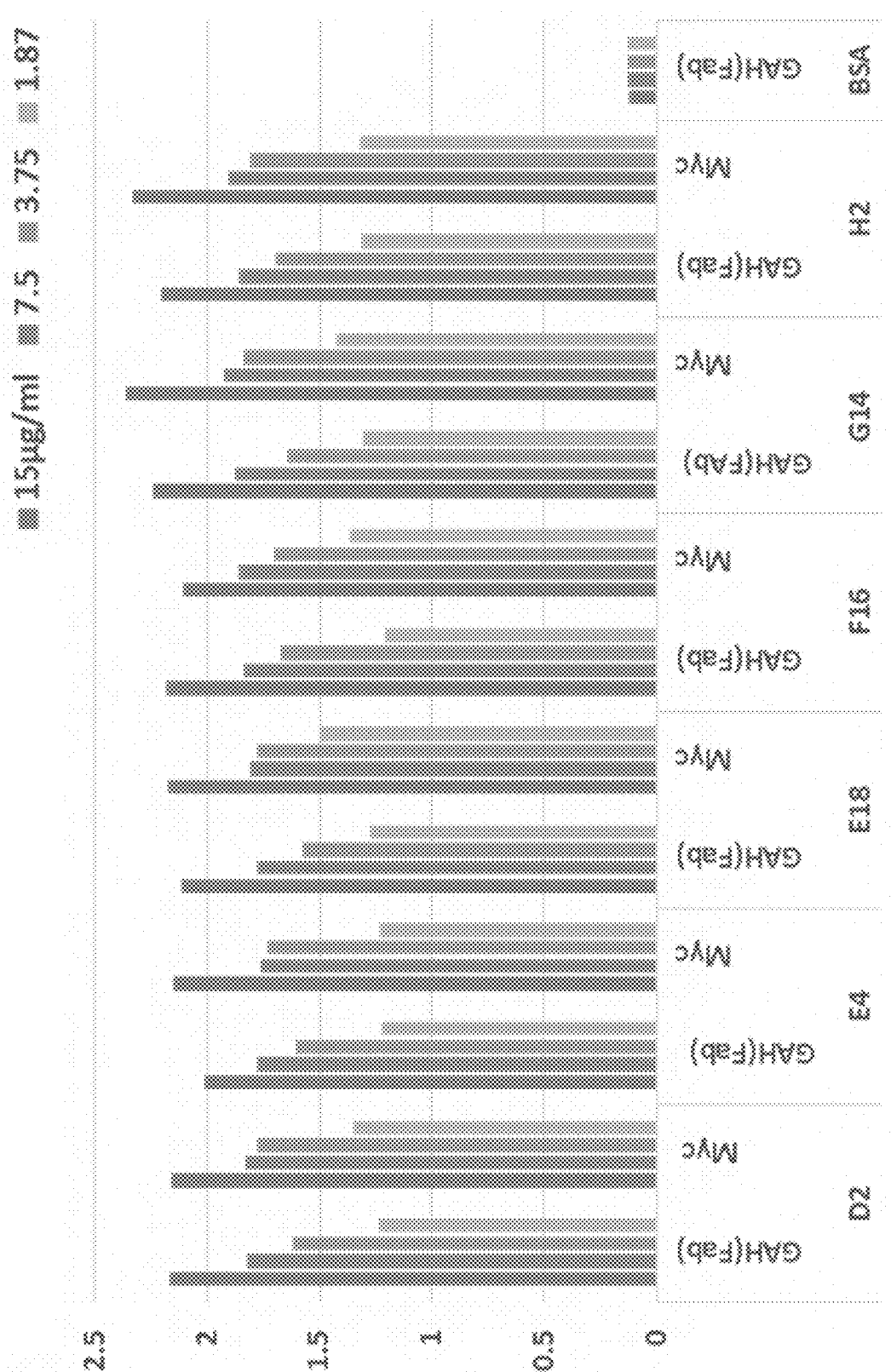

ELISA plates were coated with 50 µl/well of PDZ peptide or Tip 1 protein, in the concentration of 15 µl/ml, 7.5 µl/ml, 3.75 µl/ml, 1.87 µl/ml. The coated wells were washed three times with Phosphate Buffered Saline (PBS). The wells were then blocked with Bovine Serum Albumin (BSA) in 0.1% Tween 20 PBS. The wells were washed three times with PBS, followed by 50 µl/ml of serial diluted SCFvs. The serial dilutions used were 15 µl/ml, 7.5 µl/ml, 3.75 µl/ml, 1.87 µl/ml. Six purified clones of anti-PDZ ScFv, designated as D2, E4, E18, F16, G14, and H2 were used, BSA was used as control. The wells were washed again 3 times with PBS, filled with 50 µl/well of goat anti human IgG (Fab)2 or mouse anti-Myc antibody. Washed 3 times with PBS followed by 50 µl/well of donkey anti-goat-HRT or rabbit anti-mouse IgG-HRP conjugate secondary antibody, in the wells with goat anti human IgG (Fab)2 or mouse anti-Myc antibody, respectively. The wells are washed again three times. The well were filled with ABTS substrate. The absorbance was read by an ELISA reader at 405 nm. The absorbance was read against a standard curve. Decrease in concentration of anti-PDZ SCFv lead to decreased binding with PDZ peptide (FIG. 9A) and Tip-1 protein (FIG. 9B), for all 6 tested anti-PDZ ScFv clones, indicating a efficiency of binding of the anti-PDZ ScFv to PDZ peptide and Tip 1 protein.

Example 8. Western Blot Assay of Anti-PDZ ScFv Clones

Irradiated tumor cells, 3GYX3 A549 cells were lyzed and the lysate loaded on a 15% SDS-PAGE gel (FIG. 10A). Recombinant Tip 1 protein was loaded on another 15% SDS-PAGE gel (FIG. 10B). Both gels were run and transferred to a membrane and reacted with anti-PDZ peptide SCFv detected by anti-Myc antibody. The bound anti-PDZ SCFvs on the cell lysate blot (FIG. 10A) and recombinant Tip 1protein blot (FIG. 10B) are shown as 15 kD bands. Anti-PDZ SCFvs clones G14 and H2 are shown in lane 4 and 7 of the blots, respectively (FIG. 10A, FIG. 10B).

Example 9. Effect of Anti-PDZ ScFv Clones on Tumor Cell Viability

Tumor cells were loaded on a 96 well plate. Tumor cells used were D54, U251, U87, MBA231, OE33, A549, and H460. The cells were either irradiated or sham treated ((3GYX3 and 0GY). 96 hours after treatment, the culture medium in the wells was replaced by serum-free medium. Diluted anti-PDZ SCFvs were added into wells to form the final concentration of 10 µg/ml. The anti-PDZ SCFv clones used were G14, H2, and D2, shown in FIG. 11A, FIG. 11B, and FIG. 11C, respectively. The cells are cultured for 24 hours, and 1/10 the Cell-counting Kit-8 (CCK-8) cell viability serum agent (Biotool.com) was added to each well. The color development was read at 450 nm.

Figure 11A:
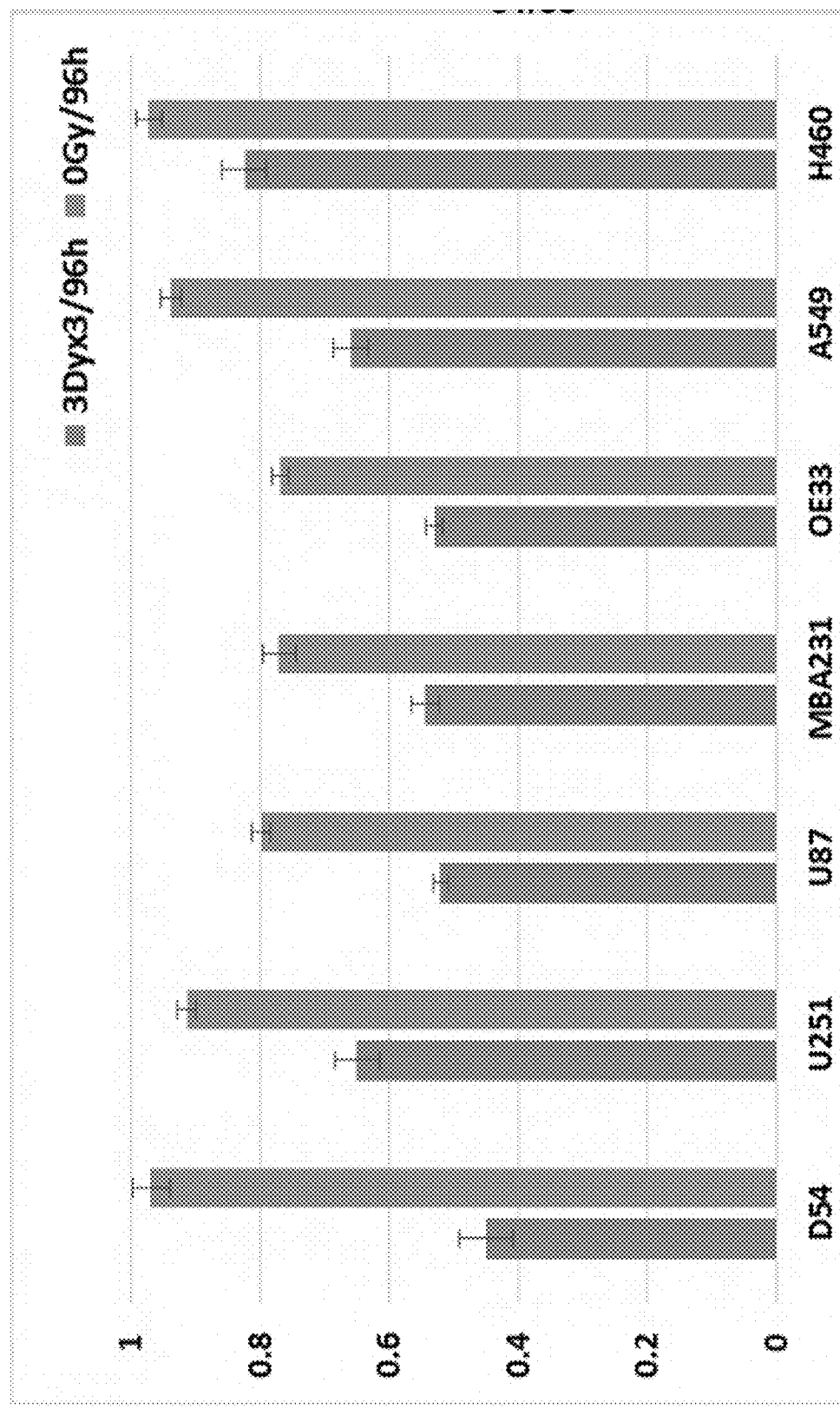
FIG. 11A, FIG. 11B and FIG. 11C depicts graphs showing tumor cell viability by CCK-8 assay.
Figure 11B:
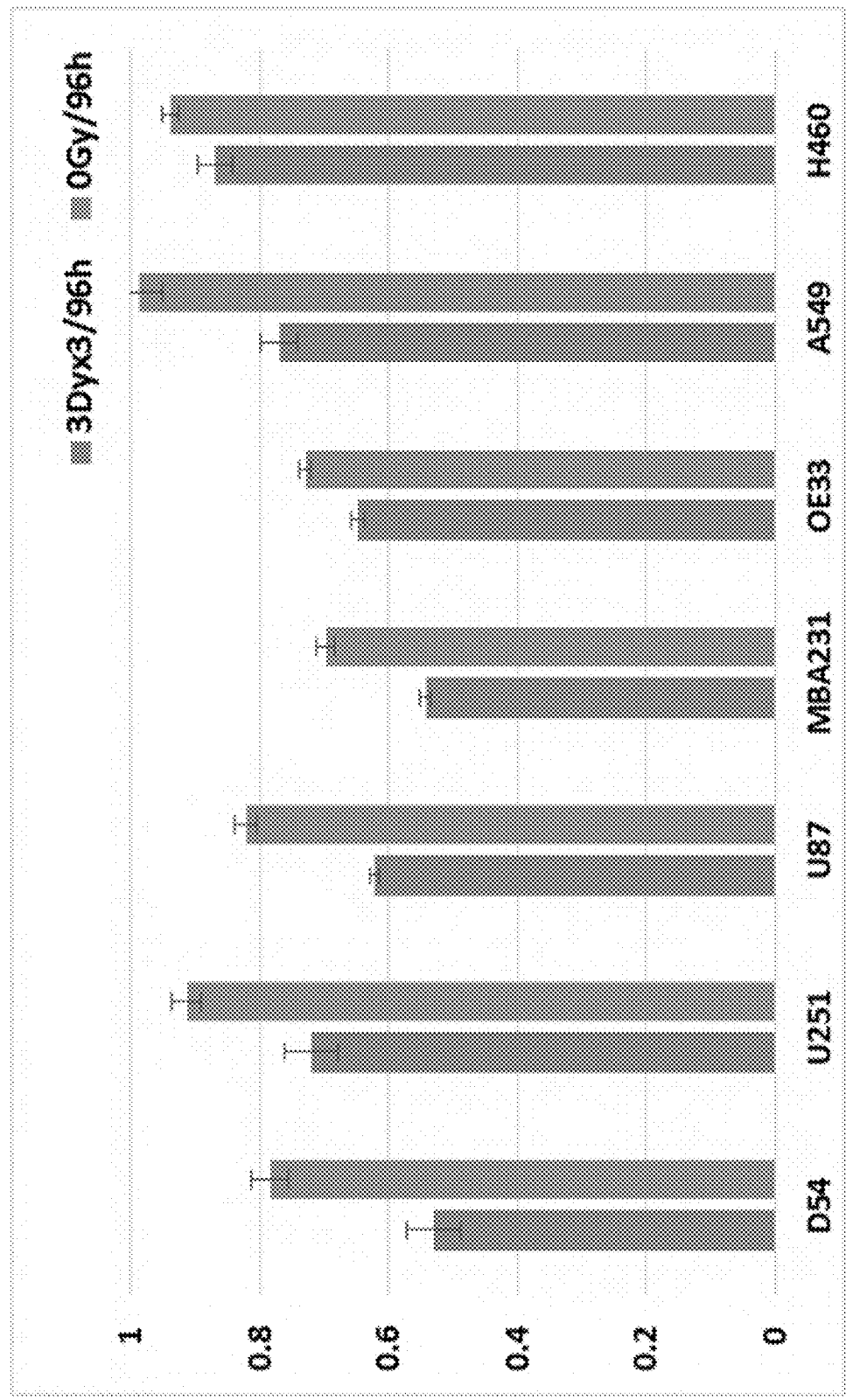
Figure 11C:
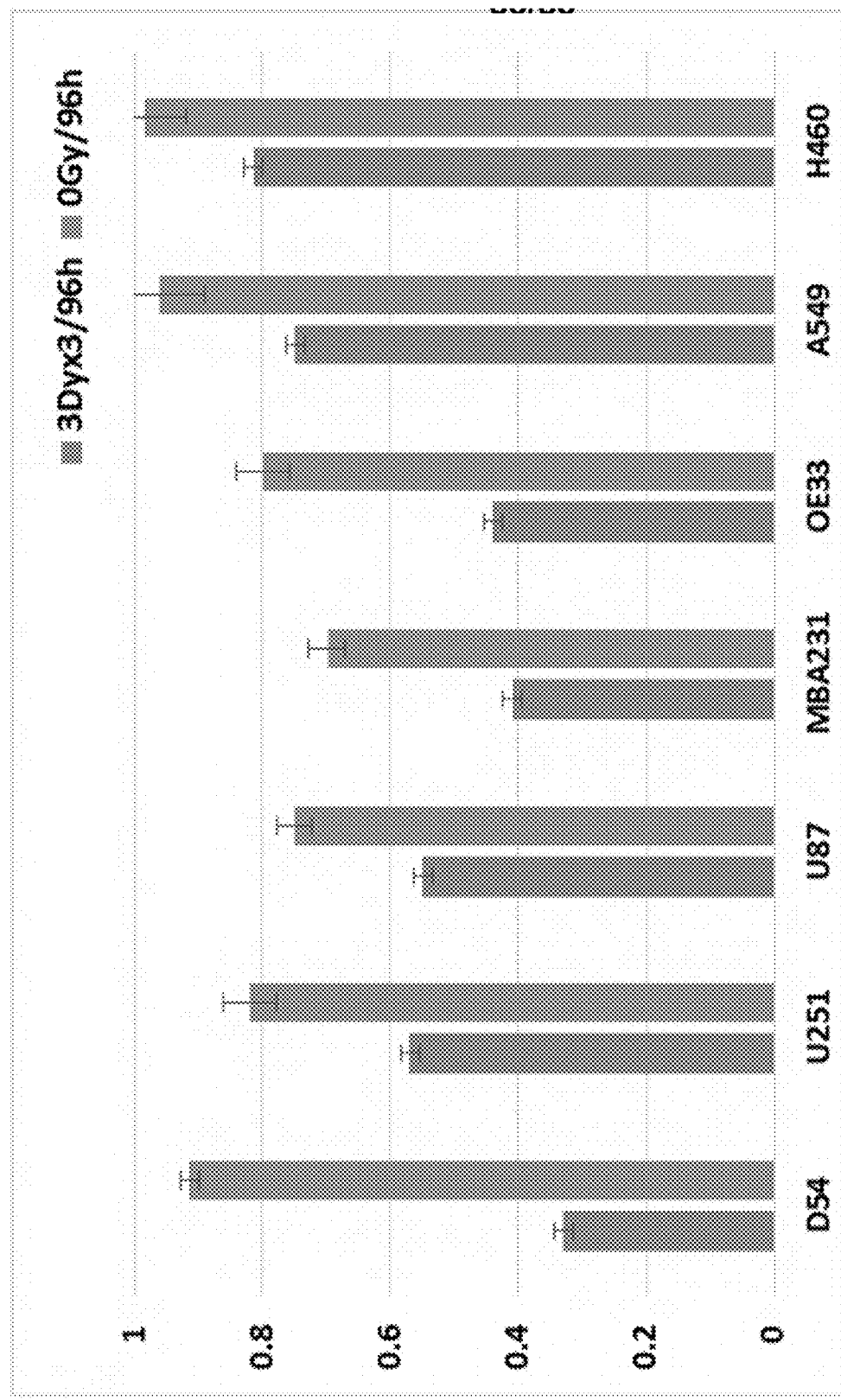

The cell viability was calculated by the formula: Cell viability (%)=Absorbance (drug+)−((Absorbance (blank)/absorbance (drug−)×100). The assay is based on the measuring of the dehydrogenases activity in the tumor cells. The dehydrogenase activity decreases with decrease in viability. He irradiated cells treated with ScFv had decreased cell viability compared to the sham treated cells, for all three clones used (FIG. 11A, FIG. 11B, and FIG. 11C).

Example 10. Effect of Anti-PDZ ScFv on Cell Proliferation

Figure 12A:
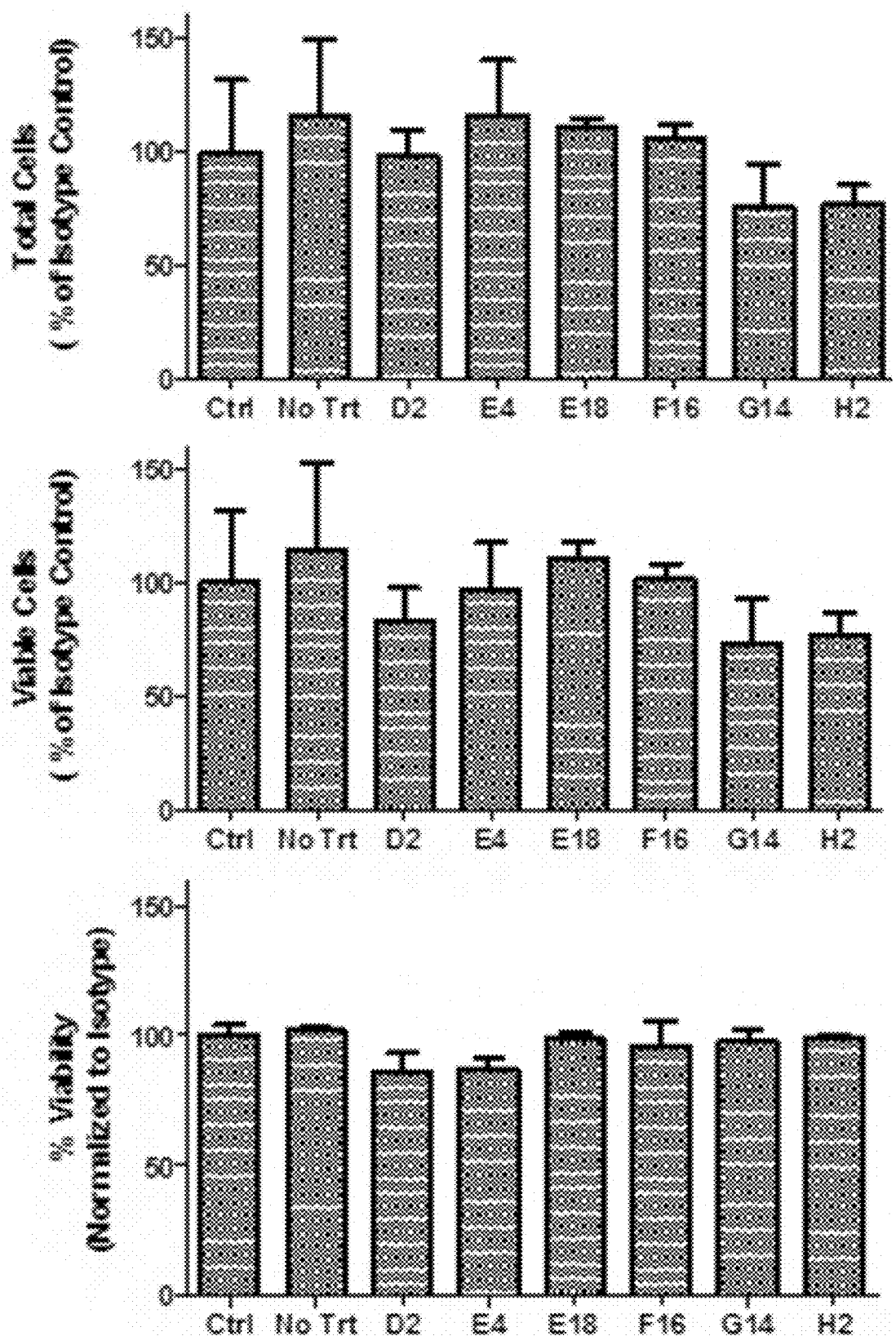
FIG. 12A and FIG. 12B depict graphs showing results from a tumor cell viability assay.
Figure 12B:
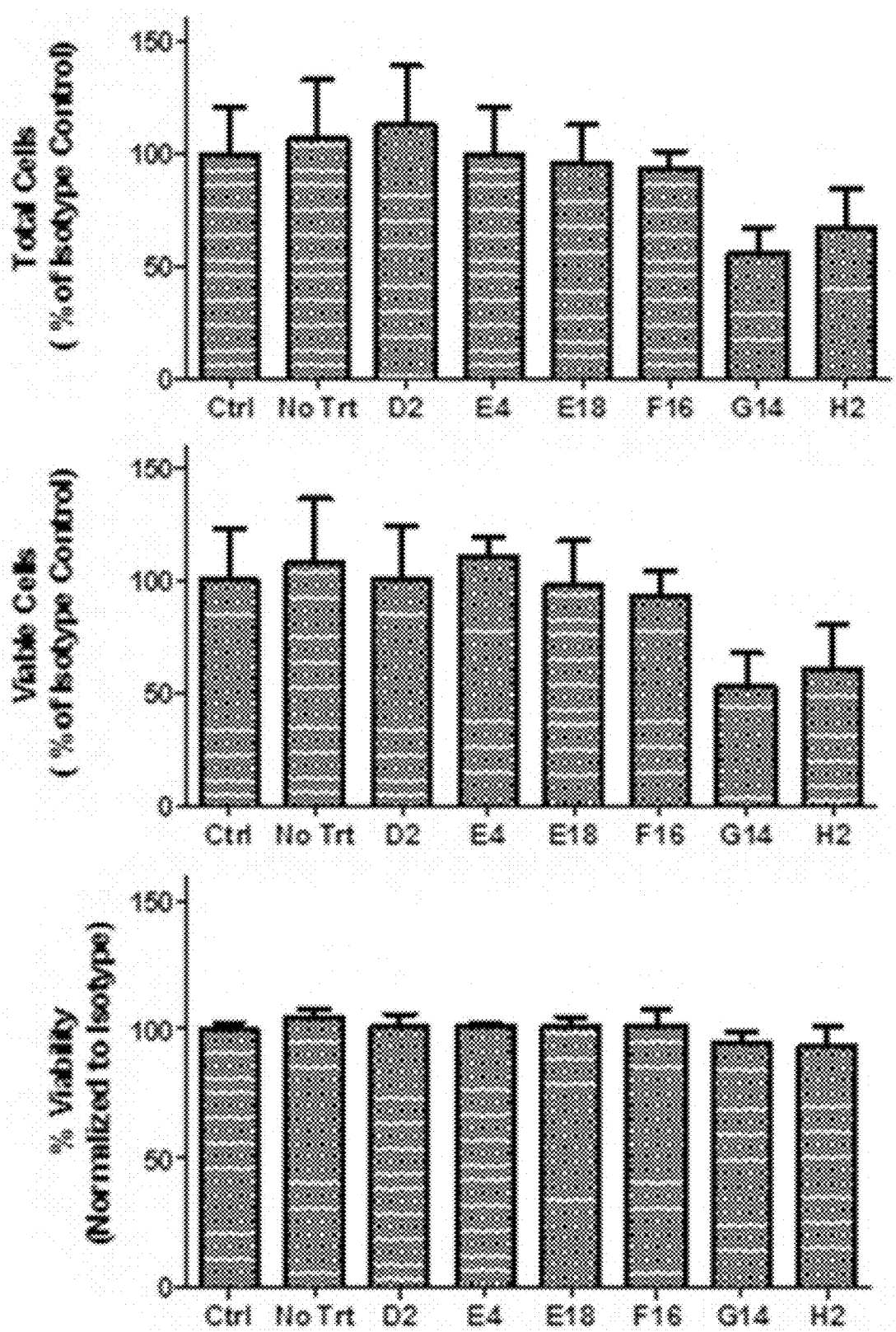

Tumor cells were plated on 24 well plates (4000 cells/well) on Day 0. On Day 1, the cells were treated with 100 mg/ml of anti-PDZ ScFvs clones. The anti-PDZ ScFvs clones used were D2, E4, E18, F16, G14, and H2. 96 hours post-treatment, the wells were rinsed with PBS and cells trypsinized and collected. The total and viable count were measured by trypan blue exclusion assay. Data was normalized to the isotope. Mean±SD from triplicates in present in FIG. 12A and FIG. 12B for A549 and U251 tumor cells respectively.

Figure 15A:
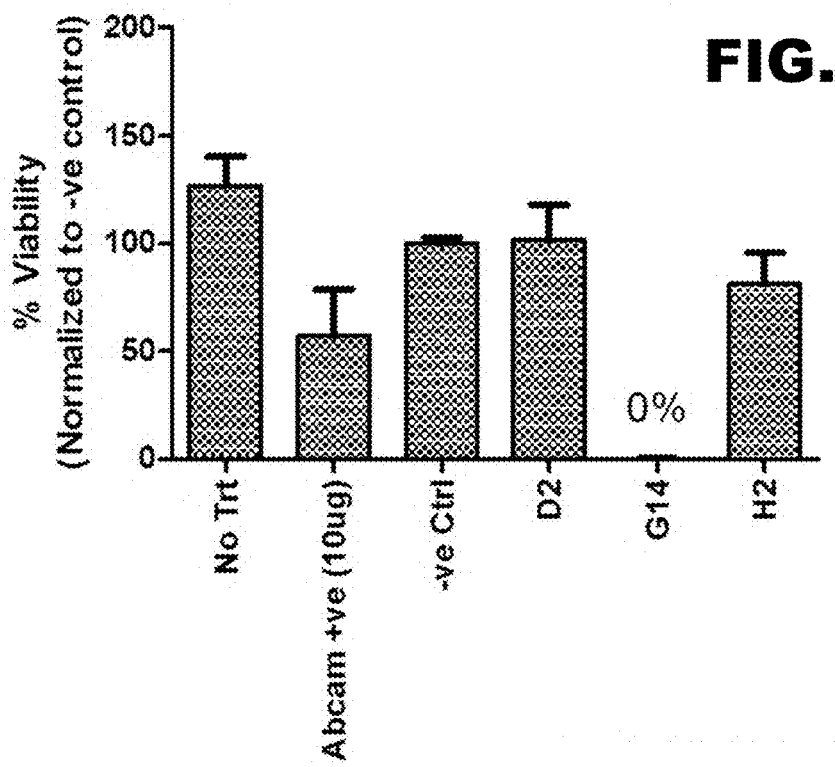
FIG. 15A and FIG. 15B depict graphs showing viable cells following treatment with scFvs of the disclosure.
Figure 15B:
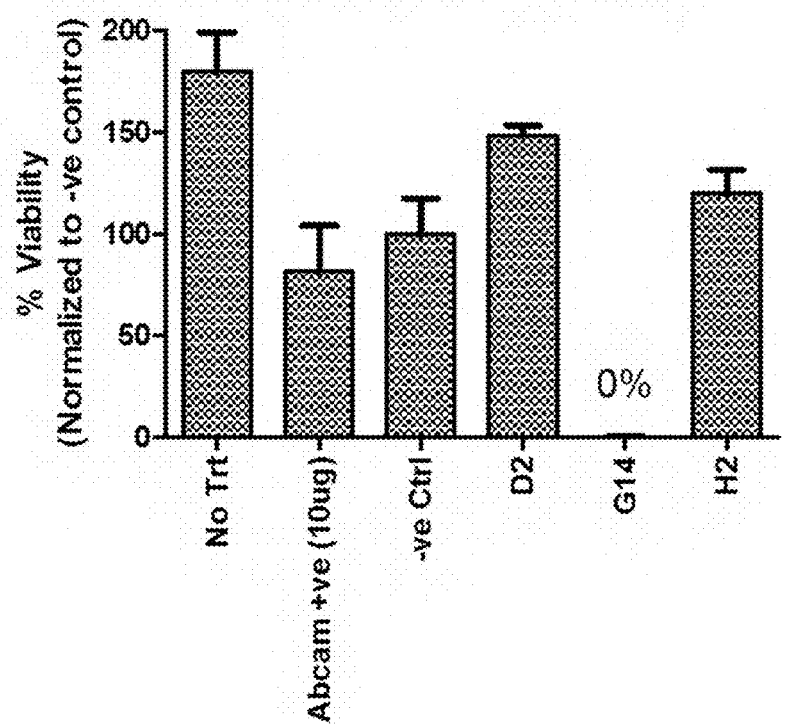

In another experiment, H640 cells were plated on Day 0 on a 24 well plate (7500 cells/well). On Day 1, cells were treated with 10 µg/ml (FIG. 15A) or 15 µg/ml (FIG. 15B) of respective scFv's and 10 µg/ml commercial Antibody as positive control. 96 hours post-treatment, the wells were rinsed with PBS and cells were trypsinized and collected. The total and viable count were measure by trypan blue exclusion assay. Data was normalized to the Isotype. Mean±SD from triplicates is presented.

Figure 13A:
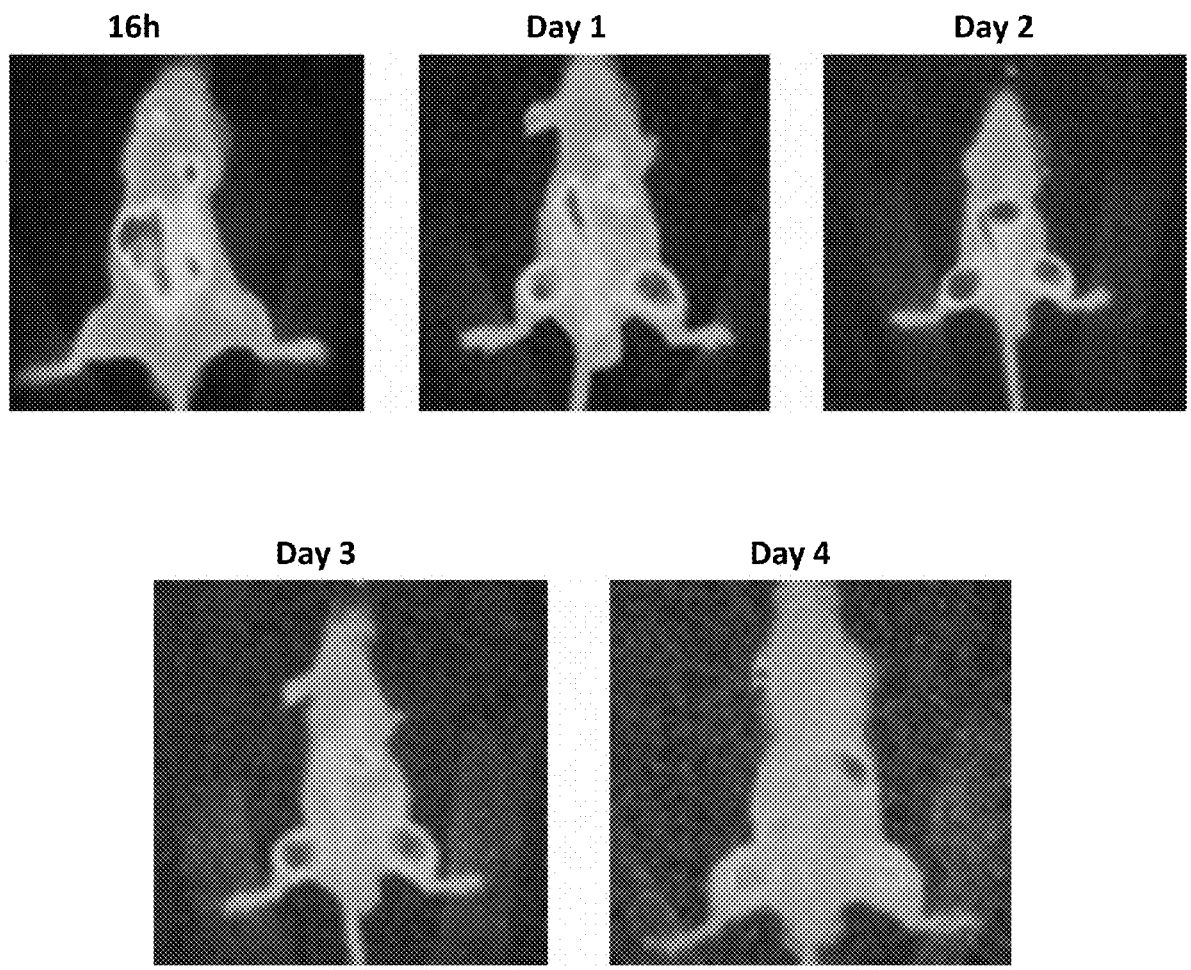
FIG. 13A depicts optical imaging on tumor bearing nude mice treated with anti-Tip1 PDZ domain scFv.
Figure 13B:
FIG. 13B depicts optical imaging on tumor bearing nude mice treated with control scFv.
Figure 13B:
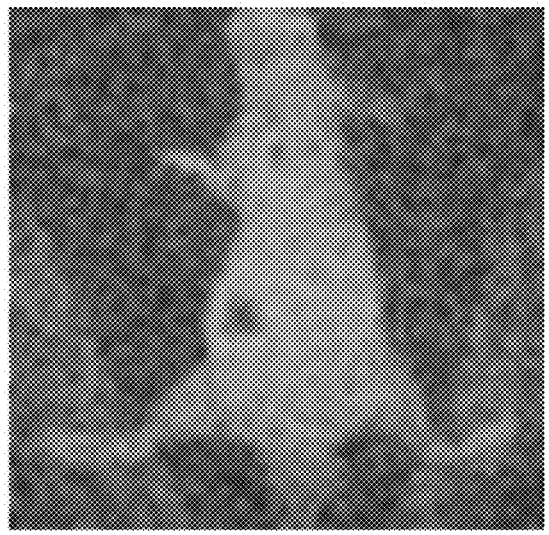
Figure 13B:
Figure 13B:

Example 11. Optical Imaging of Tumor Bearing Nude Mice Treated with Anti-PDZ ScFv Purified anti-PDZ ScFv TE11 clone conjugated with Alexaflor® 750 dye (FIG. 13A) or control Scfv conjugated with Alexaflor® 750 dye (Bottom, FIG. 13B) was injected intravenously into Lewis Lung Carcinoma (LLC) tumor bearing mice. The left hind limb of ice were irradiated (3GY X3), and the right hind limbs were sham irradiated. The mice were imaged at 16 hours, Day 1, Day2, Day 3, and Day 4 of treatment. The optical images show that the anti-PDZ ScFv bound to the tumor cells as shown in the high intensity of red color (conjugated Alexaflor® 750 dye) shown on FIG. 11A, 16h. The red color intensity decreases, as the anti-PDZ ScFv kills the tumor cells over time. Images on Day 4 of treatment have the least intensity of red color.

Example 12. ELISA, Affinity and FACS of 2F10, 3D6, and 7H5

Figure 16A:
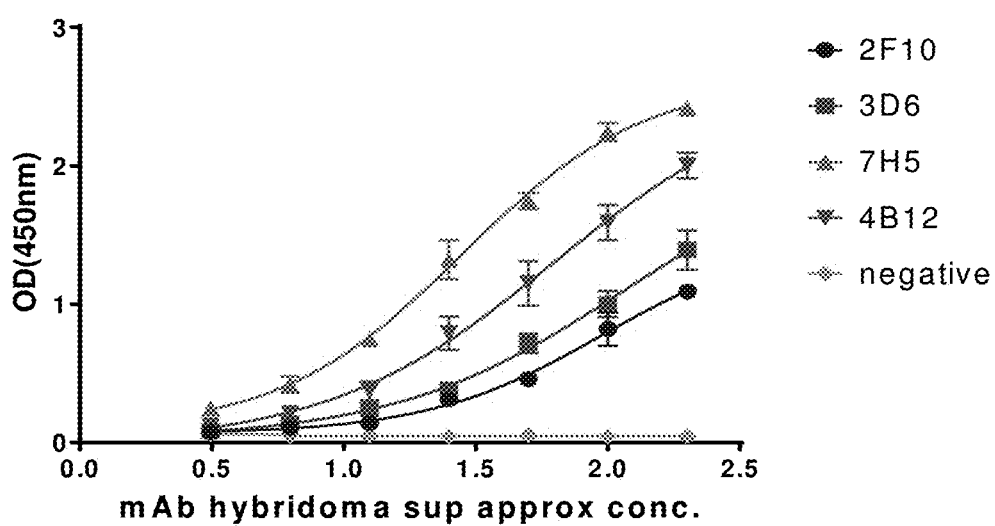

Indirect ELISA was performed using standard procedures. Briefly, 10 ug purified recombinant TIP1 protein was coated overnight in 96-well ELISA plates. Next day, wells were blocked with 3% milk and left overnight in the refrigerator. Following day, various 2-fold dilutions of the hybridoma supernatants were prepared in 3% milk and added to the wells in duplicate. The plates were then washed with PBS-0.1% Tween 20 buffer and incubated with anti-mouse HRP conjugated antibodies. Following washing with PBST, plates were developed with TMB substrate and absorbance read in a plate reader at 450 nm. The saturation curves of 2F10, 3D6, 7H5, abd 4B12 are shown in FIG. 16A.

Biacore 2000 instrument was used to evaluate the affinity of the purified mouse monoclonal anti-TIP1 antibodies. Briefly, CM5 sensor chip was coated with recombinant purified TIP1 protein using the amine coupling wizard. Various concentrations of the purified antibodies were passed over the immobilized TIP1. BIAevaluation software was used for fitting the sensorgrams and deducing the association (KA) and dissociation (KD) constants listed in FIG. 16B.

Figure 16C:
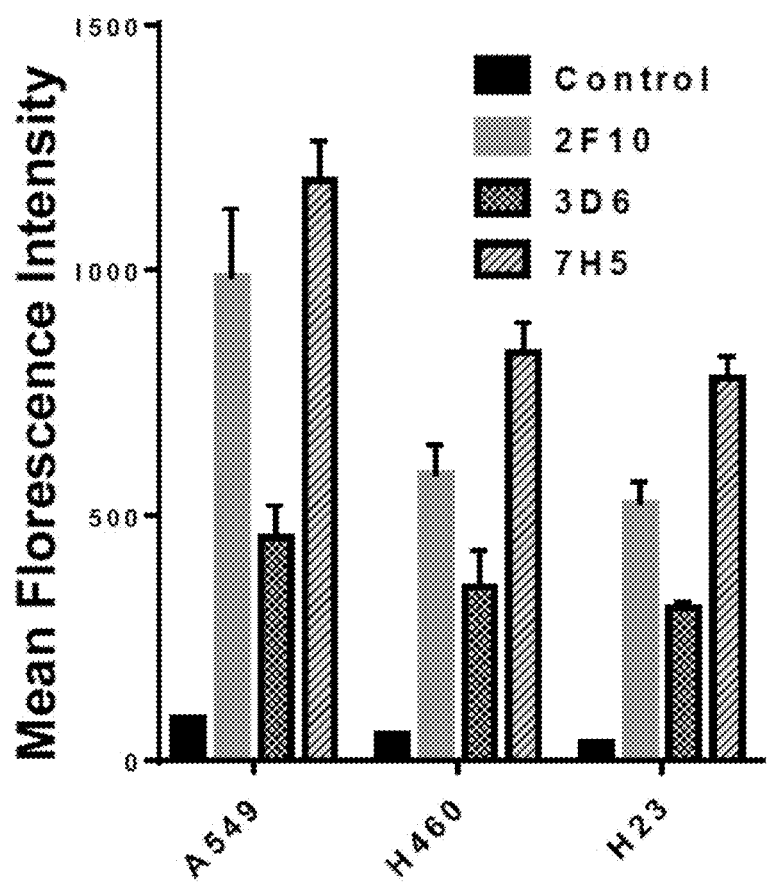

A549, H460 and H23 cells were incubated with the hybridoma supernatants on ice for 1 h. The cells were then washed with FACS staining buffer (PBS, 5% FBS, 0.01% sodium azide) and incubated with alexa-flour 488 conjugated anti-mouse antibody for 1 h on ice. Following washing with FACS buffer, cells were acquired in the MACSQuant Analyzer flow cytometer. The mean fluorescence intensity for 2F10, 3D6, and 7H5 are reported in FIG. 16C.

REFERENCES

1. Siegel R L, Miller K D, Jemal A. Cancer statistics, 2015. C A: a cancer journal for clinicians. 2015; 65:5-29.
2. Ferlay J, Shin H R, Bray F, Forman D, Mathers C, Parkin D M. Estimates of worldwide burden of cancer in 2008: GLOBOCAN 2008. International journal of cancer. 2010; 127:2893-917.
3. Rosell R, Karachaliou N. Lung cancer: Maintenance therapy and precision medicine in NSCLC. Nat Rev Clin Oncol. 2013; 10:549-50.
4. Zhang Y, Guessous F, Kofman A, Schiff D, Abounader R. XL-184, a MET, VEGFR-2 and RET kinase inhibitor for the treatment of thyroid cancer, glioblastoma multiforme and NSCLC. Idrugs. 2010; 13:112-21.
5. Passaro A, Lazzari C, Karachaliou N, Spitaleri G, Pochesci A, Catania C, et al. Personalized treatment in advanced ALK-positive non-small cell lung cancer: from bench to clinical practice. Onco Targets Ther. 2016; 9:6361-76.
6. Donovan E A, Kummar S. Targeting VEGF in Cancer Therapy. Current Problems in Cancer. 2006; 30:7-32.
7. Wang H, Han M, Whetsell W, Wang J, Rich J, Hallahan D, et al. Tax-interacting protein 1 coordinates the spatiotemporal activation of Rho GTPases and regulates the infiltrative growth of human glioblastoma. Oncogene. 2014; 33(12):1558-69.
8. Wang H, Yan H, Fu A, Han M, Hallahan D, Han Z. TIP-1 translocation onto the cell plasma membrane is a molecular biomarker of tumor response to ionizing radiation. PLoS One. 2010; 5:e12051.
9. Hariri G, Yan H, Wang H, Han Z, Hallahan D E. Radiation-guided drug delivery to mouse models of lung cancer. Clin Cancer Res. 2010; 16:4968-77.
10. Kanamori M, Sandy P, Benetti R, Kai C, Hayashizaki Y, al. e. The PDZ protein taxinteracting protein-1 inhibits beta-catenin transcriptional activity and growth of colorectal cancer cells. J Biol Chem. 2003; 278(40):38758-64.
11. Kay B, Kehoe J. PDZ domains and their ligands. Chem Biol 11:423-425. 2004.
12. Zoetewey D L, Ovee M, Banerjee M, Bhaskaran R, Mohanty S. Promiscuous binding at the crossroads of numerous cancer pathways: insight from the binding of glutaminase interacting protein with glutaminase L. Biochemistry. 2011; 50:3528-39.
13. Alewine C, Olsen O, Wade J B, Welling P A. TIP-1 has PDZ scaffold antagonist activity. Molecular biology of the cell. 2006; 17:4200-11.
14. Hampson L, Li C, Oliver A W, Kitchener H C, Hampson I N. The PDZ protein Tip-1 is a gain of function target of the HPV16 E6 oncoprotein. International journal of oncology. 2004; 25:1249-56.
15. Han M, al. e. Expression of TIP-1 confers radioresistance of malignant glioma cells. PloS one. 2012; 7(9): e45402.
16. Han M, al. e. Expression of Tax-interacting protein 1 (TIP-1) facilitates angiogenesis and tumor formation of human glioblastoma cells in nude mice. Cancer Lett. 2013; 328(1):55-64.
17. Han M, Wang H, Zhang H, Han Z. The PDZ protein TIP-1 facilitates cell migration and pulmonary metastasis of human invasive breast cancer cells in athymic mice. Biochem Biophys Res Commun. 2012; 422(1):139-45.
18. Harris B Z, Lim W A. Mechanism and role of PDZ domains in signaling complex assembly. Journal of cell science. 2001; 114:3219-31.
19. Mohanty S, Ovee M, Banerjee M. PDZ Domain Recognition: Insight from Human Tax-Interacting Protein 1 (TIP-1) Interaction with Target Proteins. Biology. 2015; 4:88-103.
20. Han M, Wang H, Zhang H T, Han Z. Expression of Tax-interacting protein 1 (TIP-1) facilitates angiogenesis and tumor formation of human glioblastoma cells in nude mice. Cancer letters. 2013; 328:55-64.
21. Yan H, Kapoor V, Nguyen K, Akers W J, Li H, Scott J, et al. Anti-tax interacting protein-1 (TIP-1) monoclonal antibody targets human cancers. Oncotarget. 2016; 7:43352-62.
22. Zhang J, Yan X, Shi C, Yang X, Guo Y, Tian C, et al. Structural basis of beta-catenin recognition by Tax-interacting protein-1. J Mol Biol. 2008; 384:255-63.
23. Franken N A, Rodermond H M, Stap J, Haveman J, van Bree C. Clonogenic assay of cells in vitro. Nat Protoc. 2006; 1:2315-9.
24. Li H-F, Kim J-S, Waldman T. Radiation-induced Akt activation modulates radioresistance in human glioblastoma cells. Radiation Oncology (London, England). 2009; 4:43-.
25. Fan Q-W, Weiss W A. Targeting the RTK-PI3K-mTOR Axis in Malignant Glioma: Overcoming Resistance. Current topics in microbiology and immunology. 2010; 347: 279-96.
26. Stupp R, Mason W P, van den Bent M J, Weller M, Fisher B, Taphoorn M J, et al. Radiotherapy plus concomitant and adjuvant temozolomide for glioblastoma. N Engl J Med. 2005; 352:987-96.
27. Auperin A, Le Pechoux C, Rolland E, Curran W J, Furuse K, Fournel P, et al. Meta-analysis of concomitant versus sequential radiochemotherapy in locally advanced non-small-cell lung cancer. J Clin Oncol. 2010; 28:2181-90.
28. Barani I J, Larson D A. Radiation therapy of glioblastoma. Cancer Treat Res. 2015; 163:49-73.
29. Alewine C, Olsen O, Wade J B, Welling P A. TIP-1 has PDZ scaffold antagonist activity. Mol Biol Cell. 2006; 17:4200-11.
30. Rousset R, Fabre S, Desbois C, Bantignies F, Jalinot P. The C-terminus of the HTLV-1 Tax oncoprotein mediates interaction with the PDZ domain of cellular proteins. Oncogene. 1998; 16:643-54.
31. Hampson L, Li C, Oliver A W, Kitchener H C, Hampson I N. The PDZ protein Tip-1 is a gain of function target of the HPV16 E6 oncoprotein. Int J Oncol. 2004; 25:1249-56.
32. Reynaud C, Fabre S, Jalinot P. The PDZ protein TIP-1 interacts with the Rho effector rhotekin and is involved in Rho signaling to the serum response element. J Biol Chem. 2000; 275:33962-8.
33. Besser J, Leito J T, van der Meer D L, Bagowski C P. Tip-1 induces filopodia growth and is important for gastrulation movements during zebrafish development. Dev Growth Differ. 2007; 49:205-14.
34. Scott A M, Wolchok J D, Old L J. Antibody therapy of cancer. Nature reviews cancer. 2012; 12:278-87.
35. Topper M B, Tonra J R, Pytowski B, Eastman S W. Differentiation between the E G F R antibodies necitu mu mab, cetuximab, and panitumumab: Antibody internalization and EGFR degradation. Journal of clinical oncology: official journal of the American Society of Clinical Oncology. 2011; 29:e13022.
36. Han M, Wang H, Zhang H T, Han Z. Expression of TIP-1 confers radioresistance of malignant glioma cells. PloS one. 2012; 7:e45402.
37. Wang H, Han M, Whetsell W, Jr., Wang J, Rich J, Hallahan D, et al. Tax-interacting protein 1 coordinates the spatiotemporal activation of Rho GTPases and regulates the infiltrative growth of human glioblastoma. Oncogene. 2014; 33:1558-69.
38. Kwon T, Kwon D Y, Chun J, Kim J H, Kang S S. Akt protein kinase inhibits Rac1-GTP binding through phosphorylation at serine 71 of Rac1. The Journal of biological chemistry. 2000; 275:423-8.
39. Kanamori M, Sandy P, Marzinotto S, Benetti R, Kai C, Hayashizaki Y, et al. The PDZ protein tax-interacting protein-1 inhibits beta-catenin transcriptional activity and growth of colorectal cancer cells. The Journal of biological chemistry. 2003; 278:38758-64.

What is claimed is:

1. An isolated anti-TIP1 antigen binding protein comprising (a) a heavy chain variable region comprising a CDR1 of SEQ ID NO: 4, a CDR2 of SEQ ID NO: 5, and a CDR3 of SEQ ID NO: 6; and (b) a light chain variable region comprising a CDR1 of SEQ ID NO: 7, a CDR2 of SEQ ID NO: 8, and a CDR3 of SEQ ID NO: 9 or 10.

2. The isolated antigen binding protein of claim 1, wherein the framework region of each variable region has at least 90% sequence identity with a human framework region sequence.

3. The isolated antigen binding protein of claim 1, wherein the isolated binding protein further comprises one or more constant regions, or a portion of a constant region, that has at least 90% sequence identity with human constant region sequence.

4. The isolated antigen binding protein of claim 1, wherein the antigen binding protein is a monoclonal antibody.

5. The A pharmaceutical composition comprising the isolated antigen binding protein of claim 1 and a pharmaceutically acceptable carrier or excipient.

6. The isolated antigen binding protein of claim 1, wherein the antigen binding protein is selected from the group consisting of a single-chain antibody, an antibody fragment, a chimeric antibody, or a humanized antibody.

7. The isolated antigen binding protein of claim 1, wherein the antigen binding protein is conjugated directly or indirectly to a payload selected from the group consisting of a detectable label, a therapeutic agent, or a combination thereof.

8. The isolated antigen binding protein of claim 7, wherein the detectable label and/or therapeutic agent is a radionuclide.

9. A method of detecting a tumor in a subject, the method comprising:
   a) exposing a target area of the subject where the presence of a tumor is suspected to ionizing radiation;
   b) administering to the subject a composition to detect the presence of TIP in the target area, wherein the composition comprises an antigen binding protein according to claim 1 that is conjugated to a detectable label; and
   c) detecting the detectable label to detect the presence of TIP 1, wherein the presence of TIP1 indicates the presence of a tumor in the target area of the subject.

10. The method of claim 9, wherein the exposing comprises exposing the tumor to less than about 2 Gy ionizing radiation.

11. The method of claim 9, wherein the exposing comprises exposing the tumor to at least about 2 Gy ionizing radiation.

12. The method of claim 9, wherein the exposing comprises exposing the tumor to about 10 Gy to about 20 Gy ionizing radiation.

13. The method of claim 9, wherein the administering comprises administering the antibody subsequent to radiation exposure.

14. The method of claim 9, wherein the administering comprises administering the antibody 0 hours to about 24 hours following radiation exposure.

\* \* \* \* \*